US012221631B2

(12) United States Patent
Yu et al.

(10) Patent No.: US 12,221,631 B2
(45) Date of Patent: Feb. 11, 2025

(54) ENGINEERED MIGRASOME, METHOD FOR PREPARING SAME, AND USES THEREOF

(71) Applicant: BEIJING MIGRASOME THERAPEUTICS LIMITED, Beijing (CN)

(72) Inventors: Li Yu, Beijing (CN); Dongju Wang, Zhejiang (CN); Chen Dai, Beijing (CN); Moye Jia, Beijing (CN); Shuo Wang, Beijing (CN); Tianlun Ding, Beijing (CN); Qiushi Zhong, Shanghai (CN); Yi Zheng, Guizhou (CN)

(73) Assignee: BEIJING MIGRASOME THERAPEUTICS LIMITED, Beijing (CN)

( * ) Notice: Subject to any disclaimer, the term of this patent is extended or adjusted under 35 U.S.C. 154(b) by 0 days.

(21) Appl. No.: 18/351,696

(22) Filed: Jul. 13, 2023

(65) Prior Publication Data
US 2024/0084264 A1 Mar. 14, 2024

Related U.S. Application Data

(63) Continuation of application No. PCT/CN2022/133863, filed on Nov. 24, 2022.

(30) Foreign Application Priority Data

Nov. 25, 2021 (CN) .......................... 202111412950.1

(51) Int. Cl.
 *C12N 5/071* (2010.01)
 *C12N 5/09* (2010.01)
(52) U.S. Cl.
 CPC ......... *C12N 5/0686* (2013.01); *C12N 5/0693* (2013.01); *C12N 2500/60* (2013.01)
(58) Field of Classification Search
None
See application file for complete search history.

(56) References Cited

FOREIGN PATENT DOCUMENTS

| CN | 102985556 | 3/2013 |
| CN | 109628452 | 4/2019 |
| CN | 111197057 | 5/2020 |

OTHER PUBLICATIONS

Wu, Danni, et al. "Pairing of integrins with ECM proteins determines migrasome formation." Cell Research 27.11 (2017): 1397-1400. (Year: 2017).*
International Search Report issued Feb. 6, 2023, in Chinese Patent Application No. PCT/CN2022/133863. (References 13, 14, 15, 20, 21, 22, 23, and 24 are cited therein).
Wang Yongsheng et al. "Research progress on the role of nerve cytoskeleton in nerve cell migration". *Military Medical Journal of Southeast China*, vol. 20, Issue 01, Jan. 20, 2018 (Jan. 20, 2018), pp. 54-56 (with English Abstract).
Jin Ying et al. "Progress in research on glomerular podocyte cytoskeleton proteins", *Journal of Clinical and Pathology*, vol. 40, Issue 04, Apr. 28, 2020 (Apr. 28, 2020), pp. 971-976, (with English Abstract).
Qin Wei et al. "Research Progress on Cytoskeleton and Cell Migration", *Chinese Ethnic Folk Medicine*, No. 23, Dec. 15, 2014 (Dec. 15, 2014), pp. 24-25, (with English Abstract).
Taïeb, H.M. et al. "Osmotic pressure modulates single cell cycle dynamics inducing reversible growth arrest and reactivation of human metastatic cells" *Sci Rep.*, vol. 11, Issue 1, Jun. 29, 2021 (Jun. 29, 2021), pp. 1-13 of Section 13455.
Guo Rui. "CLC-3 regulates the migration of epidermal stem cells to repair skin wounds" *China Doctoral Dissertation Full-text Database Medical and Health Science and Technology Series*, Issue 02, Feb. 15, 2017 (Feb. 15, 2017), pp. 1-144.
Stanley Cohen et al., "A Native 170,000 Epidermal Growth Factor Receptor-Kinase Complex from Shed Plasma Membrane Vesicles", *Journal of Biological Chemistry*, vol. 257, No. 3, Feb. 10, 1982, pp. 1523-1531.
Xianjun Gao, et al., "Anchor Peptide Captures, Targets, and Loads Exosomes of Diverse Origins for Diagnostics and Therapy", *Sci. Transl. Med.*, vol. 10, eaat0195 (2018), pp. 1-14.
Xiaoxin Zhao, et al., Author correction: "Identification of Markers for Migrasome Detection", *Cell Discovery*, (2019) 5:27.
Ryosuke Kojima et al., "Designer Exosomes Produced by Implanted Cells Intracerebrally Deliver Therapeutic Cargo for Parkinson's Disease Treatment", *Nature Communications*, (2018) 9:1305, 10 pages.
Liang Ma, et al., "Discovery of the Migrasome, an Organelle Mediating Release of Cytoplasmic Contents During Cell Migration", *Cell Research*, (2015) 25: pp. 24-38.
Yulia Zhitnyuk et al., "Efficient mRNA Delivery System Utilizing Chimeric VSVG-L7Ae Virus-Like Particles," *Biochemical and Biophysical Research Communications*, (2018) pp. 1-6.
Sushrut Kamerkar, et al., "Exosomes Facilitate Therapeutic Targeting of Oncogenic KRAS in Pancreatic Cancer", Nature, vol. 000, (2017), pp. 1-24.
Georgyi V. Los, et al., "Halo Tag: A Novel Protein Labeling Technology for Cell Imaging and Protein Analysis", *ACS Chemical Biology*, vol. 3, No. 6, pp. 373-382 (2008).
Anne Prel, et al., "Highly Efficient in vitro and in vivo Delivery of Functional RNAs Using New Versatile MS2-Chimeric Retrovirus-Like Particles", *Molecular Therapy—Methods & Clinical Development*, (2015) 2, 15039, pp. 1-15.
Xiaoxin Zhao, et al., "Identification of Markers for Migrasome Detection", *Cell Discovery*, (2019) 5:27, pp. 1-4.
Letter to the Editor, "Lateral Transfer of mRNA and Protein by Migrasomes Modifies the Recipient Cells," *Cell Research*, (2021) 31:237-240.

(Continued)

*Primary Examiner* — Robert J Yamasaki
(74) *Attorney, Agent, or Firm* — Merchant & Gould P.C.; Daniel J. Pereira

(57) ABSTRACT

The present invention relates to the field of biomedicine, and in particular to an engineered migrasome, a method for preparing the engineered migrasome, a delivery system comprising the engineered migrasome, and a method for preparing the delivery system.

19 Claims, 65 Drawing Sheets

Specification includes a Sequence Listing.

(56) References Cited

OTHER PUBLICATIONS

Yuwei Huang et al., "Migrasome Formation is Mediated by Assembly of Micron-Scale Tetraspanin Macrodomains", *Nature Cell Biology*, vol. 21, Aug. 2019 (991-1002).
Dong Jiang, et al., "Migrasomes Provide Regional Cues for Organ Morphogenesis During Zebrafish Gastrulation", *Nature Cell Biology*, vol. 21, Aug. 2019, 966-977.
Jiao, et al., "Mitocytosis, a Migrosome-Mediated Mitochondrial Quality-Control Process", *Cell*, 184, (2021) pp. 2896-2910.
Saigopalakrishna S. Yerneni, et al., "Rapid On-Demand Extracellular Vesicle Augmentation with Versatile Oligonucleotide Tethers," *ACS Nano*, (2019), vol. 13 pp. 10555-10565.
Tian T. Zhang, et al., "Surface Functionalized Exosomes as Targeted Drug Delivery Vehicles for Cerebral Ischemia Therapy", *Accepted Manuscript, Biomaterials* (2017) pp. 1-33.
Lilian Chen et al., "WGA is a Probe for Migrasomes", *Cell Discovery*, (2019) 5:13, pp. 1-3.

\* cited by examiner

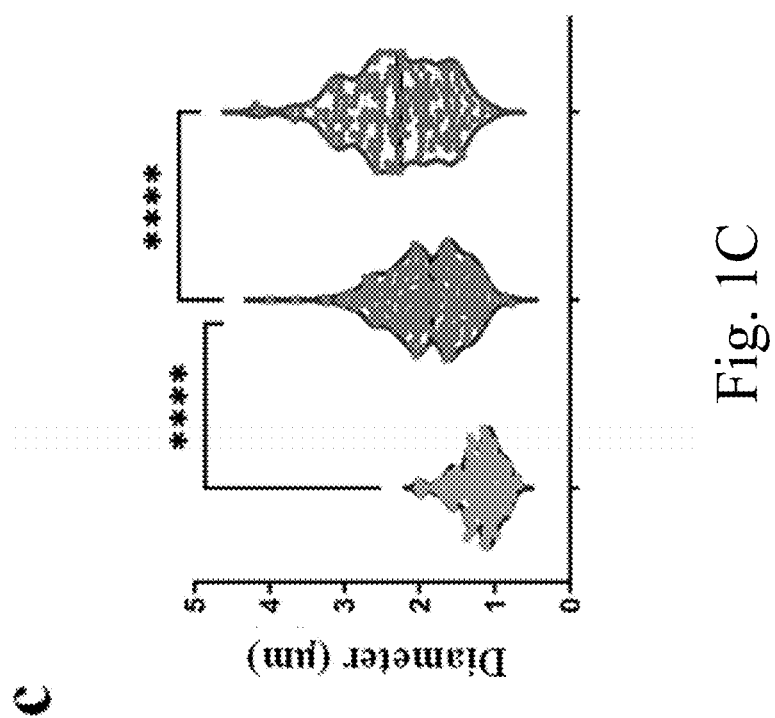

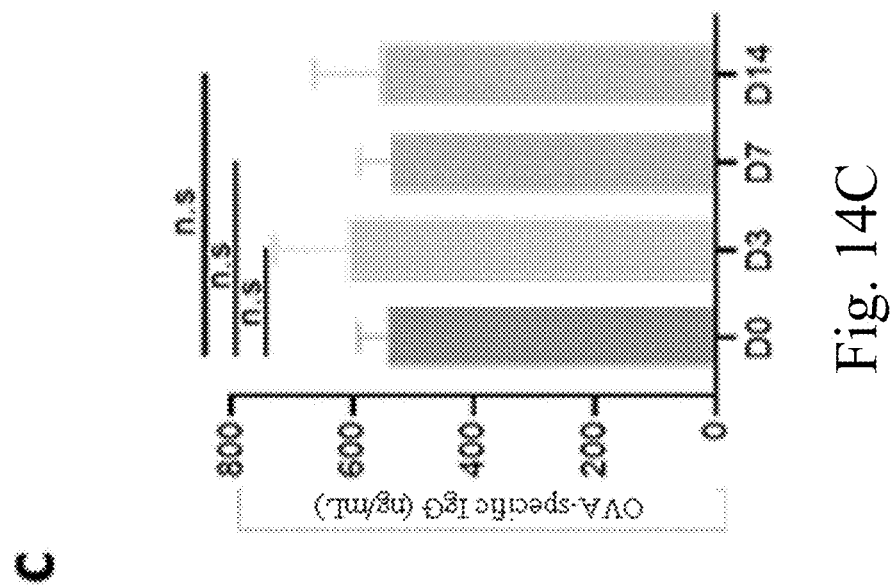

| Gene | Migrasome 1 | Migrasome 2 | Migrasome 3 | Mean |
|---|---|---|---|---|
| Myh4 | 10.0 | 14.7 | 100.0 | 41.6 |
| Gorasp2 | 0.4 | 0.7 | 89.4 | 30.2 |
| Aldl | 47.1 | 6.2 | 9.7 | 21.0 |
| Lats2 | 16.6 | 13.6 | 20.3 | 16.8 |
| Scn2b | 7.5 | 5.3 | 31.0 | 14.6 |
| Pacsin1 | 27.9 | 10.6 | 5.0 | 14.5 |
| Sfmbt1 | 17.5 | 23.1 | 1.3 | 14.0 |
| Dennd4a | 17.5 | 16.0 | 7.0 | 13.5 |
| Top1mt | 15.5 | 19.4 | 4.0 | 13.0 |
| Alb | 2.6 | 4.7 | 30.5 | 12.6 |
| LOC686013 | 10.0 | 15.4 | 12.2 | 12.5 |
| Atp5g1 | 0.5 | 3.9 | 29.8 | 11.4 |
| Slmap | 10.5 | 14.7 | 5.1 | 10.1 |
| Kif4l | 27.3 | 0.9 | 1.7 | 10.0 |
| F5 | 5.9 | 11.1 | 11.9 | 9.6 |
| Ifi47 | 7.7 | 7.9 | 10.7 | 8.8 |
| LOC100365259 | 14.7 | 0.9 | 6.9 | 7.5 |
| Tspan7 | 4.9 | 4.7 | 12.8 | 7.5 |
| Gtf3c2 | 0.8 | 18.5 | 1.3 | 6.9 |
| Utp15 | 14.7 | 1.2 | 0.8 | 5.6 |
| Cs93 | 9.0 | 3.3 | 4.1 | 5.5 |
| Msl1 | 14.9 | 0.5 | 0.5 | 5.3 |
| Tax1bp3 | 2.4 | 0.8 | 12.2 | 5.2 |
| Cpne2 | 6.6 | 1.1 | 7.8 | 5.1 |
| Nol11 | 6.2 | 8.6 | 0.6 | 5.1 |

Fig. 26G

|  | Small extracellular vesicles (small EVs) | Engineered migrasomes (eMigrasome) |
|---|---|---|
| Source cells | MC38-mTspan4-GFP | MC38-mTspan4-GFP |
| Source components | Supernatant of cell culture medium | Bottom of cell culture dish |
| Amount of media used | 1000 ml | 25 ml |
| Amount of cells used | ~1.1e9 | ~1e7 |
| Number of culture dishes used | 40 | 1 |
| Total amount of crude extracted proteins | 1848 μg | NA |
| Total amount of proteins after purification | 162 μg | 51.1 μg |
| Total number of vesicles after purification | 9.90E+11 | 1.10E+08 |
| Average vesicle size | 128.5 nm | 2100 nm |
| Purification time consumption | About 45 hours (centrifuge for about 20 hours) | About 3 hours (centrifuge for about 1 hour) |
| Unit yield (1e7 cells) | 1.47 μg | 51.1 μg |

Fig. 27E

| E-migrasomes 1-3 | Exosome-1 | Exosome-2 | Exosome-3 |
|---|---|---|---|
| Fzd6 | Itih1 | Josd2 | Zcchc2 |
| Yes1 | Trpm7 | Cd5l | Cd5l |
| Wasl | Tspan9 | Ckm | Timmdc1 |
| Slc9a1 | Plek | Efcab12 | Fmnl2 |
| Stx2 | CD5l | Srebf2 | Adcy9 |
| Ubtd1 | Rgs19 | Hp | Cmklr1 |
| Soga3 | Syngr2 | Litaf | C6 |
| Dag1 | Hp | Apom | Cd9 |
| Ccdc32 | Cep164 | Pnmal2 | Kirrel3 |
| Gnb1 | Colec11 | Ccdc113 | F5 |

Fig. 28C

SEQUENCE LISTING

```
Sequence total quantity: 7
SEQ ID NO: 1           moltype = AA  length = 479
FEATURE                Location/Qualifiers
REGION                 1..479
                       note = Tspan4-linker-GFP
source                 1..479
                       mol_type = protein
                       organism = synthetic construct
SEQUENCE: 1
MARGCLQGVK YLMFAFNLLF WLGGCGVLGV GIWLAATQGN FATLSSSFPS LSAANLLIVT    60
GTFVMAIGFV GCIGALKENK CLLLTFFVLL LLVFLLEATI AVLFFAYSDK IDSYAQQDLK   120
KGLHLYGTQG NVGLTNAWSI IQTDFRCCGV SNYTDWFEVY NATRVPDSCC LEFSDSCGLH   180
EPGTWWKSPC YETVKAWLQE NLLAVGIFGL CTALVQILGL TFAMTMYCQV VKADTYCAPG   240
```

```
MVSKGEELFT GVVPILVELD GDVNGHKFSV SGEGEGDATY GKLTLKFICT TGKLPVPWPT    300
LVTTLTYGVQ CFSRYPDHMK QHDFFKSAMP EGYVQERTIF FKDDGNYKTR AEVKFEGDTL    360
VNRIELKGID FKEDGNILGH KLEYNYNSHN VYIMADKQKN GIKVNFKIRH NIEDGSVQLA    420
DHYQQNTPIG DGPVLLPDNH YLSTQSALSK DPNEKRDHMV LLEFVTAAGI TLGMDELYK     479

SEQ ID NO: 2              moltype = AA   length = 1136
FEATURE                   Location/Qualifiers
REGION                    1..1136
                          note = DAG1-linker-mCherry
source                    1..1136
                          mol_type = protein
                          organism = synthetic construct
SEQUENCE: 2
MSVDNWLLHP LWGQTFLLLL SVAVAQAHWP SEPSEAVRDW KNQLEASMHS VLSDFQEAVP     60
TVVGIPDGTA VVGRSFRVSI PTDLIASSGE IIKVSAAGKE ALPSWLHWDP HSHILEGLPL    120
DTDKGVHYIS VSAARLGANG SHVPQTASVF SIEVYPEDHS EPQSVRAASS DPGEVVSSAC    180
AADEPVTVLT VILDADLTKM TPKQRIDLLN RMQSFSEVEL NNMKLVPVVN NRLFDMSAFM    240
AGPGNAKKVV ENGALLSWKL GCSLNQNSVP DIRGVETPAR EGTMSAHLGY PVVGWHIANK    300
KPTLPKRIRR QIHATPTPVT AIGPPTTAIQ EPPSRIVPTP TSPAIAPPTE TMAPPVRDPV    360
PGKPTVTIRT RGAIIQTPTL GPIPPTRVSE AGTTVPGQIR PTLTIPGYVE PTAVVTPPTT    420
TTKKPRVSTP KPATPSTDSS TTTTRRPTKK PRTPRPVPRV TTKAPITRLE TASPPTRIRT    480
TTSAVPRGGE ANQRPELKNH IDRVDAWVGT YFEVKIPSDT FYDNEDTTTD KLKLTLKLRE    540
QQLVGEKSWV QFNSNSQLMY GLPDSSHVGK HEYFMHATDK GGLSAVDAFE IHVHKRPQGD    600
KAPARFKAKL AGDPAPVVND IHKKIALVKK LAFAFGDRNC SSITLQNITR GSIVVEWTNN    660
TLPLEPCPKE QIVGLSRRIA DENGKPRPAF SNALEPDFKA LSVAVAGSGS CRHLQFIPVA    720
PPSPGTSAAP ATEVPDRDPE KSSEDDVYLH TVIPAVVVEA ILLIAGIIAM ICYRKKRKGK    780
LTLEDQATFI KKGVPIIFAD ELDDSKPPPS SSMPLILQEE KAPLPPPEYP NQSVPETTPL    840
NQDTVGEYTP LRDEDPNAPP YQPPPPFTAP MEGKGSRPKN MTPYRSPPPY VPPGDPPVAT    900
MVSKGEEDNM AIIKEFMRFK VHMEGSVNGH EFEIEGEGEG RPYEGTQTAK LKVTKGGPLP    960
FAWDILSPQF MYGSKAYVKH PADIPDYLKL SFPEGFKWER VMNFEDGGVV TVTQDSSLQD   1020
GEFIYKVKLR GTNFPSDGPV MQKKTMGWEA SSERMYPEDG ALKGEIKQRL KLKDGGHYDA   1080
EVKTTYKAKK PVQLPGAYNV NIKLDITSHN EDYTIVEQYE RAEGRHSTGG MDELYK       1136

SEQ ID NO: 3              moltype = AA   length = 536
FEATURE                   Location/Qualifiers
REGION                    1..536
                          note = PDCD1-linker-mCherry
source                    1..536
                          mol_type = protein
                          organism = synthetic construct
SEQUENCE: 3
MWVRQVPWSF TWAVLQLSWQ SGWLLEVPNG PWRSLTFYPA WLTVSEGANA TFTCSLSNWS     60
EDLMLNWNRL SPSNQTEKQA AFCNGLSQPV QDARFQIIQL PNRHDFHMNI LDTRRNDSGI    120
YLCGAISLHP KAKIEESPGA ELVVTERILE TSTRYPSPSP KPEGRFQGMV IGIMSALVGI    180
PVLLLLAWAL AVFCSTSMSE ARGAGSKDDT LKEEPSAAPV PSVAYEELDF QGREKTPELP    240
TACVHTEYAT IVFTEGLGAS AMGRRGSADG LQGPRPPRHE DGHCSWPLTV PRARDPPVAT    300
MVSKGEEDNM AIIKEFMRFK VHMEGSVNGH EFEIEGEGEG RPYEGTQTAK LKVTKGGPLP    360
FAWDILSPQF MYGSKAYVKH PADIPDYLKL SFPEGFKWER VMNFEDGGVV TVTQDSSLQD    420
GEFIYKVKLR GTNFPSDGPV MQKKTMGWEA SSERMYPEDG ALKGEIKQRL KLKDGGHYDA    480
EVKTTYKAKK PVQLPGAYNV NIKLDITSHN EDYTIVEQYE RAEGRHSTGG MDELYK        536

SEQ ID NO: 4              moltype = AA   length = 751
FEATURE                   Location/Qualifiers
REGION                    1..751
                          note = Tgfbr1-linker-mCherry
source                    1..751
                          mol_type = protein
                          organism = synthetic construct
SEQUENCE: 4
MEAAAAAPRR PQLLIVLVAA ATLLPGAKAL QCFCHLCTKD NFTCETDGLC FVSVTETTDK     60
VIHNSMCIAE IDLIPRDRPF VCAPSSKTGA VTTTYCCNQD HCNKIELPTT GPFSEKQSAG    120
LGPVELAAVI AGPVCFVCIA LMLMVYICHN RTVIHHRVPN EEDPSLDRPF ISEGTTLKDL    180
IYDMTTGSGS GLPLLVQRT IARTIVLQES IGKGRFGEVW RGKWRGEEVA VKIFSSREER    240
SWFREAEIYQ TVMLRHENIL GFIAADNKDN GTWTQLWLVS DYHEHGSLFD YLNRYTVTVE    300
GMIKLALSTA SGLAHLHMEI VGTQGKPAIA HRDLKSKNIL VKKNGTCCIA DLGLAVRHDS    360
ATDTIDIAPN HRVGTKRYMA PEVLDDSINM KHFESFKRAD IYAMGLVFWE IARRCSIGGI    420
HEDYQLPYYD LVPSDPSVEE MRKVVCEQKL RPNIPNRWQS CEALRVMAKI MRECWYANGA    480
ARLTALRIKK TLSQLSQQEG IKMTVPRARD PPVATMVSKG EEDNMAIIKE FMRFKVHMEG    540
SVNGHEFEIE GEGEGRPYEG TQTAKLKVTK GGPLPFAWDI LSPQFMYGSK AYVKHPADIP    600
DYLKLSFPEG FKWERVMNFE DGGVVTVTQD SSLQDGEFIY KVKLRGTNFP SDGPVMQKKT    660
MGWEASSERM YPEDGALKGE IKQRLKLKDG GHYDAEVKTT YKAKKPVQLP GAYNVNIKLD    720
ITSHNEDYTI VEQYERAEGR HSTGGMDELY K                                  751

SEQ ID NO: 5              moltype = AA   length = 431
FEATURE                   Location/Qualifiers
REGION                    1..431
                          note = mCherry-linker-Kras
source                    1..431
                          mol_type = protein
```

```
                                organism = synthetic construct
SEQUENCE: 5
MVSKGEEDNM  AIIKEFMRFK  VHMEGSVNGH  EFEIEGEGEG  RPYEGTQTAK  LKVTKGGPLP   60
FAWDILSPQF  MYGSKAYVKH  PADIPDYLKL  SFPEGFKWER  VMNFEDGGVV  TVTQDSSLQD  120
GEFIYKVKLR  GTNFPSDGPV  MQKKTMGWEA  SSERMYPEDG  ALKGEIKQRL  KLKDGGHYDA  180
EVKTTYKAKK  PVQLPGAYNV  NIKLDITSHN  EDYTIVEQYE  RAEGRHSTGG  MDELYKSGLR  240
SRGMTEYKLV  VVGAGGVGKS  ALTIQLIQNH  FVDEYDPTIE  DSYRKQVVID  GETCLLDILD  300
TAGQEEYSAM  RDQYMRTGEG  FLCVFAINNT  KSFEDIHHYR  EQIKRVKDSE  DVPMVLVGNK  360
CDLPSRTVDT  KQAQELARSY  GIPFIETSAK  TRQGVDDAFY  TLVREIRKHK  EKMSKDGKKK  420
KKKSRTRCIV  M                                                          431

SEQ ID NO: 6                moltype = AA   length = 670
FEATURE                     Location/Qualifiers
REGION                      1..670
                            note = t-STX2-linker-OVA-linker-mCherry
source                      1..670
                            mol_type = protein
                            organism = synthetic construct
SEQUENCE: 6
MKKAIKYQSK  ARRKKWIIAA  VAVAVIAVLA  LIIGLSVGKG  SMGSIGAASM  EFCFDVFKEL   60
KVHHANENIF  YCPIAIMSAL  AMVYLGAKDS  TRTQINKVVR  FDKLPGFGDS  IEAQCGTSVN  120
VHSSLRDILN  QITKPNDVYS  FSLASRLYAE  ERYPILPEYL  QCVKELYRGG  LEPINFQTAA  180
DQARELINSW  VESQTNGIIR  NVLQPSSVDS  QTAMVLVNAI  VFKGLWEKAF  KDEDTQAMPF  240
RVTEQESKPV  QMMYQIGLFR  VASMASEKMK  ILELPFASGT  MSMLVLLPDE  VSGLEQLESI  300
INFEKLTEWT  SSNVMEERKI  KVYLPRMKME  EKYNLTSVLM  AMGITDVFSS  SANLSGISSA  360
ESLKISQAVH  AAHAEINEAG  REVVGSAEAG  VDAASVSEEF  RADHPFLFCI  KHIATNAVLF  420
FGRCVSPGDP  PVATMVSKGE  EDNMAIIKEF  MRFKVHMEGS  VNGHEFEIEG  EGEGRPYEGT  480
QTAKLKVTKG  GPLPFAWDIL  SPQFMYGSKA  YVKHPADIPD  YLKLSFPEGF  KWERVMNFED  540
GGVVTVTQDS  SLQDGEFIYK  VKLRGTNFPS  DGPVMQKKTM  GWEASSERMY  PEDGALKGEI  600
KQRLKLKDGG  HYDAEVKTTY  KAKKPVQLPG  AYNVNIKLDI  TSHNEDYTIV  EQYERAEGRH  660
STGGMDELYK                                                             670

SEQ ID NO: 7                moltype = AA   length = 778
FEATURE                     Location/Qualifiers
REGION                      1..778
                            note = Tspan4-linker-GFP-linker-Halo
source                      1..778
                            mol_type = protein
                            organism = synthetic construct
SEQUENCE: 7
MARGCLQGVK  YLMFAFNLLF  WLGGCGVLGV  GIWLAATQGN  FATLSSSFPS  LSAANLLIVT   60
GTFVMAIGFV  GCIGALKENK  CLLLTFFVLL  LLVFLLEATI  AVLFFAYSDK  IDSYAQQDLK  120
KGLHLYGTQG  NVGLTNAWSI  IQTDFRCCGV  SNYTDWFEVY  NATRVPDSCC  LEFSDSCGLH  180
EPGTWWKSPC  YETVKAWLQE  NLLAVGIFGL  CTALVQILGL  TFAMTMYCQV  VKADTYCAPG  240
MVSKGEELFT  GVVPILVELD  GDVNGHKFSV  SGEGEGDATY  GKLTLKFICT  TGKLPVPWPT  300
LVTTLTYGVQ  CFSRYPDHMK  QHDFFKSAMP  EGYVQERTIF  FKDDGNYKTR  AEVKFEGDTL  360
VNRIELKGID  FKEDGNILGH  KLEYNYNSHN  VYIMADKQKN  GIKVNFKIRH  NIEDGSVQLA  420
DHYQQNTPIG  DGPVLLPDNH  YLSTQSALSK  DPNEKRDHMV  LLEFVTAAGI  TLGMDELYKG  480
SMAEIGTGFP  FDPHYVEVLG  ERMHYVDVGP  RDGTPVLFLH  GNPTSSYVWR  NIIPHVAPTH  540
RCIAPDLIGM  GKSDKPDLGY  FFDDHVRFMD  AFIEALGLEE  VVLVIHDWGS  ALGFHWAKRN  600
PERVKGIAFM  EFIRPIPTWD  EWPEFARETF  QAFRTTDVGR  KLIIDQNVFI  EGTLPMGVVK  660
PLTEVEMDHY  REPFLNPVDR  EPLWRFPNEL  PIAGEPANIV  ALVEEYMDWL  HQSPVPKLLF  720
WGTPGVLIPP  AEAARLAKSL  PNCKAVDIGP  GLNLLQEDNP  DLIGSEIARW  LSTLEISG    778
```

ENGINEERED MIGRASOME, METHOD FOR PREPARING SAME, AND USES THEREOF

CROSS-REFERENCE TO RELATED APPLICATIONS

This application is a National Stage Application and claims priority under 35 U.S.C. § 371 to Patent Cooperation Treaty application PCT/CN2022/133863, filed Nov. 24, 2022, which claims the benefit of China Patent Application CN2021114129501, filed Nov. 25, 2021. Priority is claimed to these applications and the disclosures of these prior applications are considered part of the disclosure of this application and to the extent allowed the entire contents of the aforementioned applications are incorporated herein.

TECHNICAL FIELD

The present invention relates to the field of biomedicine, and in particular to an engineered migrasome, a method for preparing the engineered migrasome, a delivery system comprising the engineered migrasome, and a method for preparing the delivery system.

BACKGROUND ART

There are many issues with the existing delivery system in the art. For example, bio-derived nanoparticle and microparticle delivery systems have high biocompatibility and relatively good targeting ability, but are difficult to produce; engineered exosomes show obvious limitations, such as low production yield, requirement of ultracentrifugation during purification, and cargos limited to mainly nucleic acids loaded after production; engineered red blood cells require blood samples for each preparation as they cannot be continuously cultured or proliferated in vitro; red blood cells are also highly limited in cargo types, which mostly include nucleic acids; membrane-modified nanoparticles are difficult to be eliminated by the normal metabolism of a human body, and thus may accumulate in the body, presenting potential toxicity; cargos that can be delivered by viruses and virus-like particles are basically limited to nucleic acids and small molecular weight proteins, while the production and purification of viruses and virus-like particles are difficult and expensive, with difficulty in modification; etc. Therefore, there is a need in the art for a new delivery system capable of overcoming one or more types of shortcomings present in the existing drug delivery systems.

In the present application, it is found that the generation of engineered migrasomes similar in structure to natural migrasomes can be induced by a variety of methods, and these engineered migrasomes are different from the "hypotonically induced vesicles" known in the art. In the present application, it is simultaneously found that the engineered migrasome is of a biological origin, which has the advantages of low toxicity and low immunogenicity; the engineered migrasome is a newly discovered extracellular vesicle with unique advantages in cargo molecule types and biodistribution in vivo; and at the same time, the method for preparing the engineered migrasome is simple with high yield. Therefore, the engineered migrasome provided by the present application has very high application values in biomedical fields such as drug delivery and vaccine preparation.

SUMMARY OF THE INVENTION

The present application provides an engineered migrasome, a method for preparing the engineered migrasome, a delivery system comprising the engineered migrasome, and a method for preparing the delivery system. The engineered migrasome includes, but is not limited to, the following advantages: low toxicity, low immunogenicity, ability to deliver a variety of exogenous cargo molecules, appropriate biodistribution in vivo, simple preparation method, and/or high yield. The engineered migrasome provided by the present application can be used for drug delivery and vaccine preparation or the like, showing excellent effects.

In one aspect, the present application provides a method for preparing a migrasome, comprising enabling the relative movement of a cell and then produce a migrasome derived from the cell.

In the method according to an embodiment, wherein the method further comprises isolating the migrasome produced by the cell.

In the method according to an embodiment, wherein the method comprises carrying out hypotonic treatment to the cell.

In the method according to an embodiment, wherein the hypotonic treatment comprises placing the cell in a hypotonic buffer solution.

In the method according to an embodiment, wherein the hypotonic treatment comprises placing the cell in a buffer solution, and reducing an osmolality of the buffer solution to turn the buffer solution into a hypotonic buffer solution.

In the method according to an embodiment, wherein the reducing comprises linear reducing and/or stepwise reducing.

In the method according to an embodiment, wherein the osmolality of the hypotonic buffer solution is less than about 305 mOsmol/L.

In the method according to an embodiment, wherein the osmolality of the hypotonic buffer solution is about 10 mOsmol/L to about 274.5 mOsmol/L.

In the method according to an embodiment, wherein the method comprises disrupting a cytoskeleton of the cell.

In the method according to an embodiment, wherein disrupting the cytoskeleton of the cell comprises bringing the cell into contact with a cytoskeleton-disrupting reagent.

In the method according to an embodiment, wherein the cytoskeleton-disrupting reagent comprises a microfilament and/or microtubule depolymerizing agent.

In the method according to an embodiment, wherein the cytoskeleton-disrupting reagent comprises Latrunculin A, Latrunculin B, cytochalasin A, cytochalasin B, cytochalasin C, cytochalasin D, and/or cytochalasin E.

In the method according to an embodiment, wherein the method comprises suppressing a cell volume-regulatory function of the cell.

In the method according to an embodiment, wherein suppressing the cell volume-regulatory function of the cell comprises decreasing the number and/or function of a volume-regulatory protein in the cell.

In the method according to an embodiment, wherein the volume-regulatory protein comprises a volume-regulatory ion channel and/or a transporter.

In the method according to an embodiment, wherein the volume-regulatory ion channel comprises a volume-regulatory anion channel VRAC and/or a volume-regulatory cation channel VRCC.

In the method according to an embodiment, wherein the volume-regulatory anion channel VRAC comprises SWELL1 or a functionally active fragment thereof.

In the method according to an embodiment, wherein the volume-regulatory cation channel VRCC comprises TRPV4, TRPM3, and/or functionally active fragments thereof.

In the method according to an embodiment, wherein the transporter comprises a cotransporter.

In the method according to an embodiment, wherein the cotransporter comprises KCC1, KCC3 and/or KCC4.

In the method according to an embodiment, wherein suppressing the cell volume-regulatory function of the cell comprises placing the cell in a buffer solution that can inhibit is generated from regulatory ability of the cell.

In the method according to an embodiment, wherein the buffer solution comprises increased cations.

In the method according to an embodiment, wherein the cations comprise $K^+$, $Na^+$, $Cs^+$, $Li^+$, $Ca^{2+}$, $Mg^{2+}$, $Ba^{2+}$, $Mn^{2+}$, $Fe^{2+}$, $Ni^{2+}$, $Zn^{2+}$, $Al^{3+}$, $Fe^{3+}$, $CH_3NH_3^+$, $C_2H_5NH_3^+$, $(CH_3)_2NH_2^+$, $(C_2H_5)_2NH_2^+$, $(C_2H_5)_3N^+$, ammonia ions and/or choline ions.

In the method according to an embodiment, wherein the buffer solution comprises increased anions.

In the method according to an embodiment, wherein the anions comprise $Br^-$, $Cl^-$, $I^-$, $F^-$, $OH^-$, $HCO_3^-$, $H_2PO_4^-$, $NO_2^-$, $NO_3^-$, $CN^-$, $HPO_4^{2-}$, $CO_3^{2-}$, $SO_4^{2-}$ and/or $PO_4^{3-}$.

In the method according to an embodiment, wherein the method comprises detaching the cell from a surface adhered thereto.

In the method according to an embodiment, wherein the method comprises allowing relative movement to occur between a cytomembrane of the cell relative to the surface the cell adhered thereto.

In the method according to an embodiment, wherein the method further comprises increasing the number and/or function of a tetraspanin protein, a functional fragment thereof and/or a functional variant thereof in the cell.

In the method according to an embodiment, wherein the method comprises allowing the cell to overexpress the tetraspanin protein, the functional fragment thereof and/or the functional variant thereof.

In the method according to an embodiment, wherein the tetraspanin protein is selected from: Tspan1, Tspan2, Tspan3, Tspan4, Tspan5, Tspan6, Tspan7, Tspan8, Tspan9, Tspan10, Tspan11, Tspan12, Tspan13, Tspan14, Tspan15, Tspan16, Tspan17, Tspan18, Tspan19, Tspan20 (UPK1B), Tspan21 (UPK1A), Tspan22 (PRPH2), Tspan23 (ROM1), Tspan24 (CD151), Tspan25 (CD53), Tspan26 (CD37), Tspan27 (CD82), Tspan28 (CD81), Tspan29 (CD9), Tspan30 (CD63), Tspan31, Tspan32, and Tspan33.

In the method according to an embodiment, wherein the method further comprises reducing a size of the migrasome.

In the method according to an embodiment, wherein the reducing the size of the migrasome comprises extruding the migrasome with a filter or an extruder.

In the method according to an embodiment, wherein the filter or extruder has a pore size of about 30 nm to about 10000 nm.

In the method according to an embodiment, wherein the migrasome has a size of about 50 nm to about 8000 nm.

In the method according to an embodiment, wherein the migrasome is generated from a retraction fiber of the cell.

In the method according to an embodiment, wherein a membrane of the migrasome is enriched with sodium/potassium ATPase and/or a functional fragment thereof.

In the method according to an embodiment, wherein the membrane of the migrasome is enriched with an integrin and/or a functional fragment thereof.

In the method according to an embodiment, wherein the membrane of the migrasome is enriched with a tetraspanin protein, a functional variant thereof and/or a functional fragment thereof.

In the method according to an embodiment, wherein the membrane of the migrasome is enriched with cholesterol.

In the method according to an embodiment, wherein the migrasome is enriched with a membrane microdomain.

In the method according to an embodiment, wherein the migrasome is produced in vitro or ex vivo.

In the method according to an embodiment, wherein contents of the migrasome are at least partially reduced or absent compared to a naturally occurring migrasome produced by a corresponding cell.

In the method according to an embodiment, wherein the at least partially reduced contents comprise intraluminal vesicles.

In the method according to an embodiment, wherein the method is an in vitro or ex vivo method.

In the method according to an embodiment, wherein the cell is a cell cultured in vitro.

In the method according to an embodiment, wherein the cell is a cell cultured in suspension or cultured by adherence.

In the method according to an embodiment, wherein the cell comprises a primary cell.

In the method according to an embodiment, wherein the primary cell comprises a tissue cell derived from an organism, which comprises a human, a monkey, a mouse, a rat, a rabbit, a chicken, and/or an insect.

In the method according to an embodiment, wherein the primary cell comprises a liver cell, a spleen cell, a kidney cell, a tissue macrophage, a cerebral glial cell, an osteoclast, a bone marrow cell, a leukocyte, a fibroblast, and/or a fat cell.

In the method according to an embodiment, wherein the leukocytes comprise a B cell, a T cell, an NK cell, a dendritic cell, a neutrophil, and/or a macrophage.

In the method according to an embodiment, wherein the cell includes a tumor cell.

In the method according to an embodiment, wherein the tumor cell comprises a tumor cell line, a primary or limited-passaged tumor cell derived from a patient, a tumor stromal cell, and/or a tumor organoid.

In the method according to an embodiment, wherein the cell comprises a CHO cell, a CHO-K1 cell, an HEK293 cell, an HEK293T cell, an HEK293FT cell, an HEK293F cell, a Vero cell, a NRK cell, a L929 cell, a MC38 cell, a 4T1 cell, a DC2.4 cell, an MGC803 cell, a Jurkat cell, an NK-92MI cell, a BJ cell, and/or an HepG2 cell.

In the method according to an embodiment, wherein the cell comprises a leukocyte, a stem cell, and/or a fibroblast.

In the method according to an embodiment, wherein the stem cell comprises a mesenchymal stem cell.

A migrasome is prepared in the method according to an embodiment.

In another aspect, the present application provides a migrasome prepared in vitro or ex vivo, wherein the migrasome has a size of about 50 nm to about 8000 nm.

In the migrasome according to an embodiment, wherein the migrasome is produced in vitro from a retraction fiber of a cell.

In the migrasome according to an embodiment, wherein a membrane of the migrasome is enriched with sodium/potassium ATPase and/or a functional fragment thereof.

In the migrasome according to an embodiment, wherein the membrane of the migrasome is enriched with an integrin and/or a functional fragment thereof.

In the migrasome according to an embodiment, wherein the membrane of the migrasome is enriched with a tetraspanin protein, a functional variant thereof and/or a functional fragment thereof.

In the migrasome according to an embodiment, wherein the membrane of the migrasome is enriched with cholesterol.

In the migrasome according to an embodiment, wherein the migrasome is enriched with a membrane microdomain.

In the migrasome according to an embodiment, wherein contents of the migrasome are at least partially reduced or absent compared to a naturally occurring migrasome produced by a corresponding cell.

In the migrasome according to an embodiment, wherein said at least partially reduced contents comprise intraluminal vesicles.

In another aspect, the present application provides use of a migrasome in delivery of an exogenous cargo.

In the use according to an embodiment, wherein the migrasome comprises the migrasome of the present application.

In another aspect, the present application provides a delivery system, wherein comprising a migrasome and one or more exogenous cargos.

In the delivery system according to an embodiment, wherein the exogenous cargo is incorporated into, conjugated to or intercalated to a membrane and/or interior of the migrasome, directly or indirectly.

In the delivery system according to an embodiment, wherein the migrasome comprises the migrasome of the present application.

In the delivery system according to an embodiment, wherein the migrasome is derived from a cell.

In the delivery system according to an embodiment, wherein the exogenous cargo comprises one or more targeting substances and/or therapeutically active substances.

In the delivery system according to an embodiment, wherein the exogenous cargo comprises a protein, a lipid, a polynucleotide, a small molecule compound, a complex, a polysaccharide, a polymer, a nanoparticle, a microparticle and/or an organelle.

In the delivery system according to an embodiment, wherein the exogenous cargo comprises a membrane protein, a soluble protein, and/or a polypeptide.

In the delivery system according to an embodiment, wherein the exogenous cargo comprises DNA and/or RNA.

In the delivery system according to an embodiment, wherein the exogenous cargo comprises an antibody or an antigen-binding antibody fragment thereof, an integrin or a fragment thereof, an immunogenic protein, a cytokine, a chemokine, a receptor protein or a fragment thereof, an enzyme, a cancer suppressor gene product, siRNA, microRNA, an antisense oligonucleotide (ASO), mRNA, DNA, a gene editing tool and/or a cytotoxic agent.

In the delivery system according to an embodiment, wherein the exogenous cargo comprises PAMP, DAMP, CD47, CD24, IL-12, IL-15, a coagulation factor VII, a coagulation factor VIII, a coagulation factor IX, and/or functionally active fragments thereof.

In the delivery system according to an embodiment, wherein the exogenous cargo incorporates into the migrasome, directly or indirectly, by gene editing, exogenous expression, liquid-solid conversion, membrane fusion, charge adsorption, physical adsorption, and/or chemical linkage.

In the delivery system according to an embodiment, wherein the exogenous cargo incorporates into or is intercalated to the migrasome by direct or indirect conjugation to a membrane component of the migrasome.

In the delivery system according to an embodiment, wherein the membrane component of the migrasome comprises a membrane protein, cholesterol, a phospholipid, a carbohydrate chain on a glycoprotein, and/or a polysaccharide.

In the delivery system according to an embodiment, wherein the indirect conjugation comprises linkage by a click chemical reaction.

In the delivery system according to an embodiment, wherein the indirect conjugation comprises providing the exogenous cargo to be conjugated to a first member of a binding pair, and bringing the exogenous cargo into contact with the migrasome, the membrane of the migrasome comprising a second member of the binding pair, wherein the first member is capable of binding to the second member.

In the delivery system according to an embodiment, wherein the first and second members of the binding pair are selected from antigens and antibodies thereof; receptors and ligands thereof; biotins and avidins; HaloTags and ligands thereof; and CP05s and CD63s.

In the delivery system according to an embodiment, wherein the exogenous cargo is expressed, as a membrane protein, on an inner or outer surface of the membrane of the migrasome.

In the delivery system according to an embodiment, wherein the exogenous cargo is expressed, as a fusion protein fused to a membrane protein or a moiety thereof, on the inner or outer surface of the membrane of the migrasome.

In the delivery system according to an embodiment, wherein the exogenous cargo is expressed, by gene editing and/or exogenous expression and as a fusion protein fused to a membrane protein or a moiety thereof, on the inner or outer surface of the membrane of the migrasome.

In another aspect, the present application provides a method for preparing a delivery system, comprising providing a migrasome, and allowing the migrasome to carry an exogenous cargo.

In the method according to an embodiment, wherein the migrasome is an isolated or purified migrasome.

In the method according to an embodiment, wherein the allowing the migrasome to carry the exogenous cargo comprises incorporating or intercalating the exogenous cargo to a membrane and/or an interior of the migrasome, directly or indirectly.

In the method according to an embodiment, wherein the method further comprises isolating or purifying the migrasome from a cell.

In the method according to an embodiment, wherein the method comprises providing a complex of the exogenous cargo and the first member of the binding pair; allowing a cell to produce a migrasome, which comprises a second member of the binding pair; and bringing the migrasome into contact with the complex to form the delivery system.

In the method according to an embodiment, wherein the migrasome comprises the migrasome of the present application.

In the method according to an embodiment, wherein the migrasome is derived from a cell.

In the method according to an embodiment, wherein the exogenous cargo comprises one or more targeting substances and/or therapeutically active substances.

In the method according to an embodiment, wherein the exogenous cargo comprises a protein, a lipid, a polynucleotide, a small molecule compound, a complex, a polysaccharide, a polymer, a nanoparticle, a microparticle and/or an organelle.

In the method according to an embodiment, wherein the exogenous cargo comprises a membrane protein, a soluble protein, and/or a polypeptide.

In the method according to an embodiment, wherein the exogenous cargo comprises DNA and/or RNA.

In the method according to an embodiment, wherein the exogenous cargo comprises an antibody or an antigen-binding antibody fragment thereof, an integrin or a fragment thereof, an immunogenic protein, a cytokine, a chemokine, a receptor protein or a fragment thereof, an enzyme, a cancer suppressor gene product, siRNA, microRNA, an antisense oligonucleotide (ASO), mRNA, DNA, a gene editing tool and/or a cytotoxic agent.

In the method according to an embodiment, wherein the exogenous cargo comprises PAMP, DAMP, CD47, CD24, IL-12, IL-15, a coagulation factor VII, a coagulation factor VIII, a coagulation factor IX, and/or functionally active fragments thereof.

In the method according to an embodiment, wherein the exogenous cargo incorporates into the migrasome, directly or indirectly, by gene editing, exogenous expression, liquid-solid conversion, membrane fusion, charge adsorption, physical adsorption, and/or chemical linkage.

In the method according to an embodiment, wherein the exogenous cargo is incorporated into or intercalated to the migrasome by direct or indirect conjugation to a membrane component of the migrasome.

In the method according to an embodiment, wherein the membrane component of the migrasome comprises a membrane protein, cholesterol, a phospholipid, a carbohydrate chain on a glycoprotein, and/or a polysaccharide.

In the method according to an embodiment, wherein the indirect conjugation comprises linkage by a click chemical reaction.

In the method according to an embodiment, wherein the indirect conjugation comprises providing the exogenous cargo to be conjugated to a first member of a binding pair, and bringing the exogenous cargo into contact with the migrasome, the membrane of the migrasome comprising a second member of the binding pair, wherein the first member is capable of binding to the second member.

In the method according to an embodiment, wherein the first and second members of the binding pair are selected from antigens and antibodies thereof; receptors and ligands thereof; biotins and avidins; HaloTags and ligands thereof and CP05s and CD63s.

In the method according to an embodiment, wherein the exogenous cargo is expressed, as a membrane protein, on an inner or outer surface of the membrane of the migrasome.

In the method according to an embodiment, wherein the exogenous cargo is expressed, as a fusion protein fused to a membrane protein or a moiety thereof, on the inner or outer surface of the membrane of the migrasome.

In another aspect, the present application provides a method for preparing a delivery system, comprising: allowing a cell to express mRNA; allowing the cell to produce a migrasome, which comprises an mRNA-binding protein; and linking the mRNA to the migrasome via the mRNA-binding protein.

In another aspect, the present application provides a method for preparing a delivery system, comprising: allowing a cell to express an exogenous cargo on a cytomembrane; and allowing the cell to produce a migrasome, which comprises the exogenous cargo.

In the method according to an embodiment, wherein the exogenous cargo is a protein.

In the method according to an embodiment, wherein the protein is a membrane protein.

In the method according to an embodiment, wherein the protein is a soluble protein, and is fused with a membrane protein or a moiety thereof to form a fusion protein.

In another aspect, the present application provides a composition, comprising the migrasome of the present application or the delivery system of the present application.

Other aspects and advantages of the present application can be readily perceived by those skilled in the art from the detailed description below. The detailed description below only illustrates and describes the exemplary embodiments of the present application. As would be appreciated by those skilled in the art, the content of the present application allows those killed in the art to change the specific embodiments disclosed without departing from the principal and scope involved in the present application. Accordingly, the accompanying drawings and the description in the specification of the present application are merely for an exemplary but not restrictive purpose.

BRIEF DESCRIPTION OF THE DRAWINGS

The specific features of the invention involved in the present application are listed in the appended claims. The characteristics and advantages of the invention involved in the present application may be better understood by referring to the exemplary embodiments and the accompanying drawings described in detail below. The accompanying drawings are briefly illustrated as follows:

FIGS. 1A-1C show effects of hypotonic stimulation on the formation of engineered migrasomes. FIG. 1A: formation of engineered migrasomes at different time points (scale: 5 μm) under hypotonic stimulation at 76.3 mOsmol/L; FIG. 1B: formation of engineered migrasomes at different osmotic pressures; and FIG. 1C: statistical results of the diameter of the engineered migrasomes presented in FIG. 1B.

FIG. 2B: statistical results of the number of the engineered migrasomes presented in FIG. 2A.

FIG. 3A: knockdown efficiency of Lrrc8a in cells as determined by qPCR; FIG. 3B: engineered migrasomes produced by stepwise hypotonic stimulation of cells with Lrrc8a knocked-down as observed using a laser confocal microscope; and FIG. 3C: statistical results of the diameter of the engineered migrasomes presented in FIG. 3B.

FIG. 4A: knockout of Lrrc8a in cells as determined by Western blotting; and FIG. 4B: engineered migrasomes produced by stepwise hypotonic stimulation of cells with Lrrc8a knocked-out as observed using a laser confocal microscope.

FIG. 5A: formation of engineered migrasomes with different cations in reaction solution; and FIG. 5B: statistical results of the diameter of the engineered migrasomes presented in a.

FIG. 6A a: formation of engineered migrasomes in the presence of overexpression of Tspan4; and FIG. 6B: statistical results of the number of the engineered migrasomes presented in a.

FIG. 7A: pictures of migrasomes produced by MGC803-T4-GFP cells in different culture dishes under different conditions, and FIG. 7B: quantification of cell detachment rate.

FIG. 8A: engineered migrasomes induced in different rodent cell lines; FIG. 8B: magnification of area selected from a (scale: 5 μm); FIG. 8C: engineered migrasomes induced in 2 T4-GFP-transfected human embryonic kidney cell strains/lines); and FIG. 8D: engineered migrasomes induced in different human cell lines, stained with WGA.

FIG. 11B. negative-staining transmission electron microscopic photographs of engineered migrasomes; and FIG. 11C. cryo-electron microscopic photographs of engineered migrasomes.

FIG. 13A: observations of engineered migrasomes by a laser confocal microscope; and FIG. 13B: statistical results of percentages of engineered migrasomes permeable to dextran-TMR after storage at room temperature for 1.5 h, 6 h, 12 h, 24 h, and 48 h.

FIGS. 14A-14C show stability of engineered migrasomes. FIG. 14A: morphological results of engineered migrasomes as observed by a laser confocal microscope on days 0, 1, 2, 3, 5, and 7; FIG. 14B: Western blotting analysis of chicken ovalbumin (OVA) and mCherry protein expression in purified engineered migrasomes after different days of storage at room temperature; and FIG. 14C: OVA-specific antibodies produced after immunizing mice with engineered migrasomes stored at room temperature for different days.

FIG. 24A: a schematic design of an animal experiment; FIG. 24B: Western blotting of S1 proteins in spike-expressed e-migrasomes, with a control e-migrasome group and a purified S1 protein as controls; and FIG. 24C: concentrations of spike(S) protein-specific IgGs in mouse serum after immunization by different methods.

FIG. 25A: observations of Tspan4-GFP-overexpressing NRK cells treated hypotonically and fixed with 2.5% glutaraldehyde, using a scanning electron microscope, with the scale of 20 μm on the left and 2 μm on the right; FIG. 25B: 4D photograph of engineered migrasomes produced by hypotonic treatment from Tspan4-GFP-overexpressing NRK cells using a spinning-disk confocal microscope, cell bodies expand with basal surfaces retracted to produce a large number of fiberous structures, and the engineered migrasomes are grown on these filamentous structures; FIG. 25C: electron microscopic photographs of A-431 cells producing hypotonic vesicles and micrographs of vesicles produced (References: Cohen S, Ushiro H, Stoscheck C, Chinkers M A native 170 000 epidermal growth factor receptor-kinase complex from shed plasma membrane vesicles. J Biol Chem 257: 1523-1531.).

FIGS. 26A-26H show comparison of migrasomes and engineered migrasomes (e-migrasomes). FIG. 26A on the left: observations of cultured and untreated TSPAN4-mCherry-expressing NRK cells by a confocal microscope, with the scale of 5 μm. FIG. 26B: observations of engineered migrasomes produced via hypotonic processes by Tspan4-GFP-expressing NRK cells, by a laser confocal microscope, with the scale of 5 μm; FIG. 26C: tetramethylrhodamine-labeled WGA-stained NRK cells overexpressing Tspan4-GFP, with upper photographs showing cells in an isotonic solution, and lower photographs showing cells after hypotonic treatment, where these photographs are Z-axis overlay photographs after scanning by a laser confocal microscope, with the scale of 5 μm; FIG. 26D: electron microscopic photographs of migrasomes (Ma et al, Cell Res. 2015); FIG. 26E: transmission electron microscopic images of engineered migrasomes produced by T4-GFP-overexpressing NRK cells, with the scale of 1 μm. FIG. 26F: comparison of mass spectrometry analysis of e-migrasomes and control migrasomes; FIG. 26G: 25 proteins that are not detected in engineered migrasomes but highly enriched in control migrasomes, with the numbers in the table representing Log 2 (change in expression fold relative to the cell bodies); experiment repeated 3 times; and FIG. 26H: engineered migrasomes (lower panels) exhibiting enrichment of the ERM family and a variety of other proteins, as compared to control migrasomes (upper panels), with left 3 panels acquired using Tspan-4-GFP imaging, Ezrin-mCherry imaging, and merged Z-stack images of the two, respectively, the second right panel being Fxyd5-mCherry imaging, and the first right panel being Atp1β1-mCherry imaging. (References: Ma L, Li Y, Peng J, Wu D, Zhao X, Cui Y, Chen L, Yan X, Du Y, Yu L. Discovery of the migrasome, an organelle mediating release of cytoplasmic contents during cell migration. Cell Res. 2015 January; 25(1):24-38. doi:

10.1038/cr.2014.135; Zhao X, Lei Y, Zheng J, Peng J, Li Y, Yu L, Chen Y. Identification of markers for migrasome detection. Cell Discov. 2019 May 21; 5:27. doi: 10.1038/s41421-019-0093-y. Erratum in: Cell Discov. 2022 Apr. 6; 8(1):32. PMID: 31123599; PMCID: PMC6527679.)

Figure 27A:
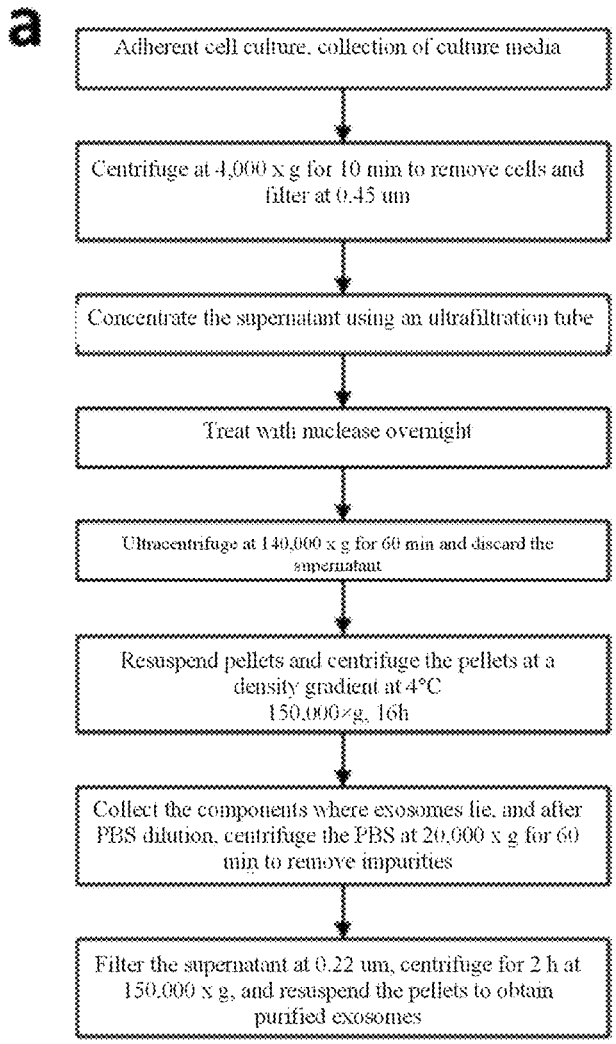
Figure 27B:
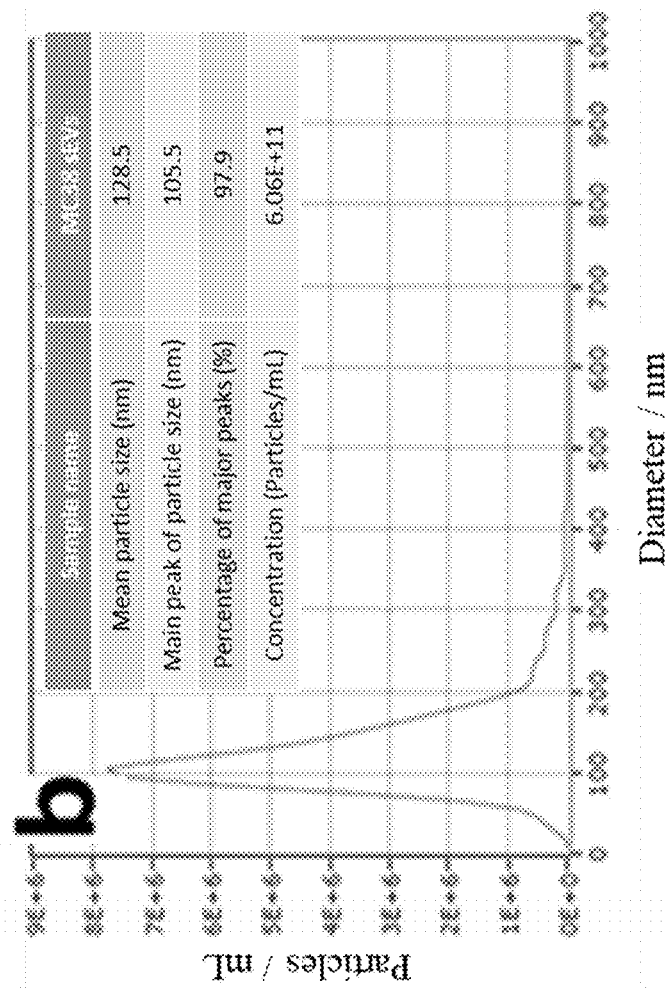
Figure 27C:
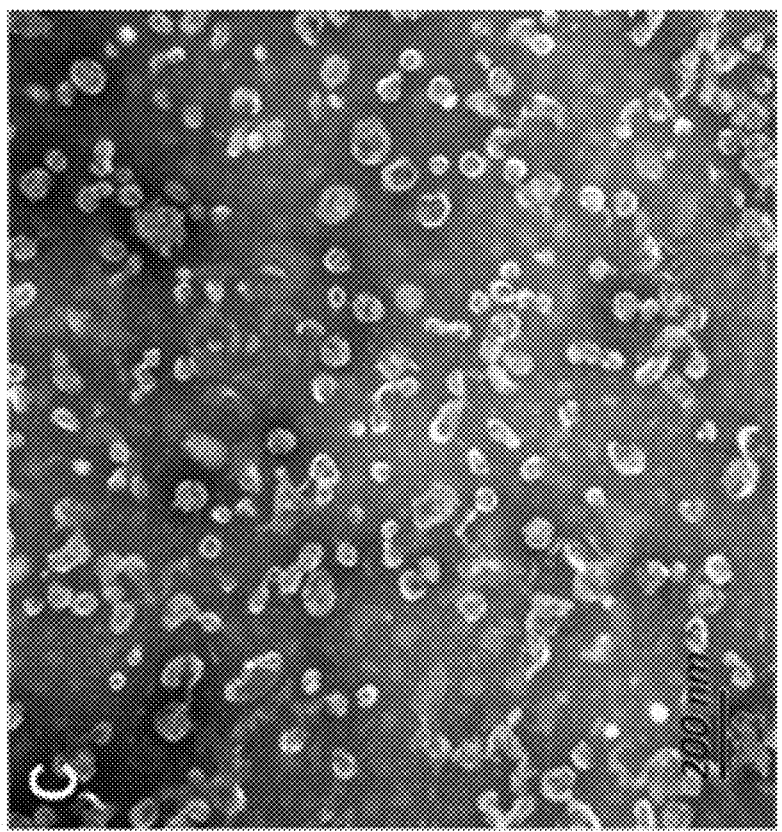
Figure 27D:
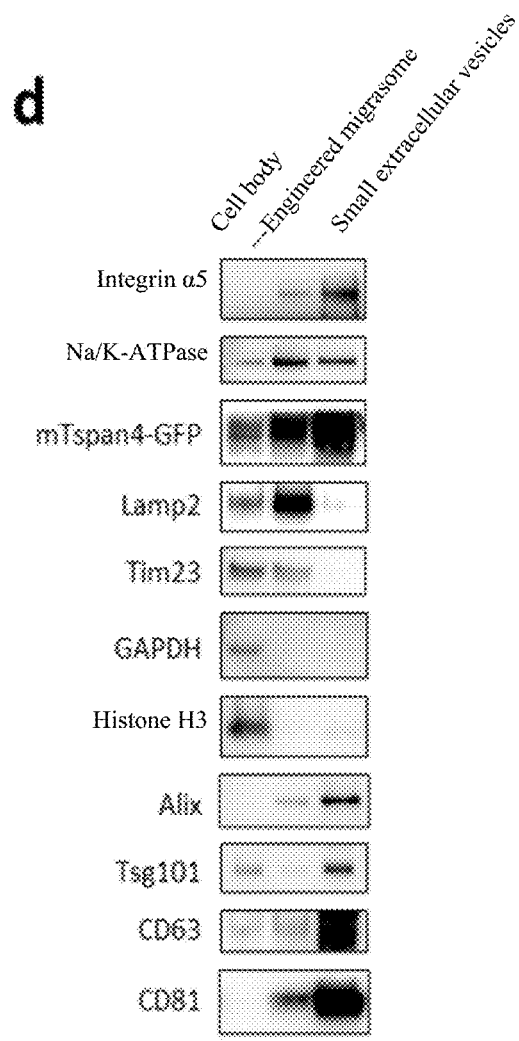

FIGS. 27a-27F show comparison of small vesicles/exosomes and engineered migrasomes, both of which are produced from Tspan4-GFP-overexpressing MC-38 cells. FIG. 27A: a small vesicle/exosome purification process; FIG. 27B: NTA examination of MC-38 small vesicles/exosomes after purification; FIG. 27C: examination of MC-38 small vesicles/exosomes by a transmission electron microscope (TEM); FIG. 27D: Western blotting analysis of small vesicles/exosomes, engineered migrasomes, and cell bodies, all of which are of the same cell origin; FIG. 27E: comparison of production and yield of small vesicles/exosomes and engineered migrasomes, both of which are of the same cell origin; and FIG. 27F: in vivo distribution, where fluorescence imaging is carried out on tissues taken at different times from small vesicles/exosomes or engineered migrasomes, which are produced by MC-38 cells expressing Tspan4-GFP and then subject to DiD labeling and intravenous injection with an equal fluorescent dye amount.

Figure 28A:
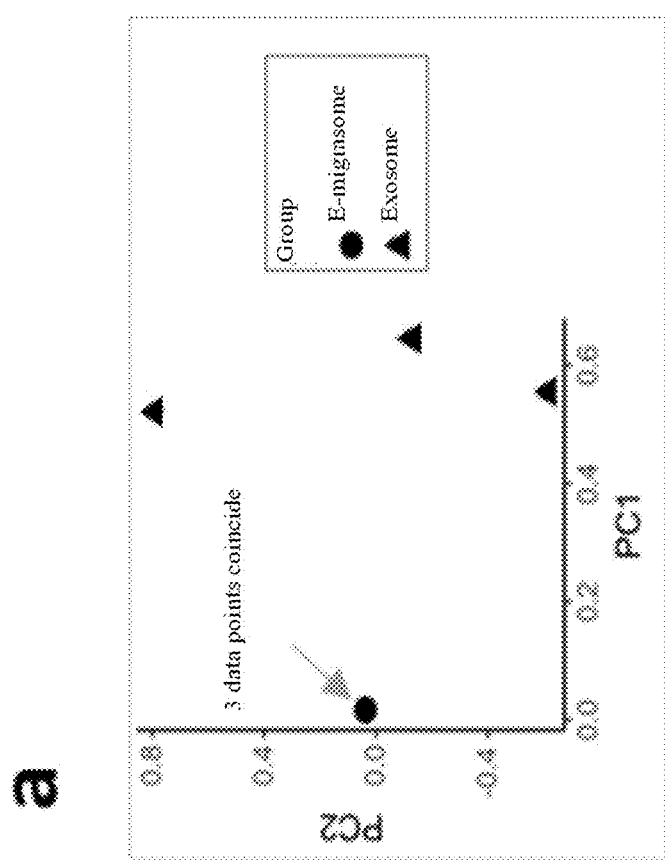
Figure 28B:
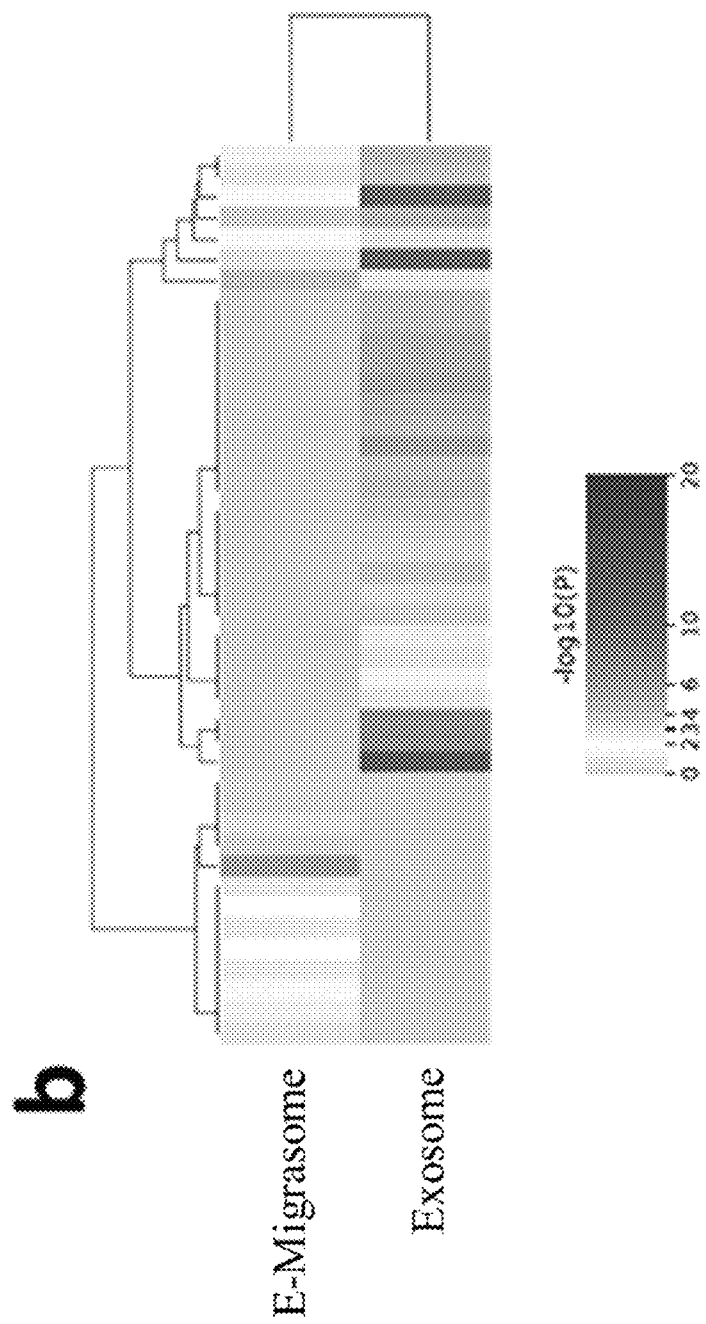

FIGS. 28A-28C show quantitative mass spectrometry of engineered migrasomes and small vesicles/exosomes, both of which are of the same cell origin. FIG. 28A: PCA analysis; FIG. 28B: heatmap of signal pathway analysis, note: the engineered migrasomes show high consistency within the three sets of data points which overlapped in the figure; and FIG. 28C: list of the 10 most enriched proteins of the prepared engineered migrasomes and small vesicles/exosomes, note: the engineered migrasomes show high consistency within three sets of data points, and the 10 most enriched proteins are identical.

DETAILED DESCRIPTION OF THE PREFERRED EMBODIMENTS

The embodiments of the invention of the present application will be illustrated by specific examples below. Those familiar with this technology can easily understand other advantages and effects of the invention of the present application from the disclosure of the specification.

Terms and Definitions

In the present application, the term "relative movement" generally refers to movement occurring relative to a reference point or reference plane. It refers to the movement of a cell center relative to an environment (e.g., a surface adhered thereto), or in the case of a stationary cell center, the relative movement of a cytomembrane surface relative to a surrounding microenvironment (e.g., a solid surface adhered thereto, or a liquid phase in the microenvironment) or relative to the cell center (e.g., expansion, bulging from flatness or the like).

In the present application, the term "migrasome" generally refers to a structure produced by a cell undergoing relative movement. For example, the migrasome may be a new type of organelle, for example, a vesicle structure produced at the tip or intersection of a retraction fiber that is left behind the cell during cell migration. For example, during cell migration, a cell body continuously sorts intracellular substances to the migrasome, and retraction fibers are subsequently broken and the migrasomes can be released locally or transported to distant tissues via body fluids such as blood and then taken up by cells in or around an extracellular space. For example, the migrasome may be involved in the transfer of intracellular material and signals between cells, thereby mediating intercellular communication.

In the present application, the term "membrane microdomain" generally refers to a region having a biomembrane structure. For example, cytomembrane microdomains based on sphingolipids and cholesterol (Ch) include lipid rafts, Tetraspanin-enriched microdomains (TEMs) or the like.

In the present application, the term "intraluminal vesicle" generally refers to a membranous vesicle (e.g., an organelle or a larger vesicle) that is formed or present in a lumen or in the space of a lumen or tubular structure. The lumen can also be used herein to describe an internal space of a cellular component or structure. For example, the intraluminal vesicle can be produced by an organelle. For example, the intraluminal vesicle may comprise an intraluminal vesicle in a migrasome, or an intraluminal vesicle that is not currently in a migrasome but is expected to be transported into a migrasome.

In the present application, the term "exogenous cargo" generally refers to a substance that does not naturally exist in a chromosome or a host cell. For example, the cell itself does not produce this substance, or does not produce (e.g., express) this substance in an equivalent amount. For example, the cell that produces this substance is distinguished from a natural cell, for example, in structure or function.

In the present application, the term "low osmolality" generally refers to the osmolality lower than the osmolality of an isotonic solution of cells. The isotonic solution refers to a solution having the osmolality equivalent to plasma osmolality.

In the present application, the term "cytoskeleton" generally refers to a protein fiber network system in cells, for example, a system composed of microtubules, microfilaments, and intermediate fibers.

In the present application, the term "Tetraspanin" generally refers to a tetratransmembrane protein superfamily comprising four transmembrane domains. These proteins can form the so-called tetratransmembrane protein-enriched microdomain (TEM) (Rubinstein, E. (2011). The complexity of tetraspanins. Biochem Soc Trans 39, 501-505.). TEM is about 100 nanometers in size and is rich in a range of proteins and lipid raft-like lipids such as cholesterol. During migrasome formation, many small TEMs aggregate to form a micron-scale macrodomain called a Tetraspanin-enriched membrane macrodomain (TEMA), the formation of which may be correlated with the growth of migrasomes on retraction fibers. For example, the Tetraspanin family may comprise 33 members, including Tspan1, Tspan2, Tspan3, Tspan4, Tspan5, Tspan6, Tspan7, Tspan8, Tspan9, Tspan10, Tspan11, Tspan12, Tspan13, Tspan14, Tspan15, Tspan16, Tspan17, Tspan18, Tspan19, Tspan20 (UPK1B), Tspan21 (UPK1A), Tspan22 (PRPH2), Tspan23 (ROM1), Tspan24 (CD151), Tspan25 (CD53), Tspan26 (CD37), Tspan27 (CD82), Tspan28 (CD81), Tspan29 (CD9), Tspan30 (CD63), Tspan31, Tspan32, and Tspan33. Data from biochemical studies and gene knockout mice suggest that these members of the Tetraspanin family play an important role in membrane biology.

In the present application, the terms "isolation" and "purification" are used interchangeably, and generally refer to identification, isolation and/or recovery of migrasomes from components in an environment where the migrasomes are produced, such that these "isolated or purified" migrasomes do not contain or substantially do not contain other contaminant components that are derived from the environment and may interfere with the therapeutic or diagnostic use of these migrasomes. The contaminant components may include abiotic substances (including chemical substances) or biological substances, for example, organelles, nucleic acids, proteins (e.g., soluble proteins), lipids, or metabolites. Hence, the "isolated or purified" migrasome may be prepared by at least one purification step that removes or substantially removes these contaminant components.

In the present application, the term "and/or" should be understood to mean either or both of optional items.

In the present application, the term "comprise" generally refers to the inclusion of explicitly specified features, but not excluding other elements.

In the present application, the term "about" generally refers to a variation within a range of 0.5%-10% above or below a specified value, for example, a variation within a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, and 10% above or below a specified value.

DETAILED DESCRIPTION OF THE INVENTION

In one aspect, the present application provides a method for preparing a migrasome. The method may comprise allowing a cell to move relatively and then produce a migrasome derived from the cell. For example, the relative movement in the present application may refer to the movement of a cell center relative to an environment (e.g., a surface adhered thereto), or in the case of a stationary cell center, the relative movement of a cytomembrane surface relative to a surrounding microenvironment (e.g., a solid surface adhered thereto, or a liquid phase in the microenvironment) or relative to the cell center (e.g., expansion, bulging from flatness or the like). For example, the occurrence and/or extent of the relative movement may be intervened by physical and/or chemical and/or biological means.

In the method according to an embodiment, the method may further comprise isolating the migrasome produced by the cell.

For example, the method of the present application may comprise carrying out hypotonic treatment on the cell, disrupting a cytoskeleton of the cell, suppressing a cell volume-regulatory function of the cell. detaching the cell from a surface adhered thereto, and/or allowing relative movement to occur between a cytomembrane of the cell and the surface adhered thereby, and may include increasing a number and/or function of a tetraspanin protein, a functional fragment thereof and/or a functional variant thereof in the cell.

For example, the method of the present application may comprise disrupting a cytoskeleton of the cell, suppressing a cell volume-regulatory function of the cell, detaching the cell from a surface adhered thereto, and/or allowing relative movement to occur between a cytomembrane of the cell and the surface adhered thereto, and may include increasing a number and/or function of a tetraspanin protein, a functional fragment thereof and/or a functional variant thereof in the cell. For example, the method of the present application may comprise carrying out hypotonic treatment on the cell, suppressing a cell volume-regulatory function of the cell, detaching the cell from a surface adhered thereto, and/or allowing relative movement to occur between a cytomembrane of the cell and the surface adhered thereto, and may include increasing a number and/or function of a tetraspanin protein, a functional fragment thereof and/or a functional variant thereof in the cell. For example, the method of the present application may comprise carrying out hypotonic treatment on the cell, disrupting a cytoskeleton of the cell, detaching the cell from a surface adhered thereto, and/or allowing relative movement to occur between a cytomembrane of the cell and the surface adhered thereby, and may include increasing a number and/or function of a tetraspanin protein, a functional fragment thereof and/or a functional variant thereof in the cell. For example, the method of the present application may comprise carrying out hypotonic treatment on the cell, disrupting a cytoskeleton of the cell, suppressing a cell volume-regulatory function of the cell, and/or allowing relative movement to occur between a cytomembrane of the cell and the surface adhered thereto, and may include increasing a number and/or function of a tetraspanin protein, a functional fragment thereof and/or a functional variant thereof in the cell. For example, the method of the present application may comprise carrying out hypotonic treatment on the cell, disrupting a cytoskeleton of the cell, suppressing a cell volume-regulatory function of the cell, and/or detaching the cell from a surface adhered thereto, and may include increasing a number and/or function of a tetraspanin protein, a functional fragment thereof and/or a functional variant thereof in the cell.

For example, the method of the present application may comprise suppressing a cell volume-regulatory function of the cell, detaching the cell from a surface adhered thereto, and/or allowing relative movement to occur between a cytomembrane of the cell and the surface adhered thereto, and may include increasing a number and/or function of a tetraspanin protein, a functional fragment thereof and/or a functional variant thereof in the cell. For example, the method of the present application may comprise carrying out hypotonic treatment on the cell, detaching the cell from a surface adhered thereto, and/or allowing relative movement to occur between a cytomembrane of the cell and the surface adhered thereto, and may include increasing a number and/or function of a tetraspanin protein, a functional fragment thereof and/or a functional variant thereof in the cell. For example, the method of the present application may comprise carrying out hypotonic treatment on the cell, disrupting a cytoskeleton of the cell, and/or suppressing a cell volume-regulatory function of the cell, and may include increasing a number and/or function of a tetraspanin protein, a functional fragment thereof and/or a functional variant thereof in the cell.

For example, the method of the present application may comprise carrying out hypotonic treatment on the cell, and/or allowing relative movement to occur between a cytomembrane of the cell and the surface adhered thereto, and may include increasing a number and/or function of a tetraspanin protein, a functional fragment thereof and/or a functional variant thereof in the cell. For example, the method of the present application may comprise disrupting a cytoskeleton of the cell, and/or allowing relative movement to occur between a cytomembrane of the cell and the surface adhered thereto, and may include increasing a number and/or function of a tetraspanin protein, a functional fragment thereof and/or a functional variant thereof in the cell. For example, the method of the present application may comprise suppressing a cell volume-regulatory function of the cell, and/or allowing relative movement to occur between a cytomembrane of the cell and the surface adhered thereto, and may include increasing a number and/or function of a tetraspanin protein, a functional fragment thereof and/or a functional variant thereof in the cell.

For example, in the method of the present application, the method may comprise carrying out hypotonic treatment on the cell.

For example, in the method of the present application, wherein the hypotonic treatment may comprise placing the cell in a hypotonic buffer solution.

For example, in the method of the present application, wherein the hypotonic treatment may comprise placing the cell in a buffer solution, and reducing the osmolality of the buffer solution to turn the buffer solution into the hypotonic buffer solution.

For example, in the method of the present application, wherein reducing may comprise linear reducing and/or step-wise reducing.

For example, in the method of the present application, wherein the osmolality of the hypotonic buffer solution may be less than about 305 mOsmol/L. For example, the osmolality of the hypotonic buffer solution may be less than about 305 mOsmol/L, less than about 300 mOsmol/L, less than about 270 mOsmol/L, less than about 250 mOsmol/L, less than about 200 mOsmol/L, less than about 150 mOsmol/L, less than about 100 mOsmol/L, less than about 90 mOsmol/L, less than about 80 mOsmol/L, less than about 70 mOsmol/L, less than about 60 mOsmol/L, less than about 50 mOsmol/L, less than about 40 mOsmol/L, less than about 30 mOsmol/L, less than about 20 mOsmol/L, less than about 15 mOsmol/L, less than about 10 mOsmol/L, less than about 5 mOsmol/L or less than about 2 mOsmol/L.

For example, in the method of the present application, wherein the osmolality of the hypotonic buffer solution may be about 10 mOsmol/L to about 274.5 mOsmol/L. For example, the osmolality of the hypotonic buffer solution may be about 10 mOsmol/L to about 300 mOsmol/L, about 20 mOsmol/L to about 300 mOsmol/L, about 30 mOsmol/L to about 300 mOsmol/L, about 50 mOsmol/L to about 300 mOsmol/L, about 70 mOsmol/L to about 300 mOsmol/L, about 100 mOsmol/L to about 300 mOsmol/L, about 150 mOsmol/L to about 300 mOsmol/L, about 200 mOsmol/L to about 300 mOsmol/L, about 250 mOsmol/L to about 300 mOsmol/L, about 10 mOsmol/L to about 250 mOsmol/L, about 20 mOsmol/L to about 250 mOsmol/L, about 30 mOsmol/L to about 250 mOsmol/L, about 50 mOsmol/L to about 250 mOsmol/L, about 70 mOsmol/L to about 250 mOsmol/L, about 100 mOsmol/L to about 250 mOsmol/L, about 150 mOsmol/L to about 250 mOsmol/L, about 200 mOsmol/L to about 250 mOsmol/L, about 10 mOsmol/L to about 200 mOsmol/L, about 20 mOsmol/L to about 200 mOsmol/L, about 30 mOsmol/L to about 200 mOsmol/L, about 50 mOsmol/L to about 200 mOsmol/L, about 70 mOsmol/L to about 200 mOsmol/L, about 100 mOsmol/L to about 200 mOsmol/L, about 150 mOsmol/L to about 200 mOsmol/L, about 10 mOsmol/L to about 150 mOsmol/L, about 20 mOsmol/L to about 150 mOsmol/L, about 30 mOsmol/L to about 150 mOsmol/L, about 50 mOsmol/L to about 150 mOsmol/L, about 70 mOsmol/L to about 150 mOsmol/L, about 100 mOsmol/L to about 150 mOsmol/L, about 10 mOsmol/L to about 100 mOsmol/L, about 20 mOsmol/L to about 100 mOsmol/L, about 30 mOsmol/L to about 100 mOsmol/L, about 50 mOsmol/L to about 100 mOsmol/L, about 70 mOsmol/L to about 100 mOsmol/L, about 10 mOsmol/L to about 30 mOsmol/L, about 20 mOsmol/L to about 30 mOsmol/L, about 30 mOsmol/L to about 90 mOsmol/L, or about 30 mOsmol/L to about 70 mOsmol/L. The hypotonic treatment comprises placing the cell in a buffer solution, and reducing the osmolality of the buffer solution to turn the buffer solution into the hypotonic buffer solution.

For example, in the method of the present application, the method may comprise disrupting a cytoskeleton of the cell.

For example, in the method of the present application, wherein disrupting the cytoskeleton of the cell may comprise bringing the cell into contact with a cytoskeleton-disrupting reagent. For example, in the method of the present application, wherein the cytoskeleton-disrupting reagent may comprise a microfilament and/or microtubule depolymerizing agent. For example, in the method of the present application, wherein the cytoskeleton-disrupting reagent may comprise Latrunculin A, Latrunculin B, cytochalasin A, cytochalasin B, cytochalasin C, cytochalasin D, and/or cytochalasin E.

For example, in the method of the present application, the method may comprise suppressing a cell volume-regulatory function of the cell.

For example, in the method of the present application, wherein suppressing the cell volume-regulatory function of the cell may comprise decreasing a number and/or function of a volume-regulatory protein in the cell. For example, with respect to an unmodified cell, suppressing the cell volume-regulatory function of the cell in the present application decreases the number and/or function of the volume-regulatory protein in the cell by about 5%, about 10%, about 20%, about 50%, or about 100%.

For example, in the method of the present application, wherein the volume-regulatory protein may comprise a volume-regulatory ion channel and/or a transporter. For example, in the method of the present application, wherein the volume-regulatory ion channel may comprise a volume-regulatory anion channel VRAC and/or a volume-regulatory cation channel VRCC. For example, in the method of the present application, wherein the volume-regulatory anion channel VRAC may comprise SWELL1 or a functionally active fragment thereof. For example, in the method of the present application, wherein the volume-regulatory cation channel VRCC may comprise TRPV4, TRPM3, and/or functionally active fragments thereof.

For example, in the method of the present application, wherein the transporter may comprise a cotransporter. For example, in the method of the present application, wherein the cotransporter may comprise KCC1, KCC3 and/or KCC4.

For example, in the method of the present application, wherein suppressing the cell volume-regulatory function of the cell may comprise placing the cell in a buffer solution that can inhibit volume regulatory ability of the cell. For example, in the method of the present application, wherein the buffer solution may comprise increased cations. For example, in the method of the present application, wherein the cations may comprise $K^+$, $Na^+$, $Cs^+$, $Li^+$, $Ca^{2+}$, $Mg^{2+}$, $Ba^{2+}$, $Mn^{2+}$, $Fe^{2+}$, $Ni^{2+}$, $Zn^{2+}$, $Al^{3+}$, $Fe^{3+}$, $CH_3NH_3^+$, $C_2H_5NH_3^+$, $(CH_3)_2NH_2^+$, $(C_2H_5)_2NH_2^+$, $(C_2H_5)_3N^+$, ammonia ions and/or choline ions.

For example, in the method of the present application, wherein the buffer solution may comprise increased anions. For example, in the method of the present application, wherein the anions may comprise $Br^-$, $Cl^-$, $I^-$, $F^-$, $OH^-$, $HCO_3^-$, $H_2PO_4^-$, $NO_2^-$, $NO_3^-$, $CN^-$, $HPO_4^{2-}$, $CO_3^{2-}$, $SO_4^{2-}$ and/or $PO_4^{3-}$.

For example, in the method of the present application, wherein the method may comprise detaching the cell from a surface adhered thereby.

For example, in the method of the present application, wherein the method may comprise allowing relative movement to occur between a cytomembrane of the cell and the surface adhered thereby.

For example, in the method of the present application, the method may further comprise increasing a number and/or function of a tetraspanin protein, a functional fragment thereof and/or a functional variant thereof in the cell. For example, in the method of the present application, the method may comprise allowing the cell to overexpress the tetraspanin protein, the functional fragment thereof and/or the functional variant thereof. For example, in the method of the present application, wherein the tetraspanin protein may be selected from: Tspan1, Tspan2, Tspan3, Tspan4, Tspan5, Tspan6, Tspan7, Tspan8, Tspan9, Tspan10, Tspan 11, Tspan12, Tspan13, Tspan14, Tspan15, Tspan16, Tspan17, Tspan18, Tspan19, Tspan20 (UPK1B), Tspan21 (UPK1A), Tspan22 (PRPH2), Tspan23 (ROM1), Tspan24 (CD151), Tspan25 (CD53), Tspan26 (CD37), Tspan27 (CD82), Tspan28 (CD81), Tspan29 (CD9), Tspan30 (CD63), Tspan31, Tspan32, and Tspan33.

For example, in the method of the present application, the method may further comprise reducing a size of the migrasome.

For example, in the method of the present application, wherein reducing the size of the migrasome may comprise extruding the migrasome with a filter or an extruder.

For example, in the method of the present application, wherein the filter or extruder may have a pore size of about 30 nm to about 10000 nm. For example, the filter or extruder may have a pore size of about 30 nm to about 100 nm, about 30 nm to about 1000 nm, about 30 nm to about 10000 nm, about 50 nm to about 100 nm, about 50 nm to about 1000 nm, about 50 nm to about 10000 nm, about 100 nm to about 1000 nm, about 100 nm to about 10000 nm, or about 1000 nm to about 10000 nm.

For example, in the method of the present application, wherein the migrasome may have a size of about 50 nm to about 8000 nm. For example, the migrasome may have a size of about 50 nm to about 100 nm, about 50 nm to about 1000 nm, about 50 nm to about 10000 nm, about 100 nm to about 1000 nm, about 100 nm to about 10000 nm, or about 1000 nm to about 10000 nm.

For example, in the method of the present application, wherein the migrasome may be generated from a retraction fiber of the cell.

For example, in the method of the present application, wherein a membrane of the migrasome may be enriched with sodium/potassium ATPase and/or a functional fragment thereof. For example, in the method of the present application, wherein the membrane of the migrasome may be enriched with an integrin and/or a functional fragment thereof. For example, in the method of the present application, wherein the membrane of the migrasome may be enriched with a tetraspanin protein, a functional variant thereof and/or a functional fragment thereof. For example, in the method of the present application, wherein the membrane of the migrasome may be enriched with cholesterol. For example, enrichment may refer to a condition as compared to other portions on the cytomembrane of a corresponding cell, or as compared to the condition of a corresponding cytomembrane before the production of the migrasome. For example, enrichment refers to the fact that the density of the molecules or substances on the migrasomes of the present application is higher than the density of the corresponding molecules or substances on the cytomembrane producing these migrasomes.

For example, in the method of the present application, wherein the migrasome may be enriched with a membrane microdomain. For example, the membrane microdomain refers to a cytomembrane microdomain based on sphingolipids and cholesterol (Ch), including lipid rafts, Tetraspanin-enriched microdomains (TEMs) or the like.

For example, in the method of the present application, wherein the migrasome may be produced in vitro or ex vivo.

For example, in the method of the present application, wherein the contents of the migrasome may be at least partially reduced or absent compared to a naturally occurring migrasome produced by the same cell. For example, in the case of engineered migrasomes produced by NRK cells, 4000 or more proteins are absent in migrasomes as compared to naturally occurring migrasomes, and engineered migrasomes have about 1350 proteins (i.e., extra proteins), for example AMP3, Myh4, Gorasp2, Asz1, Lats2, Scn2b, Pacsin1, and A1b, which are not found in the naturally occurring migrasomes. For example, the "naturally occurring migrasome" may refer to a migrasome produced by a spontaneously migrating cell without changing the external culture conditions (e.g., hypotonicity, temperature or the like); and the "engineered migrasome" may refer to a migrasome produced by a cell that undergoes relative movement induced by external stimulation.

For example, in the method of the present application, wherein the at least partially reduced contents may comprise an intraluminal vesicle. For example, the engineered migrasome provided by the present application has fewer intraluminal vesicles inside. The intraluminal vesicle may refer to a vesicle having a phospholipid bilayer structure in an outer membrane structure.

For example, in the method of the present application, the method may be an in vitro or ex vivo method. For example, the method for preparation in the present application may be carried out in vitro. For example, the method for preparation in the present application may not be carried out in a living object.

For example, in the method of the present application, wherein the cell may be a cell cultured in vitro.

For example, in the method of the present application, wherein the cell may be a cell cultured in suspension or cultured by adherence.

For example, in the method of the present application, wherein the cell may comprise a primary cell.

For example, in the method of the present application, wherein the primary cell may comprise a tissue cell derived from an organism, which may comprise a human, a monkey, a mouse, a rat, a rabbit, a chicken, and/or an insect.

For example, in the method of the present application, wherein the primary cell may comprise a liver cell, a spleen cell, a kidney cell, a tissue macrophage, a cerebral glial cell, an osteoclast, a bone marrow cell, a leukocyte, a fibroblast, and/or a fat cell. For example, the primary cell in the present application may comprise a Kupffer cell, for example, a type of phagocyte which is located on the inner surface of the hepatic sinuses and is capable of scavenging substances such as foreign antigens, antigen-antibody complexes, and cellular debris from the blood.

For example, in the method of the present application, wherein the leukocytes may comprise a B cell, a T cell, an NK cell, a dendritic cell, a neutrophil, and/or a macrophage.

For example, in the method of the present application, wherein the cell may comprise a tumor cell.

For example, in the method of the present application, wherein the tumor cell may comprise a tumor cell line, a primary or limited-passaged tumor cell derived from a patient, a tumor stromal cell, and/or a tumor organoid.

For example, in the method of the present application, wherein the cell may comprise a CHO cell, a CHO-K1 cell, an HEK293 cell, an HEK293T cell, an HEK293FT cell, an HEK293F cell, a Vero cell, a NRK cell, a L929 cell, a MC38 cell, a 4T1 cell, a DC2.4 cell, an MGC803 cell, a Jurkat cell, an NK-92MI cell, a BJ cell, and/or an HepG2 cell.

For example, in the method of the present application, wherein the cell may comprise a leukocyte, a stem cell, and/or a fibroblast.

For example, in the method of the present application, wherein the stem cell may comprise a mesenchymal stem cell.

For example, the present application provides a migrasome prepared in the method of the present application. For example, the present application provides a new extracellular vesicle, namely an engineered migrasome, which can be produced through engineering approaches, and/or a migrasome that is forcibly produced by a cell at high efficiency through engineering approaches, and/or a composition comprising any one of the above migrasomes. The engineered migrasome has a size of 50-8000 nanometers (nm), with a membrane enriched with proteins such as integrins and tetraspanin (Tspan) family members. In some cases, the engineered migrasome grows on a fiberous structure around the cell due to the existence of a membrane microdomain, and may be spontaneously released or artificially isolated from the cell to obtain a complete vesicle-like structure, and/or the biochemical composition, morphology and structure of the engineered migrasome are similar to those of a naturally occurring migrasome produced by the same cell. The engineered migrasome may also be specifically regulated according to application needs to obtain a vesicle-like structure that is greatly different from the naturally occurring migrasome of the cell in terms of structure and biochemical composition. For example, the present application provides the use of the migrasome/engineered migrasome as a drug-loaded delivery vector in the fields of therapies and vaccines for different diseases (e.g., tumors, inflammatory/autoimmune diseases, cardiovascular diseases, neurodegenerative diseases and other neurological diseases, etc.).

The migrasome is a newly discovered organelle, which is a single-layer membrane vesicle structure, with a diameter of 0.5-3 μm, produced at the tip or intersection of a retraction fiber left behind a cell during cell migration. For example, during cell migration, a cell body continuously sorts intracellular substances to the migrasome. Afterwards, retraction fibers are broken and the migrasomes can be released locally or transported to distant tissues via body fluids such as blood and then taken up by cells in or around an extracellular space. This suggests that the migrasome may be involved in the transfer of intracellular material and signals between cells, thereby mediating intercellular communication (Liang Ma et. al., Discovery of the migrasome, an organelle mediating release of cytoplasmic contents during cell migration, Cell Res (2015) 25:24-38).

Studies have shown that migrasomes play a crucial signaling role in embryonic development, immune responses, tumors, angiogenesis, tissue regeneration and other processes with active cell migration. Studies on migrasomes in zebrafish embryonic development have found that migrasomes, as membrane-coated vectors of signal molecules, determine the spatiotemporal distribution of signal molecules to thereby function to regulate organ development (Jiang D et. al., Migrasomes provide regional cues for organ morphogenesis during zebrafish gastrulation, Nat Cell Biol, 2019, 21(8):966-977). Migrasomes can mediate the intercellular transfer of proteins and mRNAs, which are transferred to recipient cells via migrasomes to thereby change the vital activities of the recipient cells (Zhu M et. al., Lateral transfer of mRNA and protein by migrasomes modifies the recipient cells, Cell Res, 2020, doi; 10.1038/s41422-020-00415-3). Migrasomes can regulate the quality of mitochondria by clearing out damaged mitochondria, thereby maintaining the homeostasis of mitochondria in cells (Jiang H et. al., Mitocytosis, a migrasome-mediated mitochondrial quality control process, Cell Press, doi:10.1016/j.cell.2021.04.027). Migrasomes have a regulatory effect on cancer cells in a tumor microenvironment. For example, in pancreatic cancer cells, the migrasomes can induce an inhibitory immune microenvironment to promote tumor growth (Zhang R H, A study of inter-regulatory effects of migrasomes in pancreatic cancer cells on phenotype and function of cancer cells and related immune cells in tumor microenvironment, 2020).

The detached migrasomes are a type of extracellular vesicle, showing many differences from known extracellular vesicles. For example, the differences between the detached migrasomes and exosomes lie in: 1) different structures: the migrasomes are attached to retraction fibers before being released and present a structure having small vesicles contained in a large vesicle, and the exosomes have no such a structure; 2) different sizes: the diameter of the exosomes is about 50-150 nm, while the diameter of the migrasomes is about 0.5-3 μm; 3) obviously different protein compositions: the migrasomes and the exosomes share only 27% of the protein composition, for example, NDST1 (bifunctional heparan sulfate N-deacetylase/N-sulfotransferase 1), PIGK (phosphatidylinositol glycan-anchored biosynthetic class K), CPQ (carboxypeptidase Q) and EOGT (EGF domain-specific O-linked N-acetylglucosamine transferase) are enriched on the migrasomes but not present in the exosomes (Zhao X, Lei Y, Zheng J, Peng J, Li Y, Yu L, Chen Y. Identification of markers for migrasome detection. Cell Discov. 2019 May 21; 5:27); and 4) completely different biogenesis processes due to regulations by different genetic pathways: the exosomes are initially produced as vesicles of multivesicular bodies (MVBs) and are released when the MVBs are fused with the plasma membranes, and the migrasomes are formed by the assembly of large domains on the plasma membranes (Huang Y, Zucker B, Zhang S, Elias S, Zhu Y, Chen H, Ding T, Li Y, Sun Y, Lou J, Kozlov M M*, Yu L*. Migrasome formation is mediated by assembly of micron-scale tetraspanin macrodomains. Nat Cell Biol. 2019 August; 21(8):991-1002).

Figure 1A:
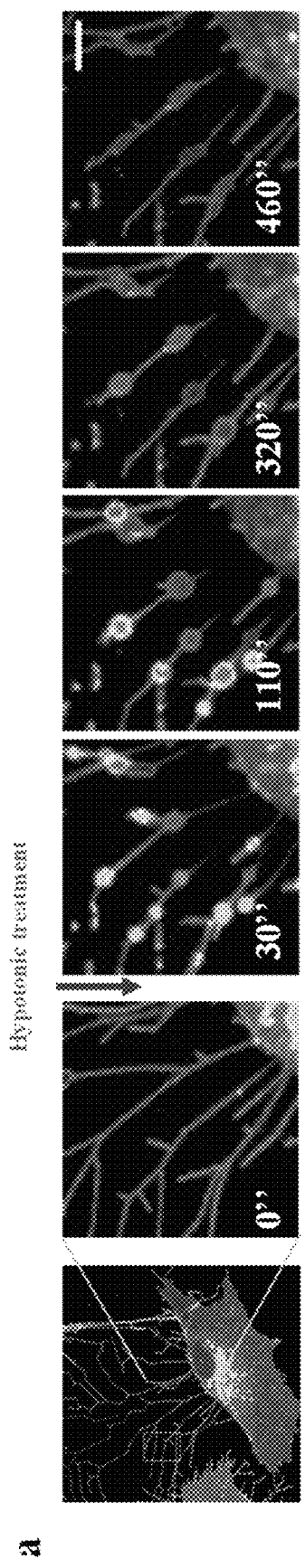
Figure 1B:
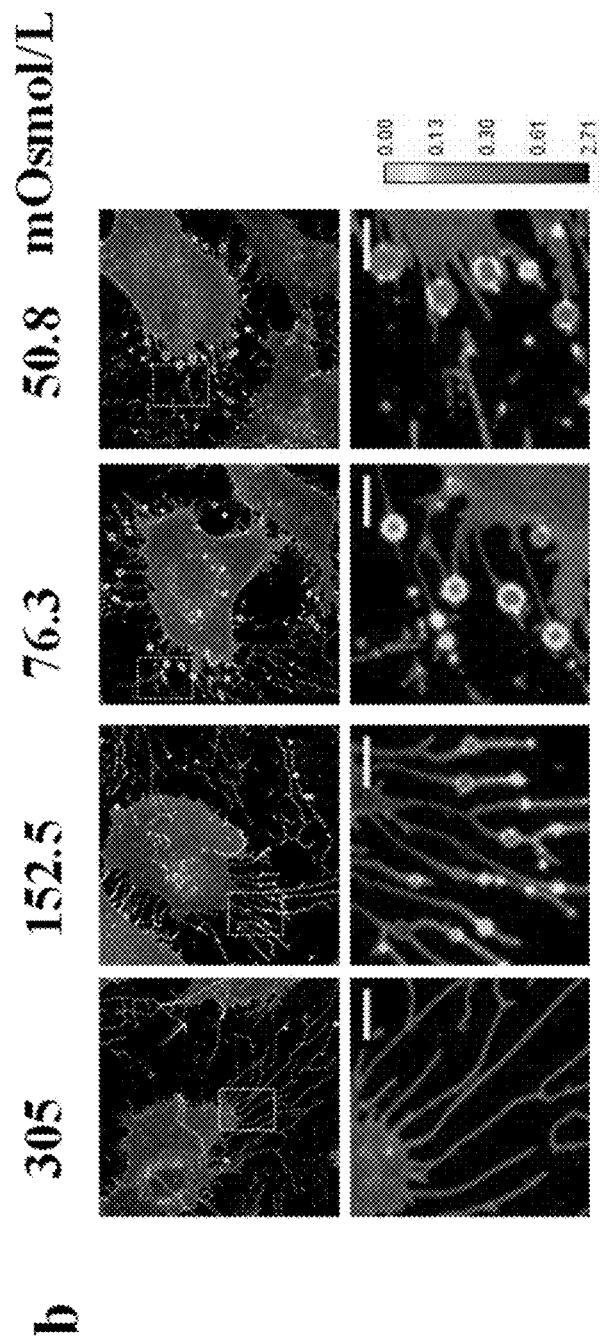

In the present application, it is found that the generation of engineered migrasomes similar in structure to natural migrasomes can be induced by a variety of methods. These engineered migrasomes are different from the "hypotonically induced vesicles" known in the art (e.g., the vesicles in Cohen S, Ushiro H, Stoscheck C, Chinkers M A native 170 000 epidermal growth factor receptor-kinase complex from shed plasma membrane vesicles. J Biol Chem 257: 1523-1531, as shown in FIG. 1). They have at least the following differences: 1) different vesicle production sites: the engineered migrasomes are produced on the retraction fibers around cells, while the vesicles are produced on the upper surfaces of cells according to Cohen et al.; 2) different vesicle sizes: the engineered migrasomes have a micron-level size and have a diameter that rarely exceeds 5 μm, while the vesicles induced by Cohen et al. using low osmolality can be as large as 20 μm; and 3) unlike the method of hypotonic induction according to Cohen et al., the hypotonicity in the present application may not be necessary for the production of engineered migrasomes, which can be induced by other methods.

At present, engineered extracellular vesicles have been widely applied to important biomedical fields such as drug delivery and vaccine preparation. For example, the engineered exosomes (Kamerkar S, LeBleu V S, Sugimoto H, Yang S, Ruivo C F, Melo S A, Lee J J, Kalluri R. Exosomes facilitate therapeutic targeting of oncogenic KRAS in pancreatic cancer. Nature. 2017 Jun. 22; 546(7659):498-503. doi: 10.1038/nature22341) have the following main advantages: natural biomembrane source, and low toxicity; low immunogenicity leading to low liability to be cleared by the immune system and longer internal circulation time; and stability in nature, allowing long-term storage at −80° C. However, they also show obvious limitations, for example, low yield; dependence on the ultracentrifuge during purification; nucleic acids loaded after purification as the main contents; or the like.

In the present application, it is found that the engineered migrasome is of a biological origin, which shares the advantages of low toxicity and low immunogenicity with the extracellular vesicle of the biological origin such as an exosome. The engineered migrasome is a newly discovered extracellular vesicle with unique characteristics in cargo types and biodistribution in vivo; and at the same time, the method for preparing the engineered migrasome is simple with high yield. In summary, the engineered migrasome discovered by the present application has great potential in biomedical fields such as drug delivery and vaccine preparation.

A method for preparing an engineered migrasome comprises: artificially inducing a cell to produce an engineered migrasome, and isolating and/or purifying the engineered migrasome; and/or forcing relative movement to occur between a cytomembrane and a culture environment (including a solid surface adhered thereto and a surrounding liquid environment). The migration includes, but is not limited to, natural cell migration patterns or relative movement of the cytomembrane relative to the environment at a sub-cellular scale.

In another aspect, the present application provides a migrasome prepared in vitro or ex vivo. The migrasome may have a size of about 50 nm to about 8000 nm.

For example, in the migrasome of the present application, the migrasome may be produced in vitro from a retraction fiber of a cell.

For example, in the migrasome of the present application, wherein a membrane of the migrasome may be enriched with sodium/potassium ATPase and/or a functional fragment thereof.

For example, in the migrasome of the present application, wherein the membrane of the migrasome may be enriched with an integrin and/or a functional fragment thereof.

For example, in the migrasome of the present application, wherein the membrane of the migrasome may be enriched with a tetraspanin protein, a functional variant thereof and/or a functional fragment thereof.

For example, in the migrasome of the present application, wherein the membrane of the migrasome may be enriched with cholesterol.

For example, in the migrasome of the present application, wherein the migrasome may be enriched with a membrane microdomain.

For example, in the migrasome of the present application, wherein the contents of the migrasome may be at least partially reduced or absent compared to a naturally occurring migrasome produced by the corresponding cell.

For example, in the migrasome of the present application, wherein the at least partially reduced contents may comprise an intraluminal vesicle.

In another aspect, the present application provides use of a migrasome in delivery of an exogenous cargo. For example, the "exogenous cargo" may refer to a substance that is not produced by the cell itself or is not produced (e.g., expressed) in an equivalent amount, or a substance that is, as the exogenous cargo, structurally or functionally different from the substance produced in the cell itself as described above the substance, even if this substance is produced in the cell itself.

For example, in the use of the present application, wherein the migrasome may comprise the migrasome of the present application.

In another aspect, the present application provides a delivery system, which may comprise a migrasome and one or more exogenous cargos.

For example, in the delivery system of the present application, wherein the exogenous cargo may be incorporated into, conjugated to or intercalated to a membrane and/or interior of the migrasome, directly or indirectly.

For example, in the delivery system of the present application, wherein the migrasome may comprise the migrasome of the present application.

For example, in the delivery system of the present application, wherein the migrasome may be derived from a cell.

For example, in the delivery system of the present application, wherein the exogenous cargo may comprise one or more targeting substances and/or therapeutically active substances.

For example, in the delivery system of the present application, wherein the exogenous cargo may comprise a protein, a lipid, a polynucleotide, a small molecule compound, a complex, a polysaccharide, a polymer, a nanoparticle, a microparticle and/or an organelle.

For example, in the delivery system of the present application, wherein the exogenous cargo may comprise a membrane protein, a soluble protein, and/or a polypeptide.

For example, in the delivery system of the present application, wherein the exogenous cargo may comprise DNA and/or RNA.

For example, in the delivery system of the present application, wherein the exogenous cargo may comprise an antibody or an antigen-binding antibody fragment thereof, an integrin or a fragment thereof, an immunogenic protein, a cytokine, a chemokine, a receptor protein or a fragment thereof, an enzyme, a cancer suppressor gene product, siRNA, microRNA, an antisense oligonucleotide (ASO), mRNA, DNA, a gene editing tool and/or a cytotoxic agent. For example, gene editing tools may include nucleases, for example Cas proteins, the CRISPR-Cas system, Cre recombinases, zinc finger endonucleases, transcription activator-like effector nucleases, and gene epigenetic editing tools.

For example, in the delivery system of the present application, wherein the exogenous cargo may comprise PAMP, DAMP, CD47, CD24, IL-12, IL-15, a coagulation factor VII, a coagulation factor VIII, a coagulation factor IX, and/or functionally active fragments thereof.

For example, in the delivery system of the present application, wherein the exogenous cargo may be incorporated into the migrasome, directly or indirectly, by gene editing, exogenous expression, liquid-solid conversion, membrane fusion, charge adsorption, physical adsorption, and/or chemical linkage. For example, the exogenous expression may comprise, for example, plasmid expression, for example, to establish a cell line with transient or stable overexpression of a gene.

For example, in the delivery system of the present application, wherein the exogenous cargo may be incorporated into or may be intercalated to the migrasome by direct or indirect conjugation to a membrane component of the migrasome.

For example, in the delivery system of the present application, wherein the membrane component of the migrasome may comprise a membrane protein, cholesterol, a phospholipid, a carbohydrate chain on a glycoprotein, and/or a polysaccharide.

For example, in the delivery system of the present application, wherein the indirect conjugation may comprise linkage by a click chemical reaction.

For example, in the delivery system of the present application, wherein the indirect conjugation may comprise providing the exogenous cargo to be conjugated to a first member of a binding pair, and bringing the exogenous cargo into contact with the migrasome, the membrane of the migrasome comprising a second member of the binding pair, wherein the first member is capable of binding to the second member.

For example, in the delivery system of the present application, wherein the first and second members of the binding pair may be selected from antigens and antibodies thereof, receptors and ligands thereof, biotins and avidins; HaloTags and ligands thereof; and CP05s and CD63s.

For example, in the delivery system of the present application, wherein the exogenous cargo may be expressed, as a membrane protein, on an inner or outer surface of the membrane of the migrasome. For example, in the delivery system of the present application, wherein the exogenous cargo may be expressed, as a fusion protein fused to a membrane protein or a moiety thereof, on the inner or outer surface of the membrane of the migrasome.

For example, in the delivery system of the present application, wherein the exogenous cargo may be expressed, by gene editing and/or exogenous expression and as a fusion protein fused to a membrane protein or a moiety thereof, on the inner or outer surface of the membrane of the migrasome.

In another aspect, the present application provides a method for preparing a delivery system. The method may comprise providing a migrasome, and allowing the migrasome to carry an exogenous cargo. For example, the exogenous cargo carried by the migrasome may comprise a reversibly linked exogenous cargo. For example, the exogenous cargo carried by the migrasome may comprise an irreversibly conjugated exogenous cargo.

For example, in the method of the present application, wherein the migrasome may be an isolated or purified migrasome.

For example, in the method of the present application, wherein allowing the migrasome to carry the exogenous cargo may comprise incorporating or intercalating the exogenous cargo to a membrane and/or an interior of the migrasome, directly or indirectly.

For example, in the method of the present application, the method may further comprise isolating or purifying the migrasome from a cell.

For example, in the method of the present application, the method may comprise providing a complex of the exogenous cargo and the first member of the binding pair; allowing a cell to produce a migrasome, which may comprise a second member of the binding pair; and bringing the migrasome into contact with the complex to form the delivery system.

For example, in the method of the present application, wherein the migrasome may comprise the migrasome of the present application.

For example, in the method of the present application, wherein the migrasome may be derived from a cell.

For example, in the method of the present application, wherein the exogenous cargo may comprise one or more targeting substances and/or therapeutically active substances.

For example, in the method of the present application, wherein the exogenous cargo may comprise a protein, a lipid, a polynucleotide, a small molecule compound, a complex, a polysaccharide, a polymer, a nanoparticle, a microparticle and/or an organelle.

For example, in the method of the present application, wherein the exogenous cargo may comprise a membrane protein, a soluble protein, and/or a polypeptide.

For example, in the method of the present application, wherein the exogenous cargo may comprise DNA and/or RNA.

For example, in the method of the present application, wherein the exogenous cargo may comprise an antibody or an antigen-binding antibody fragment thereof, an integrin or a fragment thereof, an immunogenic protein, a cytokine, a chemokine, a receptor protein or a fragment thereof, an enzyme, a cancer suppressor gene product, siRNA, microRNA, an antisense oligonucleotide (ASO), mRNA, DNA, a gene editing tool and/or a cytotoxic agent.

For example, in the method of the present application, wherein the exogenous cargo may comprise PAMP, DAMP, CD47, CD24, IL-12, IL-15, a coagulation factor VII, a coagulation factor VIII, a coagulation factor IX, and/or functionally active fragments thereof.

For example, in the method of the present application, wherein the exogenous cargo may be incorporated into the migrasome, directly or indirectly, by gene editing, exogenous expression, liquid-solid conversion, membrane fusion, charge adsorption, physical adsorption, and/or chemical linkage.

For example, in the method of the present application, wherein the exogenous cargo may be incorporated into or intercalated to the migrasome by direct or indirect conjugation to a membrane component of the migrasome.

For example, in the method of the present application, wherein the membrane component of the migrasome may comprise a membrane protein, cholesterol, a phospholipid, a carbohydrate chain on a glycoprotein, and/or a polysaccharide.

For example, in the method of the present application, wherein the indirect conjugation may comprise linkage by a click chemical reaction.

For example, in the method of the present application, wherein the indirect conjugation may comprise providing the exogenous cargo to be conjugated to a first member of a binding pair, and bringing the exogenous cargo into contact with the migrasome, the membrane of the migrasome comprising a second member of the binding pair, wherein the first member is capable of binding to the second member.

For example, in the method of the present application, wherein the first and second members of the binding pair may be selected from antigens and antibodies thereof, receptors and ligands thereof; biotins and avidins; HaloTags and ligands thereof; and CP05s and CD63s.

For example, in the method of the present application, wherein the exogenous cargo may be expressed, as a membrane protein, on an inner or outer surface of the membrane of the migrasome.

For example, in the method of the present application, wherein the exogenous cargo may be expressed, as a fusion protein fused to a membrane protein or a moiety thereof, on the inner or outer surface of the membrane of the migrasome.

In another aspect, the present application provides a method for preparing a delivery system, which may comprise: allowing a cell to express mRNA; allowing the cell to produce a migrasome, which may comprise an mRNA-binding protein; and linking the mRNA to the migrasome via the mRNA-binding protein. For example, an mRNA-binding protein may comprise a protein formation complex for binding the mRNA. For example, an RNA-binding protein comprises an RNA recognition motif. The RNA-binding protein has native or inactivated nuclease activity. The RNA-binding protein or its functional domains may comprise Cys2-His2, Gag-knuckle, Trebleclet, zinc ribbons, Zn2/Cys6-like motifs. An exemplary mRNA-binding protein may be included, but is not limited to, an RNA binding protein (RBP).

In another aspect, the present application provides a method for preparing a delivery system, which may comprise: allowing a cell to express an exogenous cargo on a cytomembrane; and allowing the cell to produce a migrasome, which may comprise the exogenous cargo. Expressing the exogenous cargo may be implemented by means of gene editing or exogenous expression, such as plasmid expression.

For example, in the method of the present application, wherein the exogenous cargo may be a protein.

For example, in the method of the present application, wherein the protein may be a membrane protein.

For example, in the method of the present application, wherein the protein may be a soluble protein, and may be fused with a membrane protein or a moiety thereof to form a fusion protein.

In another aspect, the present application provides a composition, which may comprise the migrasome of the present application or the delivery system of the present application.

1. A method for preparing an engineered migrasome comprises:
   (a) treating a cell with one or more of the following to induce the cell to produce an engineered migrasome:
   (1) hypotonic treatment;
   (2) disrupting the cytoskeleton of the cell;
   (3) suppressing a cell volume-regulatory function of the cell; and
   (4) allowing the cell to overexpress one or more proteins selected from members of the Tetraspanin family; and
   (5) inducing the cell for rapid detachment from a surface adhered thereto or inducing a cytomembrane to move relatively to the surface adhered thereto.
   (b) The engineered migrasome is isolated and/or purified.

2. The method according to technical solution 1, wherein in step (a), at least 1 treatment in (2)-(5) is carried out, or at least 2 treatments, at least 3 treatments, at least 4 treatments, or all 5 treatments in (1)-(5) are carried out.

3. The method according to technical solution 1 or 2, wherein step (a) comprises carrying out hypotonic treatment on the cell.

4. The method according to any one of technical solutions 1-3, wherein the hypotonic treatment is carried out by placing the cell in a hypotonic buffer solution, the osmolality of which is 30.5-274.5 mOsmol/L, for example, 30.5-150 mOsmol/L.

5. The method according to any one of technical solutions 1-3, wherein the hypotonic treatment is carried out by placing the cell in a buffer solution and reducing the osmolality of the buffer solution to 30.5-274.5 mOsmol/L, for example, 30.5-150 mOsmol/L.

6. The method according to technical solution 5, wherein reducing the osmolality of the buffer solution comprises linear reducing or stepwise reducing.

7. The method according to any one of technical solutions 1-6, wherein step (a) comprises disrupting a cytoskeleton of the cell.

8. The method according to technical solution 7, wherein the cytoskeleton of the cell is disrupted by bringing the cell into contact with a cytoskeleton-disrupting reagent.

9. The method according to technical solution 8, wherein the cytoskeleton-disrupting reagent comprises a microfilament depolymerizing agent, which is selected from, for example, Latrunculin A, Latrunculin B, cytochalasin A, cytochalasin B, cytochalasin C, cytochalasin D, and cytochalasin E.

10. The method according to any one of technical solutions 1-9, wherein step (a) comprises suppressing a cell volume-regulatory function of the cell.

11. The method according to technical solution 10, wherein the cell volume-regulatory function of the cell is suppressed by suppressing the expression or activity of a cell volume-regulatory protein in the cell.

12. The method according to technical solution 11, wherein the cell volume-regulatory protein is selected from an ion channel and a transporter.

13. The method according to technical solution 12, wherein the cell volume-regulatory protein is selected from a volume-regulatory anion channel (VRAC), for example SWELL 1; a volume-regulatory cation channel (VRCC), for example, TRPV4 and TRPM3; and a co-transporter such as KCC1, KCC3, and KCC4.

14. The method according to technical solution 10, wherein the cell volume-regulatory function of the cell is suppressed by placing the cell in a buffer solution containing cations or anions with a reduced ability to regulate changes in cell volume.

15. The method according to technical solution 14, wherein the cations are selected from one or more of $K^+$, $Na^+$, $Cs^+$, $Li^+$, $Ca^{2+}$, $Mg^{2+}$, $Ba^{2+}$, $Mn^{2+}$, $Fe^{2+}$, $Ni^{2+}$, $Zn^{2+}$, $Al^{3+}$, $Fe^{3+}$, $CH_3NH_3^+$, $C_2H_5NH_3^+$, $(CH_3)_2NH_2^+$, $(C_2H_5)_2NH_2^+$, $(C_2H_5)_3N^+$, ammonia ions and/or choline ions.

16. The method according to technical solution 14, wherein the anions are selected from one or more of $Br^-$, $Cl^-$, $F^-$, $OH^-$, $HCO_3^-$, $H2PO_4^-$, $NO_2^-$, $NO_3^-$, $CN^-$, $HPO_4^{2-}$, $CO_3^{2-}$, $SO_4^{2-}$ and/or $PO_4^{3-}$.

17. The method according to any one of technical solutions 1-16, wherein step (a) comprises allowing the cell to overexpress one or more proteins selected from members of the Tetraspanin family.

18. The method according to technical solution 17, wherein the members of the Tetraspanin family comprise Tspan1, Tspan2, Tspan3, Tspan4, Tspan5, Tspan6, Tspan7, Tspan8, Tspan9, Tspan10, Tspan11, Tspan12, Tspan13, Tspan14, Tspan15, Tspan16, Tspan17, Tspan18, Tspan19, Tspan20 (UPK1B), Tspan21 (UPK1A), Tspan22 (PRPH2), Tspan23 (ROM1), Tspan24 (CD151), Tspan25 (CD53), Tspan26 (CD37), Tspan27 (CD82), Tspan28 (CD81), Tspan29 (CD9), Tspan30 (CD63), Tspan31, Tspan32, and Tspan33.

19. The method according to technical solution 17, wherein step (a) comprises allowing the cell to overexpress Tspan4.

20. The method according to any one of technical solutions 1-19, further comprising reducing the size of the engineered migrasome.

21. The method according to technical solution 20, wherein the size of the engineered migrasome is reduced by using a filter of a specific pore size to extrude the engineered migrasome.

Optionally, the size of the reduced engineered migrasome is of nanoscale, for example 50-200 nm.

22. The method according to any one of technical solutions 1-21, wherein the cell is a normal cell or a cancer cell.

23. An engineered migrasome prepared by the method according to any one of technical solutions 1-22.

24. A delivery system, comprising an isolated or purified migrasome and a cargo, which is directly or indirectly incorporated into a membrane of the migrasome.

25. The delivery system according to technical solution 24, wherein the migrasome is selected from a naturally occurring migrasome and an artificially induced engineered migrasome.

26. The delivery system according to technical solution 25, wherein the engineered migrasome is produced by the method according to any one of technical solutions 1-22.

27. The delivery system according to any one of technical solutions 24-26, wherein the cargo is selected from proteins such as a membrane protein and a soluble protein, peptides, nucleic acids such as DNA and RNA, and small molecule compounds.

28. The delivery system according to any one of technical solutions 24-26, wherein the cargo is selected from therapeutic proteins, immunogenic proteins, cytokines, enzymes, siRNAs, microRNAs, antisense oligonucleotides (ASOs), mRNAs, CRISPR systems, cytotoxic agents, small therapeutic molecules, and targeting molecules.

29. The delivery system according to technical solution 28, wherein the targeting molecules are selected from: antibodies or antigen-binding fragments thereof; integrins; find-me/eat me signals, such as PAMPs and DAMPs; and don't-eat-me signals, such as CD47s and CD24s.

30. The delivery system according to any one of technical solutions 24-29, wherein the cargo is incorporated or intercalated to the membrane of the migrasome by physical adsorption or chemical linkage.

31. The delivery system according to any one of technical solutions 22-29, wherein the cargo is incorporated into or intercalated to the membrane of the migrasome in a manner selected from the group consisting of:
  (1) conjugating to a membrane component such as a membrane protein or cholesterol of the migrasome;
  (2) conjugating to a protein or peptide linked to the membrane of the migrasome, preferably by click chemistry; and
  (3) conjugating to a first member of a binding pair, wherein the membrane of the migrasome comprises a second member of the binding pair, and the cargo is linked to the membrane of the migrasome by the binding of the first member to the second member.

32. The delivery system according to technical solution 31, wherein the binding pair comprises a receptor-ligand binding pair.

33. The delivery system according to technical solution 32, wherein the binding pair comprises HaloTag and a ligand thereof, or CP05 and CD63.

34. The delivery system according to technical solution 31, wherein the cargo is mRNA, the membrane of the migrasome comprises an mRNA-binding protein, and the mRNA binds via a protein binding site 3'-UTR thereof to the mRNA-binding protein for conjugation to the membrane of the migrasome.

35. The delivery system according to any one of technical solutions 24-29, wherein the cargo is expressed, as a membrane protein, on the surface of the membrane of the migrasome.

36. The delivery system according to any one of technical solutions 24-29, wherein the cargo is expressed, as a fusion protein fused to a membrane protein or a moiety thereof, on the surface of the membrane of the migrasome.

37. A method for producing a delivery system comprising an isolated or purified migrasome and a cargo that is selected from the group consisting of a protein, a peptide, a nucleic acid (e.g., DNA and RNA) and a small molecular compound, wherein the method comprises:
  isolating or purifying a migrasome from a cell, the migrasome being a naturally occurring migrasome or an artificially induced engineered migrasome; and
  linking the cargo directly or indirectly to the membrane of the migrasome to thereby produce the delivery system.

38. The method according to technical solution 37, wherein the cargo is incorporated into the membrane of the migrasome by physical adsorption or chemical linkage.

39. The method according to technical solution 37, wherein the cargo is incorporated into the membrane of the migrasome in a manner selected from the group consisting of:
  (1) conjugating the cargo to a membrane component such as a membrane protein or cholesterol of the migrasome;
  (2) conjugating the cargo to a protein or peptide linked to the membrane of the migrasome, preferably by click chemistry.

40. A method for producing a delivery system comprising an engineered migrasome and a cargo that is selected from the group consisting of a protein, a peptide, a nucleic acid (e.g., DNA and RNA) and a small molecular compound, wherein the cargo is conjugated to a first member of a binding pair, and the membrane of the migrasome comprises a second member of the binding pair, wherein the method comprises:
  allowing the cell to express the second member of the binding pair on a cytomembrane;
  producing, by the cell, an engineered migrasome having a membrane comprising the second member of the binding pair; and
  bringing a complex of the cargo and the first member of the binding pair into contact with the engineered migrasome, to thereby product the delivery system by binding of the first member to the second member.

41. The method according to technical solution 40, wherein the binding pair comprises a receptor-ligand binding pair.

42. The method according to technical solution 41, wherein the binding pair comprises HaloTag and a ligand thereof, or CP05 and CD63.

43. A method for producing a delivery system comprising an engineered migrasome and a cargo, wherein the cargo is mRNA, a membrane of the migrasome comprises an mRNA-binding protein, and mRNA conjugates via a protein binding site 3'-UTR thereof to the mRNA-binding protein, wherein the method comprises:
  allowing the cell to express the mRNA,
  before, after, or at the same time as the above steps, allowing the cell to express the mRNA-binding protein on a cytomembrane; and producing, by the cell, the delivery system comprising the engineered migrasome and the mRNA, wherein the mRNA is conjugated to the membrane of the engineered migrasome by binding to the mRNA-binding protein.

44. A method for producing a delivery system comprising an engineered migrasome and a cargo, wherein the cargo is a protein and is expressed on a surface of a membrane of the engineered migrasome, wherein the method comprises:

allowing the cell to express the protein on the cell membrane; and producing, by the cell, the delivery system comprising the engineered migrasome and the protein expressed on the surface of the membrane of the engineered migrasome.

45. The method according to technical solution 44, wherein the protein is a membrane protein.

46. The method according to technical solution 44, wherein the protein is a soluble protein, and is expressed, as a fusion protein fused to a membrane protein or a moiety thereof, on the surface of the membrane of the migrasome.

47. The method according to any one of technical solutions 37-46, wherein the engineered migrasome is produced by the method according to any one of technical solutions 1-22.

Compared with a drug-conjugated delivery system and a non-bioderived drug delivery system, the migrasome delivery system of the present application shows better biocompatibility, more cargo types, larger capacity, and easier membrane modifications to enhance or alter targeting. Compared with an engineered exosome and an engineered red blood cell, the migrasome delivery system retains high biocompatibility and ease of modification, while migrasomes are larger than a traditional small vesicle (such as an exosome), such that drugs, in particular large-molecular-weight proteins and nucleic acids, can be delivered more efficiently. Meanwhile, the migrasome delivery system is highly amendable, and the size of the migrasome and substances loaded on the membrane can be adjusted according to the drug that needs to be delivered and the cells that need to be targeted. The migrasome also has the advantage of low toxicity, making it easier to transform and modify membrane components. In addition, the preparation of engineered migrasomes requires neither ultrahigh-speed centrifugation nor blood extraction each time, which greatly reduces the preparation time and cost.

Therefore, compared with the existing drug delivery system, the migrasome delivery system of the present application has the characteristics of low toxicity, high capacity, ease in modification, fast production, and low cost, has a unique antigen presentation effect due to adjustable antigenicity, and can be used as a vaccine delivery platform.

The present applicant found that a cell can be induced to produce an engineered migrasome by treating the cell with one or more of the following: carrying out hypotonic treatment; disrupting a cytoskeleton of the cell; suppressing a cell volume-regulatory function of the cell, and allowing the cell to overexpress a member of a Tetraspanin family; regulating relative movement of the cell by rapid detachment from a surface or a cytomembrane.

Although the migrasome has a vesicle structure, it differs from other extracellular vesicles including an exosome. The migrasome may not belong to extracellular vesicles in the strict sense. Although the migrasome detached from the cell is an extracellular vesicle, many functions of the migrasome are accomplished before its detachment from a cell body. This is why a migrasome is considered an organelle rather than only an extracellular vesicle. The production of an extracellular vesicle (detached migrasome) is only one of the numerous functions of the migrasome.

The detached migrasomes are a type of extracellular vesicle, showing many differences from exosomes as follows: for example, 1) different structures: the migrasomes are attached to retraction fibers before being released and present a structure having small vesicles contained in a large vesicle, and the exosomes have no such a structure; 2) different sizes: the diameter of the exosomes is about 50-150 nm, while the diameter of the migrasomes is about 0.5-3 μm; 3) obviously different protein compositions: the migrasomes and the exosomes share only 27% of the protein composition, for example, NDST1 (bifunctional heparan sulfate N-deacetylase/N-sulfotransferase 1), PIGK (phosphatidylinositol glycan-anchored biosynthetic class K), CPQ (carboxypeptidase Q) and EOGT (EGF domain-specific O-linked N-acetylglucosamine transferase) are enriched on the migrasomes but not present in the exosomes (Zhao X, Lei Y, Zheng J, Peng J, Li Y, Yu L, Chen Y. Identification of markers for migrasome detection. Cell Discov. 2019 May 21; 5:27); and 4) completely different biogenesis processes due to regulations by different genetic pathways: the exosomes are initially produced as vesicles of multivesicular bodies (MVBs) and are released when the MVBs are fused with the plasma membranes, and the migrasomes are formed by the assembly of large domains on the plasma membranes (Huang Y, Zucker B, Zhang S, Elias S, Zhu Y, Chen H, Ding T, Li Y, Sun Y, Lou J, Kozlov M M*, Yu L*. Migrasome formation is mediated by assembly of micron-scale tetraspanin macrodomains. Nat Cell Biol. 2019 August; 21(8):991-1002).

As used herein, the term "engineered migrasome" refers to an migrasome resulting from the engineered modification and/or artificial induction of a cell. It should be noted that the "engineered migrasome" may not imply that it is synthetic, but it is still cell-derived.

The engineered migrasomes of the present application may be different from the "hypotonically induced vesicles" known in the art (e.g., the vesicles in Cohen S, Ushiro H, Stoscheck C, Chinkers M A native 170 000 epidermal growth factor receptor-kinase complex from shed plasma membrane vesicles. J Biol Chem 257: 1523-1531, as shown in FIG. 1). They have at least the following differences: 1) different vesicle production sites: the engineered migrasomes are produced on the retraction fibers around cells, while the vesicles are produced on the upper surfaces of cells according to Cohen et al.; 2) different vesicle sizes: the engineered migrasomes have a micron-level size and have a diameter that rarely exceeds 5 μm, while the vesicles induced by Cohen et al. using low osmolality can be as large as 20 μm; and 3) unlike the method of hypotonic induction according to Cohen et al., the hypotonicity in the present application may not be necessary for the production of engineered migrasomes, and the cell can be detached rapidly by adjusting the adhesion characteristics of the cell, resulting in the relative movement of the cytomembrane on the surface adhered thereto, thereby inducing to produce the migrasome.

Unless otherwise expressly stated, the migrasome herein may comprise both naturally occurring migrasomes and artificially induced engineered migrasomes.

In some embodiments, the isolated or purified migrasome may not have detectable contaminant components, or the level or amount of contaminant components is equal to or lower than an acceptable level or quantity.

In some embodiments, the engineered migrasome may be isolated and/or purified by centrifugation. For example, the engineered migrasome may be isolated and/or purified by centrifugation at 300-17000×g. In some embodiments, the engineered migrasome may be isolated and/or purified by filtration.

The present applicant found that hypotonic treatment of cells can induce rapid and massive formation of micron-sized vesicles on the retraction fibers of cells. Such micron-sized vesicles are artificially induced engineered migrasomes. Therefore, in some embodiments of the method for preparing the engineered migrasome of the present application, inducing the cell to produce the engineered migrasome may comprise carrying out hypotonic treatment on the cell. In some embodiments, the hypotonic treatment may be carried out by placing a cell in a hypotonic buffer solution, the osmolality of which is 10%-90% of an isotonic buffer solution, for example, 15%-85%, 20%-80%, 25%-75%, 30%-70%, 35%-65%, 40%-60%, or 50%-55% of an isotonic buffer solution, or any value or subrange therebetween, for example, 10%, 11%, 12%, 13%, 14%, 15%, 16%, 17%, 18%, 19%, 20%, 30%, 40%, 50%, 60%, 70%, 80%, 90% of the isotonic buffer solution. In some other embodiments, the hypotonic treatment may be carried out by placing the cell in a buffer solution and reducing the osmolality of the buffer solution. In some embodiments, reducing the osmolality of the buffer solution comprises linear reducing or stepwise reducing. For example, in some embodiments, the salt concentration of the buffer solution may be stepwise reduced at predetermined intervals. For example, the salt concentration of the buffer solution may be stepwise reduced at least 3 times (for example, 3-5 times), by ⅙-½ each time.

The present applicant also found that disrupting the cytoskeleton allows cell contraction to cause cell edges to retract towards the center, while the cells adhere to various points at the bottom of a culture plate through adhesion plaques, thereby allowing plasma membranes to adhere in situ as anchors for membrane tether formation. The contraction of cells leads to the massive formation of membrane tethers on a region occupied by the cells before contraction, and these newly formed membrane tethers significantly enhance the formation of engineered migrasomes. Therefore, in some embodiments, inducing the cell to produce the engineered migrasome may comprise disrupting a cytoskeleton of the cell. In some embodiments, the cytoskeleton of the cell may be disrupted by bringing the cell into contact with a cytoskeleton-disrupting reagent. In some embodiments, the cytoskeleton-disrupting reagent comprises, for example, a microfilament or microtubule depolymerizing agent, which is selected from, for example, Latrunculin A, Latrunculin B, cytochalasin A, cytochalasin B, cytochalasin C, cytochalasin D, and cytochalasin E. In some embodiments, the cytoskeleton-disrupting reagent is Latrunculin A. In some embodiments, the concentration of the cytoskeleton-disrupting reagent may be any suitable concentration. For example, the concentration of a microfilament and/or microtubule depolymerizing agent may be at least 0.01 µM, at least 0.1 µM, at least 0.2 µM, at least 0.5 µM, at least 1 µM, at least 2 µM, at least 3 µM, at least 4 µM, at least 5 µM, at least 6 µM, at least 7 µM, at least 8 µM, at least 9 µM, or at least 10 µM.

The cells may withstand the changes of osmolality by means of their regulated volume changes. Therefore, suppressing the cell volume-regulatory function can promote the formation of engineered migrasomes. In some embodiments, inducing the cell to produce the engineered migrasome may comprise suppressing a cell volume-regulatory function of the cell. In some embodiments, the cell volume-regulatory function of the cell may be suppressed by suppressing the expression or activity of a cell volume-regulatory protein in the cell. For example, the cell volume-regulatory protein may be selected from an ion channel and a transporter. In some embodiments, the cell volume-regulatory protein may be selected from a volume-regulatory anion channel (VRAC), for example SWELL 1; a volume-regulatory cation channel (VRCC), for example, TRPV4 and TRPM3; and a co-transporter such as KCC1, KCC3, and KCC4. The expression or activity of proteins can be inhibited by any method or reagent known in the art, for example, disruption of protein-encoding gene sequences, RNAi, protein activity inhibitors, or the like.

It is known that cations and anions can regulate cell volume, but different ions have different abilities to regulate changes in cell volume. Therefore, ions with a weaker ability to regulate changes in cell volume also have a weaker ability to withstand changes in osmolality, such that the formation of migrasomes can be promoted. Therefore, in some embodiments, the cell volume-regulatory function of the cell may be suppressed by placing the cell in a buffer solution containing cations or anions with a reduced ability to regulate changes in cell volume. As used herein, the term "reduced ability to regulate changes in cell volume" is with respect to cations (e.g., sodium ions) or anions that endow cells with a normal cell volume regulatory ability.

In some embodiments, inducing the cell to produce the engineered migrasome may comprise allowing the cell to overexpress one or more proteins selected from key enzymes and structural proteins of the members of the Tetraspanin family or the migrasome production pathways, or carrying out stimulation with a migrasome-producing agonist. For example, the members of the Tetraspanin family may comprise Tspan1, Tspan2, Tspan3, Tspan4, Tspan5, Tspan6, Tspan7, Tspan8, Tspan9, Tspan10, Tspan11, Tspan12, Tspan13, Tspan14, Tspan15, Tspan16, Tspan17, Tspan18, Tspan19, Tspan20 (UPK1B), Tspan21 (UPK1A), Tspan22 (PRPH2), Tspan23 (ROM1), Tspan24 (CD151), Tspan25 (CD53), Tspan26 (CD37), Tspan27 (CD82), Tspan28 (CD81), Tspan29 (CD9), Tspan30 (CD63), Tspan31, Tspan32, and Tspan33. In some embodiments, the cell may be induced to produce the engineered migrasome by allowing the cell to overexpress one or more Tspan proteins.

In some embodiments, the migrasome may be induced by regulating the cell adhesion characteristics for rapid cell detachment, in order to reduce the contact area between the cell and a culture surface, or lead to relative movement between a cytomembrane and the surface. The cell may undergo hypotonic treatment at 4° C., 8° C., 16° C., 24° C., or 37° C., or without hypotonic treatment, and a cell detachment process may be carried out at 4° C., 8° C., 16° C., 24° C., or 37° C. Moreover, the cell body and the migrasome may be isolated.

In some embodiments, the method for preparing the engineered migrasome of the present application further comprises decreasing the size of the engineered migrasome. The size of the engineered migrasome may be reduced by any means known in the art, for example, by using a filter or extruder of a specific pore size to extrude the engineered migrasome. In some embodiments, the size of the engineered migrasome may be decreased by treating the engineered migrasome using an extruder having a filter membrane of a specific pore size. In some embodiments, the pore size of the filter membrane or extruder may be 30 nm-10000 nm, for example, 50 nm-8000 nm, 50 nm-1000 nm, 50 nm-10000 nm, 100 nm-1000 nm, 100 nm-10000 nm, 1000 nm-10000 nm, 10-400 nm, 20-300 nm, 30-200 nm, 40-100 nm, 50-80 nm or any value or subrange therebetween. In some embodiments, the size of the decreased engineered migrasome may be nanoscale, for example, 1-1000 nm, 10-900 nm, 20-300 nm, 30-200 nm, 40-100 nm, 50-80 nm or any value or subrange therebetween.

The cells used to produce the engineered migrasomes herein may be any cells, for example, cells cultured in vitro or cells in vivo; suspended or adherent cultured cell strains/lines in a suspended or adherent state with or without modifications, normal cells, primary cells, or disease-derived cells including cancer cells. In addition, the cells used to produce the engineered migrasomes may be derived from any cell line suitable for in vitro proliferation, modification and expression of exogenous molecules, and the production of engineered migrasomes. In some embodiments, the cell may be an animal cell, in particular a mammalian cell, including murine and human cells. Examples of suitable cells include, but are not limited to, normal rat kidney cells (NRK cells), mouse fibroblasts such as NIH3T3 cells, mouse breast cancer 4T1 cells, mouse colon cancer MC38 cells, commonly used human embryonic kidney (HEK) cell strains/lines such as HEK293 or HEK293FT cells, human gastric cancer MGC-803 cells, human T lymphocytoma Jurkat cells, human skin fibroblast BJ cells, Chinese hamster ovary (CHO) cells, mesenchymal stem cells (MSCs), or any other suitable cells.

As used herein, the term "cargo" may refer to any substance capable of being loaded on a migrasome and thus efficiently delivered. For example, the cargo may be delivered to a target cell by interaction between surface molecules of the migrasome and the target cell. One or more of the cargos of the present application may be loaded onto the membrane of the engineered migrasome during or after the formation of the engineered migrasome, or directly onto the membrane of a naturally occurring migrasome. Examples of the cargos include, but are not limited to, therapeutic agents, for example, synthetic bioactive compounds, natural bioactive compounds, antimicrobial compounds, antiviral compounds, proteins or peptides (e.g., enzymes or antibodies), nucleotides (e.g., nucleotides containing detectable moieties or toxins or nucleotides disrupting transcription), nucleic acids (e.g., DNA or mRNA molecules encoding peptides such as enzymes, pathogenic proteins, cytokines, cancer suppressor genes, antibodies, or the like, or RNA molecules with regulatory functions, such as microRNAs, dsDNA, antisense oligonucleotides (ASOs), lncRNAs and siRNAs), genome editing systems, lipids, carbohydrates, small molecules (e.g., small molecule drugs and toxins), targeting molecules, polysaccharides, complexes, organelles, nano- and micro-particles or any combination thereof.

In some embodiments, the cargo may be microRNA or siRNA, for example, microRNA or siRNA specifically binding to transcripts encoding mutated or non-mutated oncogenes. The binding of the microRNA or siRNA may inhibit mRNA decoding and protein synthesis. Such genes include, but are not limited to, ABLI, BLC1, BCL6, CBFA1, CBL, CSFIR, ERBA, ERBB, EBRB2, ETS1, ETS1, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, VEGF, FGF, G-CSF, CXCR4 or the like.

In some embodiments, the cargo may be a genome editing system. The genome editing systems include, but are not limited to, wide-range nuclease systems, zinc finger nuclease (ZFN) systems, transcription-like activator effector nuclease (TALEN) systems, and clustered regularly interspaced short palindromic repeats (CRISPR) systems. In some embodiments, the cargo may be a CRISPR system. In some embodiments, the CRISPR system may be a CRISPR-Cas9 system. The CRISPR-Cas9 systems include nucleotide sequences encoding Cas9 proteins, nucleotide sequences encoding CRISPR RNAs hybridized to target sequences (crRNA), and nucleotide sequences encoding trans-activated CRISPR RNAs (tracrRNAs). crRNAs and tracrRNAs can be fused into guide RNAs. The CRISPR-Cas9 systems may further comprise nuclear localization signals (NLSs). Migrasomes loaded with the CRISPR-Cas9 systems may be used to alter gene expression and function in disease management, regenerative medicine, and tissue engineering.

In some embodiments, the cargos may be therapeutic proteins or fragments thereof, such as antibodies or fragments thereof. In some embodiments, the cargos may be proteins (comprising antibodies or antibody fragments, immunogenic proteins, cytokines, enzymes, cancer suppressor gene products, or the like) or fragments thereof, for example, chicken ovalbumin (OVA), SARS-CoV-2 spike proteins or S1 fragments thereof.

In some embodiments, the cargo may be a targeting molecule. As used herein, the term "targeting molecule" refers to a molecule capable of specifically binding to another molecule (target molecule). For example, the targeting molecules may be used to specifically target a migrasome, presenting a targeting molecule on its surface, to an entity, for example, a tissue or cell expressing the target molecule, thereby improving the targeting of the delivery system. In some embodiments, the delivery system of the present application may comprise at least two different targeting molecules to further improve the targeting specificity or otherwise improve the targeting to the target cell or tissue. For example, the targeting molecule may specifically bind to a surface protein, for example, an antibody or an antigen-binding fragment thereof, which is overexpressed on a cancer cell. In some embodiments, the targeting molecules may be selected from: antibodies or antigen-binding fragments thereof; integrins; cytokines, chemokines and/or cytokines, chemokine receptors; polysaccharides; find-me/eat me signals, such as PAMPs and DAMPs; and don't-eat-me signals, such as CD47s and CD24s. In some embodiments, the antibody or the antigen-binding fragment thereof may bind to its corresponding antigen, thereby delivering the migrasome loaded with the antibody or the antigen-binding fragment thereof to the target cell expressing the corresponding antigen. In some embodiments, the integrins or other targeting molecules may be paired with tissue-specific extracellular matrixes, thereby achieving targeting of specific organs by the migrasome loaded with the integrins or other targeting molecules.

As used herein, the term "find-me/eat me signal" refers to a signal revealed or released by an apoptotic cell to trigger phagocytic uptake, which in turn activates a tolerance pathway to prevent immune responses to autoantigens. The find-me/eat me signal herein is loaded on the migrasome, and the find me/eat me signal can be recognized by a macrophage or the like, such that the migrasome is engulfed by a specific cell. Exemplary find-me/eat-me signals comprise, for example, pathogen-associated molecular patterns (PAMPs) and damage-associated molecular patterns (DAMPs). The "pathogen-associated molecular patterns (PAMPs)" refer to evolutionarily-conserved constant molecular structures, which are present on the surface of pathogenic microorganisms but not in some human hosts, and can be shared by many related microorganisms. The PAMP of innate immunological recognition is often the main part that the pathogen depends on for survival and therefore that changes less, for example, the double-stranded RNAs of viruses and the lipopolysaccharides of bacteria. For this, it is difficult for the pathogen to mutate and escape the action of innate immunity. The PAMP can be expressed on the surface of the pathogen or outside immune cells, or can be found in the cytosol of immune cells, as well as in various intracellular compartments (such as endosomes and phagolysosomes) carrying pathogens. There are two main categories of PAMP. The first category includes bacterial cell wall components dominated by saccharides and lipids, for examples, such as lipopolysaccharides, peptidoglycans, lipoteichoic acids, mannose, lipids, lipoarabinomannan, lipoproteins, flagelladin and the like. The most common and representative ones in this category include lipopolysaccharides (LPSs) produced by gram-negative bacteria; peptidoglycans produced by gram-positive bacteria; glycolipids produced by mycobacteria and mannose produced by yeast. The first category involves viral products and bacterial nucleus components, for example, non-methylated oligonucleotides CpGDNA, single-stranded RNAs, double-stranded RNAs. The "damage-associated molecular patterns (DAMPs)" are a class of substances released into an intercellular space or blood circulation after tissues or cells are stimulated by damage, hypoxia, stress, and other factors. They can induce autoimmunity or immune tolerance by means of pattern recognition receptors such as Toll-like receptors, RIG-1-like receptors or NOD-like receptors, and play an important role in the occurrence and development of diseases such as arthritis, atherosclerosis, tumors, systemic lupus erythematosus or the like. The DAMPs are present in cell nuclei, cytoplasm (e.g., high-mobility group protein box (HMGB)1, and S100 protein), extracellular matrixes (e.g., hyaluronic acid), and plasma (e.g., complements C3a, C4a, and C5a) or as foreign bodies (e.g., heat shock protein). The non-protein forms of DAMP comprise adenosine triphosphate, uric acid, heparin sulfate, RNA, and DNA. These proteins and non-proteins are confined inside cells in healthy conditions and released outside the cells when the cells are disrupted.

As used herein, the term "don't-eat-me signal" refers to a signal that is expressed by a tumor cell on its surface and binds to a ligand on the surface of an immune cell to inhibit the killing effect of the immune cell on tumor cells. The exemplary don't-eat-me signals comprise for example CD47 and CD24. The don't-eat-me signals herein are loaded on the migrasome by means of gene editing, membrane fusion or the like, such that the migrasome evades the clearance of the immune system to prolong its circulation time in the blood, thereby achieving better tissue infiltration.

For example, the migrasome may have a single-layer membrane structure with a membrane derived from a cytomembrane and intracellular vesicles. Compared with the cytomembrane, the membrane of migrasome is specifically enriched with some proteins (e.g., Tetraspanin) and lipids (e.g., cholesterol and sphingomyelin).

The cargo of the present application may be incorporated into or intercalated to the membrane and/or interior of the migrasome, directly or indirectly by any means known in the art.

In some embodiments, the cargo may be incorporated into or intercalated to the membrane and/or interior of the migrasome by liquid-solid conversion, membrane fusion, charge adsorption, physical adsorption, or chemical linkage.

In other embodiments, the cargo may be incorporated into or intercalated to the membrane and/or interior of the migrasome by means selected from the group consisting of: (1) conjugation to components, such as membrane proteins, cholesterol, phospholipids, and carbohydrate chains or polysaccharides on glycoproteins, in the membrane and/or interior of the migrasome; (2) conjugation to proteins or peptides, carbohydrate chains or polysaccharides on glycoproteins, phospholipids, cholesterol and the like that are incorporated into or intercalated to the membrane and/or interior of the migrasome, where the proteins or peptides, carbohydrate chains or polysaccharides on glycoproteins, phospholipids, cholesterol and the like are preferably incorporated into or intercalated to the membrane and/or interior of the migrasome by click chemistry; and (3) conjugation to a first member of a binding pair, where the membrane and/or interior of the migrasome comprises a second member of the binding pair, and the cargo is incorporated into or intercalated to the membrane and/or interior of the migrasome by binding of the first member to the second member.

In some embodiments, the cargo is incorporated into or intercalated to the membrane and/or interior of the migrasome by conjugating to components such as proteins or lipids in the membrane and/or interior of the migrasome. In some embodiments, the cargo is incorporated into or intercalated to the membrane and/or interior of the migrasome by linking to the membrane protein such as Tetraspanin in the migrasome. In some embodiments, the cargo is incorporated into or intercalated to the membrane and/or interior of the migrasome by conjugating to the Tetraspanin protein. In some embodiments, the cargo is incorporated into or intercalated to the membrane and/or interior of the migrasome by conjugating to lipids (e.g., cholesterol and sphingomyelin), proteins or peptides, or carbohydrate chains or polysaccharides on glycoproteins, in the membrane of the migrasome.

In some embodiments, the binding pair comprises antigen-antibody, receptor-ligand, biotin-avidin, HaloTag and its ligand, or other binding pairs. For example, the biding pair comprises HaloTag and a ligand thereof, or CP05 and CD63.

In some embodiments, the cargo is mRNA, and the membrane or interior of the migrasome comprises an mRNA-binding protein; and the mRNA is incorporated into or intercalated into the membrane and/or interior of the migrasome by binding of its protein-binding site to the mRNA-binding protein. The mRNA-binding protein and its protein-binding site may be those known in the art. For example, in some embodiments, the mRNA-binding protein is L7Ae, and the protein-binding site is a C/D Box. In some other embodiments, the mRNA-binding protein is MS2BP, and the protein-binding site is an MS2 step loop (MS2SL).

In some other embodiments, the cargo may be expressed, as a fusion protein, on the inner or outer surface of the membrane of the migrasome. In some other embodiments, the cargo may be expressed, as a fusion protein fused to a membrane protein or a moiety thereof, on the inner or outer surface of the membrane of the migrasome. Any membrane protein known in the art can be used as a membrane-anchored protein to be fused with a soluble protein. Examples of the membrane protein for fusion as a soluble protein include, but are not limited to, cell receptors, ion channels, transporters or the like, for example, Tspan-4, CD81, CD9, CD63, PDGFR, Lamp2b, syntaxin 2 (STX2), or the like. In some embodiments, the membrane protein for fusion as a soluble protein may be STX2. In some embodiments, the membrane protein for fusion as a soluble protein may be truncated STX2 (t-STX2). For example, the N-terminus of STX2 may be modified to remove its intracellular terminal function to obtain t-STX2. Then, the soluble protein can be linked to the extracellular C-terminus of t-STX2 to form a soluble protein-t-STX2 fusion protein, allowing the soluble protein to be expressed on the membrane of the migrasome as an artificial plasma membrane localization fusion protein.

In another aspect, the present application relates to a method for producing a delivery system, which comprises an isolated or purified migrasome and a cargo, wherein the cargo is selected from the group consisting of a protein, a peptide, a nucleic acid (e.g., DNA and RNA), a lipid, a small molecule compound, a polysaccharide, a complex, a nano/micron particle, and an organelle, or more than one of the aforesaid cargos are simultaneously loaded, and wherein the method comprises: isolating or purifying a migrasome from a cell, the migrasome being a naturally occurring migrasome or an artificially induced engineered migrasome; and incorporating or intercalating the cargo to a membrane and/or interior of the migrasome, directly or indirectly. In some embodiments of the method for producing the delivery system of the present application, the cargo is incorporated into or intercalated to the membrane and/or interior of the migrasome by liquid-solid conversion, membrane fusion, charge adsorption, physical adsorption, or chemical linkage.

In some other embodiments of the method for producing the delivery system of the present application, the cargo is incorporated into or intercalated to the membrane and/or interior of the migrasome by means selected from the group consisting of: (1) conjugation of the cargo to components, such as membrane proteins, cholesterol, phospholipids, and carbohydrate chains or polysaccharides on glycoproteins, in the membrane and/or interior of the migrasome; and (2) conjugation of the cargo to proteins or peptides, carbohydrate chains or polysaccharides on glycoproteins, phospholipids, cholesterol and the like that are linked to the membrane and/or interior of the migrasome, where the proteins or peptides, carbohydrate chains or polysaccharides on glycoproteins, phospholipids, cholesterol and the like are preferably incorporated or intercalated to the membrane and/or interior of the migrasome by click chemistry.

In some embodiments, the naturally occurring migrasome may be isolated or purified from a cell by methods known in the art. In some embodiments, the artificially induced engineered migrasome is produced by the method for preparing the engineered migrasome disclosed herein. In some embodiments, the cargo may be one or more of the cargos described elsewhere herein.

In another aspect, the present application relates to a method for producing a delivery system, which comprises an engineered migrasome and a cargo that is selected from the group consisting of a protein, a peptide, a nucleic acid (e.g., DNA and RNA), a lipid, a small molecule compound, a polysaccharide, a complex, a nano/micron particle, and an organelle, or more than one of the aforesaid cargos are simultaneously loaded, wherein the cargo is conjugated to a first member of a binding pair, and the membrane or interior of the migrasome comprises a second member of the binding pair, and wherein the method comprises: allowing the cell to express the second member of the binding pair on a cytomembrane; producing, by the cell, an engineered migrasome having a membrane comprising the second member of the binding pair; and bringing a complex of the cargo and the first member of the binding pair into contact with the engineered migrasome, to thereby product the delivery system by binding of the first member to the second member.

In some embodiments of the method for producing the delivery system of the present application, the method comprises introducing to a cell a nucleotide sequence containing an encoding sequence of a second member of a binding pair to allow the cell to express the second member of the binding pair. In some embodiments, the method comprises introducing to a cell a nucleotide sequence containing a encoding sequence of a second member of a binding pair, and culturing the cell under conditions allowing the cell to express the second member of the binding pair, such that the cell expresses the second member of the binding pair on the cell membrane.

In some embodiments, the method comprises: a) introducing to a cell a nucleotide sequence containing a encoding sequence of a second member of a binding pair; b) culturing the cell under conditions allowing the cell to express the second member of the binding pair; c) producing by the cell an engineered migrasome containing the second member of the binding pair on a membrane; d) conjugating a cargo to a first member of the binding pair to form a complex; and e) bringing the engineered migrasome into contact with the complex to produce the delivery system. In some embodiments, the above step d) is carried out before, after or at the same time as step a).

In some embodiments, the second member of the binding pair is a membrane protein or a soluble protein. In some embodiments, the second member of the binding pair is a membrane protein, and is expressed on the inner or outer surface of the membrane of the migrasome. In some embodiments, the second member of the binding pair is a soluble protein, and is expressed, as a fusion protein fused to a membrane protein or a moiety thereof, on the inner or outer surface of the membrane of the migrasome.

In some embodiments, the binding pair comprises antigen-antibody, receptor-ligand, biotin-avidin, HaloTag and its ligand, or other binding pairs. In some embodiments, the binding pair comprises HaloTag and a ligand thereof, or CP05 and CD63.

In some embodiments, the engineered migrasome is produced by the method for preparing the engineered migrasome disclosed herein. In some embodiments, the cargo may be one or more of the cargos described elsewhere herein.

In still another aspect, the present application relates to a method for producing a delivery system, which comprises an engineered migrasome and a cargo, wherein the cargo is mRNA, the membrane or interior of the migrasome comprises an mRNA-binding protein, and the mRNA binds via its protein binding site to the mRNA-binding protein, and wherein the method comprises: allowing the cell to express the mRNA; before, after, or at the same time as the above steps, allowing the cell to express the mRNA-binding protein on a cytomembrane; and producing, by the cell, the delivery system comprising the engineered migrasome and the mRNA, wherein the mRNA is linked to the membrane and/or interior of the engineered migrasome by binding to the mRNA-binding protein.

In some embodiments of the method for producing the delivery system of the present application, the method comprises introducing to a cell a sequence encoding an mRNA containing a protein-binding site to allow the cell to express the mRNA.

In some embodiments, the method comprises introducing to a cell a nucleotide sequence containing a sequence encoding an mRNA-binding protein to allow the cell to express the mRNA-binding protein on a cytomembrane of the cell.

In some embodiments, the method comprises introducing to a cell a nucleotide sequence containing a sequence encoding of an mRNA containing a protein-binding site and a sequence encoding an mRNA-binding protein, to allow the cell to express the mRNA and the mRNA-binding protein.

In some embodiments, the mRNA-binding protein is a membrane protein or a soluble protein. In some other embodiments, the mRNA-binding protein is a membrane protein, and is expressed on the inner or outer surface of the membrane of the migrasome. In some other embodiments, the mRNA-binding protein is a soluble protein, and is expressed, as a fusion protein fused to a membrane protein or a moiety thereof, on the inner or outer surface of the membrane of the migrasome.

The mRNA-binding protein and its protein-binding site may be those known in the art. For example, in some embodiments, the mRNA-binding protein is L7Ae, and the protein-binding site is a C/D Box. In some other embodiments, the mRNA-binding protein is MS2BP, and the protein-binding site is an MS2 step loop (MS2SL).

In some embodiments, the engineered migrasome is produced by the method for preparing the engineered migrasome disclosed herein.

In another aspect, the present application relates to a method for producing a delivery system comprising an engineered migrasome and a cargo, wherein the cargo is a protein and is expressed on an inner or outer surface of a membrane of the engineered migrasome, and wherein the method comprises: allowing the cell to express the protein on the cell membrane; and producing, by the cell, the delivery system comprising the engineered migrasome and the protein expressed on the inner or outer surface of the membrane of the engineered migrasome.

In some embodiments, the method comprises introducing to a cell a nucleotide sequence containing a protein-encoding sequence, to allow the cell to express the protein on a cytomembrane of the cell. In some embodiments, the method comprises introducing to a cell a nucleotide sequence containing a protein-encoding sequence, and culturing the cell under conditions allowing the cell to express the protein, such that the cell expresses the protein on a cytomembrane.

In some embodiments, the method comprises: introducing to a cell a nucleotide sequence containing an encoding sequence of a protein of interest; culturing the cell under conditions allowing the cell to express the protein of interest; and producing by the cell a delivery system containing an engineered migrasome and the protein expressed on the inner or outer surface of a membrane of the engineered migrasome.

In some embodiments, the protein may be a membrane protein. In some other embodiments, the protein is a soluble protein, and is expressed, as a fusion protein fused to a membrane protein or a moiety thereof, on the surface of the membrane of the migrasome.

As described above, examples of the membrane protein for fusion as a soluble protein include, but are not limited to, cell receptors, ion channels, transporters or the like, for example, Tspan-4, CD81, CD9, CD63, PDGFR, Lamp2b, syntaxin 2 (STX2), or the like.

In some embodiments, the engineered migrasome is produced by the method for preparing the engineered migrasome disclosed herein.

The present application further provides a pharmaceutical composition or diagnostic composition comprising the engineered migrasome of the present application, and one or more pharmaceutically acceptable excipients, diluents, or carrier combinations. Accordingly, the present application further provides use of the engineered migrasome of the present application in the preparation of pharmaceutical compositions.

The present application further provides a method for preparing a medicament or diagnostic composition. The method comprises adding and mixing the engineered migrasome of the present application together with one or more pharmaceutically acceptable excipients, diluents or carriers.

The engineered migrasome may be used as the only active ingredient in the drug or diagnostic composition, and may also be accompanied by other active ingredients such as steroids or other drug molecules. The composition may be administered individually to a patient or may be administered in combination with other agents, medicaments, or hormones (e.g., simultaneously, sequentially or separately).

The pharmaceutical composition may comprise a therapeutically effective amount of the engineered migrasome of the present application. In the present application, the term "therapeutically effective amount" refers to the amount of a therapeutic agent necessary for treating, ameliorating or preventing a targeted disease or condition or for exhibiting a detectable therapeutic or preventive effect. For any publicly available engineered migrasome, the therapeutically effective amount can be estimated initially in cell culture assays or in animal models, typically in rodents, rabbits, dogs, pigs, or primates. The animal models may also be used to determine the appropriate concentration range and route for administration. The information may subsequently be used to determine the dose and route appropriate for an administered person. The precise therapeutically effective amount for human subjects will be determined depending on the severity of a disease or condition, the overall health of a subject, the age, weight and gender of the subject, diet, timing and frequency of administration, drug combination, response sensitivity, and tolerability/response to a therapy.

The pharmaceutical composition of the present application may be administered by a variety of routes, including but not limited to oral, intravenous, intramuscular, intraarterial, intramedullary, intrathecal, intracompartment, transdermal, percutaneous, subcutaneous, intraperitoneal, intranasal, transenteral, topical, sublingual, intravaginal or rectal routes. A needle-free syringe may also be used to administer the pharmaceutical composition of the present application. Generally, the therapeutic composition may be prepared into an injectable agent as a liquid solution or suspension. Solid forms suitable for dissolution or suspension in a liquid medium prior to injection may also be prepared. The therapeutic dose of pharmaceutical composition comprising the engineered migrasome of the present application do not show significant toxicological effects in vivo.

Not to be bound by any theory, the following examples are merely to illustrate the engineered migrasome, the method for preparing the engineered migrasome and uses and the like according to the present application, and are not intended to limit the scope of the present invention.

EXAMPLES

The present application is further set forth below in conjunction with the following specific examples. It should be understood that these embodiments are intended only to illustrate the present application, instead of limiting the scope of the present application. Experimental methods without specific conditions indicated in the following examples generally follow conventional conditions in the art, for example the conditions described in Sambrook, Russeii et al., Molecular Cloning: A Laboratory Manual (Third Edition), CSHL, 2001), or follow the conditions recommended by the manufacturers. Unless otherwise stated, the experimental materials and reagents used in the following examples are commercially available.

Reagent ddH2O (solarbio), KCl (sigma), KH2PO4 (sangon), Na2HPO4-7H2O (sangon), BSA (VWR), Latrunculin A (cayman), human fibronectin (invitrogen or sigma), PBS (Gibco), RPMI 1640 (Gibco), FBS (BI), WGA-AF488/AF594/AF647 (invitrogen), BCA kits (invitrogen).

Preparation of 10×KDPBS (500 ml):

| Component | Content (g) | Concentration (mM) |
|---|---|---|
| KCl | 52.4 | 1405.7 |
| $KH_2PO_4$ | 1 | 14.7 |
| $Na_2HPO_4$—$7H_2O$ | 10.8 | 80.6 |
| ddH2O | to 500 ml | |

Formulation of 100×BSA (50 ml): 5 g of BSA was weighed out, added with ddH2O to 50 ml and then filtered using a 0.45 μm filter membrane.

Example 1

Production of Engineered Migrasomes from Cells

Example 1 Production of Engineered Migrasomes by Hypotonic Treatment

The inventor found that hypotonic treatment of cells resulted in cell body expansion, bottom surface retraction, and massive production of fibrous structures (retraction fibers), whereby migrasome-like structure was grown on the retraction fibers. To visually observe the engineered migrasomes, NRK cell lines stably expressing Tspan4-GFP were established, and the formation of engineered migrasomes was observed by means of Tspan4 signals which are one of the markers of migrasomes. The Tspan4-GFP-overexpressing NRK cells were treated with 25% DPBS (corresponding to an osmolality of 76.3 mOsmol/L), and the results were shown in FIG. 1A. The results showed that 30 seconds after hypotonic treatment, the Tspan4-GFP signal began to enrich on the retraction fibers, and then formed microscale vesicles; after reaching their peak intensity, the Tspan4-GFP signals began to diffuse from the vesicles while accompanied by the shrinkage of the vesicles; and 460 seconds after hypotonic treatment, most of the vesicle structures produced under hypotonic induction disappeared. The production of these micron-sized vesicles and their attachment to the retraction fibers were similar to those of natural migrasomes.

To further confirm whether the vesicle structures produced under hypotonic induction were engineered migrasomes, cells were stained with fluorescently-labeled wheat germ lectins (WGAs). The WGAs were lectins specifically binding to sialic acid and N-acetyl-D-glucosamine. The fluorescently-labeled WGAs could be used to label migrasomes in cells and were used as specific probes for detecting migrasomes (Chen et. al., WGA is a probe for migrasomes, Cell Discovery (2019) 5:13).

Figure 26A:
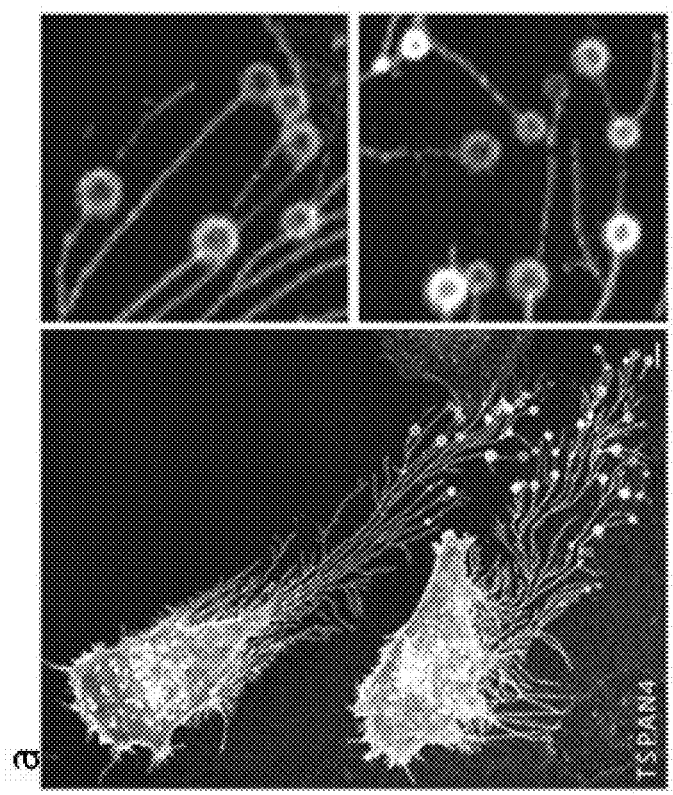
Figure 26B:
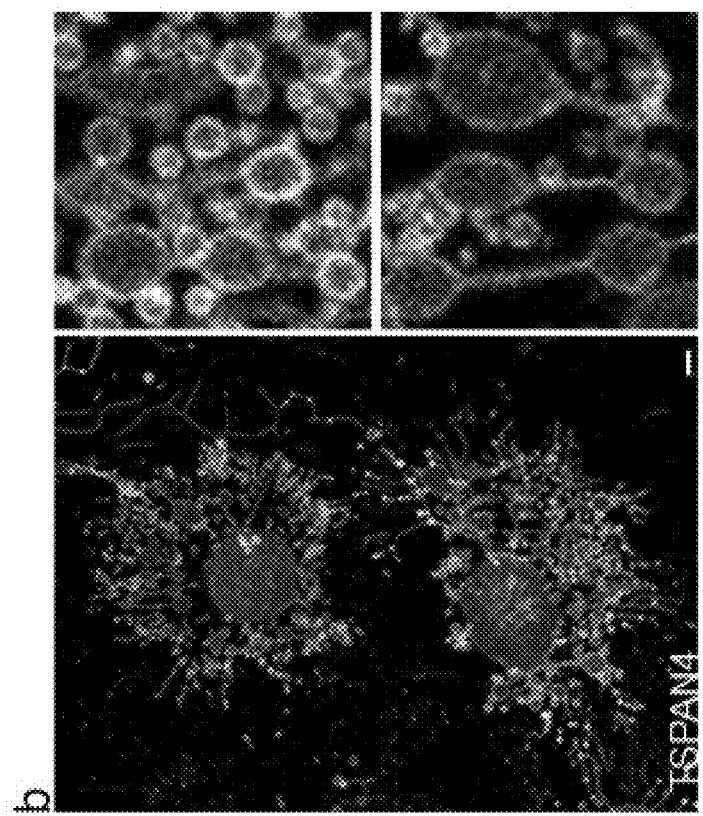
Figure 26C:
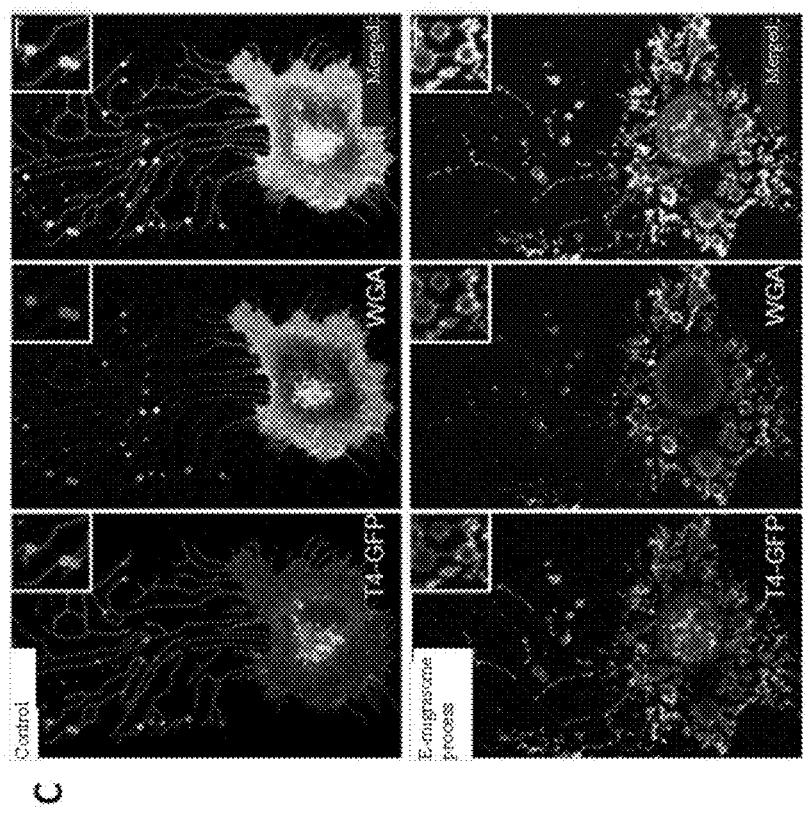

The Tspan4-GFP-overexpressing NRK cells were subject to isotonic treatment (100% DPBS, 305 mOsmol/L) and hypotonic treatment with 25% DPBS (76.3 mOsmol/L), then stained with tetramethylrhodamine-labeled WGAs, and observed by a laser confocal microscope, as shown in FIG. 26C. The results showed that the vesicle structures produced by the Tspan4-overexpressing NRK cells under induction were stained by the WGAs, indicating that the resulting vesicle structures were engineered migrasomes.

To determine the effect of osmolality on the formation of engineered migrasomes, the Tspan4-GFP-expressing NRK cells were treated with isoosmolality (100% DPBS, 305 mOsmol/L) or different low osmolality (50%, 25%, and 17% DPBS, corresponding to the osmolality of 152.5, 76.3, and 50.8 mOsmol/L, respectively) conditions. The results were shown in FIG. 1B, and the statistical results on the diameters of the engineered migrasomes were shown in FIG. 1C. It was found that the level of osmolality was negatively correlated with the size of the engineered migrasomes, and the lower the osmolality, the larger the size of the induced engineered migrasome.

Based on the above results, the inventors established a protocol for stepwise reducing the osmolality, and found that the gradual application of hypotonic treatment significantly increased the durability of the engineered migrasomes, and in cells undergoing 5-step hypotonic treatment, the induced engineered migrasomes retained after 20 minutes of hypotonic treatment.

Example 2 Production of Engineered Migrasomes by Treatment with Latrunculin A

The number of engineered migrators induced hypotonically depended on the number of retraction fibers, and most of the plasma membrane as the source of membrane of the engineered migrasome was located on the cell body. Therefore, it was speculated if the cytoskeleton was disrupted for cell contraction, the contraction would cause cell edges to retract towards the center, while the cells adhered to various points at the bottom of a culture plate through adhesion plaques, thereby allowing plasma membranes to adhere in situ as anchors for membrane tether formation. If this was the case, the retraction of cells resulted in a large number of membrane tubes in a manner similar to the formation of retraction fibers during migration.

Figure 2A:
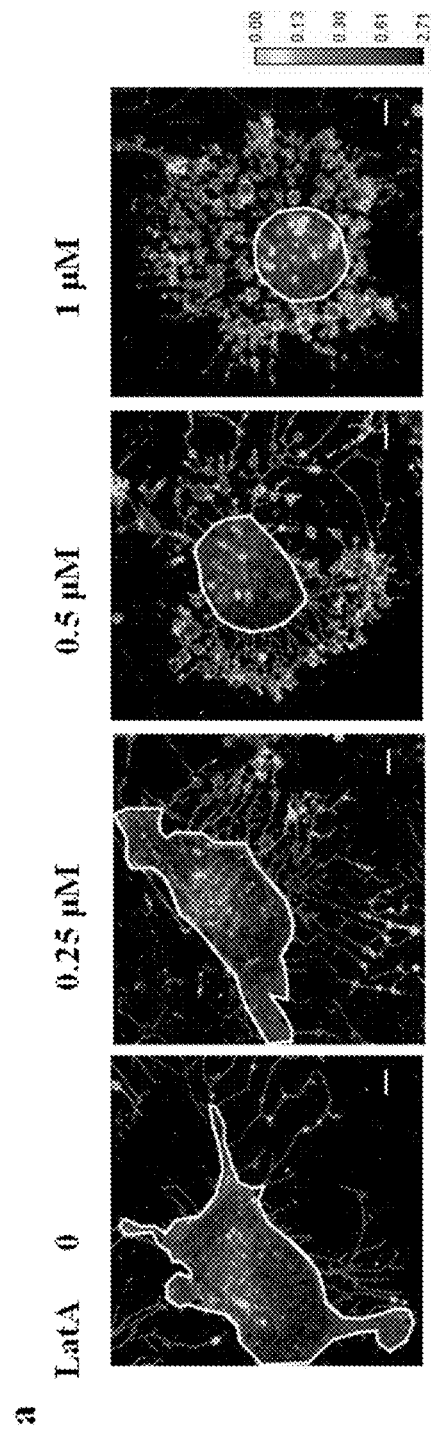
FIGS. 2A-2B show effects of treatment with latrunculin A at different concentrations on the formation of engineered migrasomes, with FIG. 2A: formation of engineered migrasomes at different concentrations of latrunculin A.
Figure 2B:
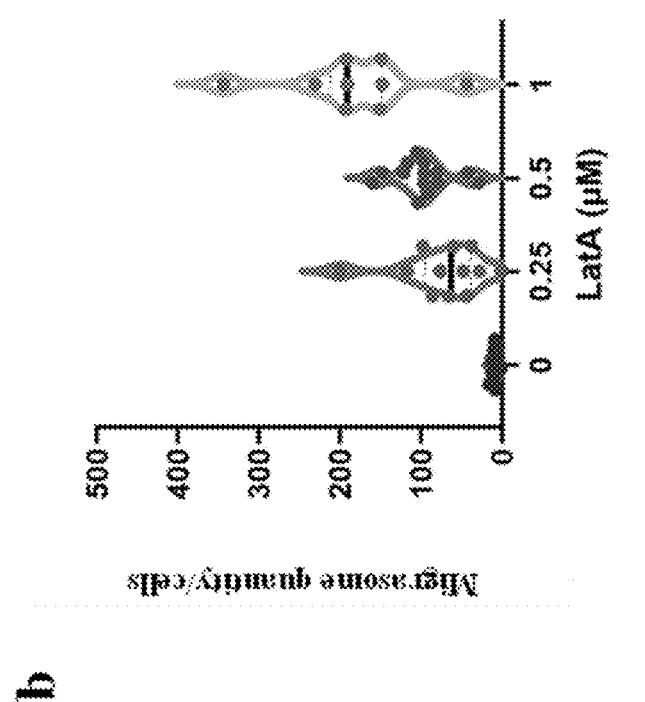

To test this hypothesis, Tspan4-GFP-expressing NRK cells were incubated for 10 min with the isotonic buffer solution DPBS containing a microfilament depolymerizing agent latrunculin A (0, 0.25 μM, 0.5 μM, and 1 μM) at different concentrations, and then step-wise hypotonically stimulated in three steps consecutively in a manner of reducing the salt concentration by ⅙ every 2 min by adding water. The results after step-wise hypotonic treatment were shown in FIG. 2A, and the statistical results of the number of engineered migrasomes produced per cell were shown in FIG. 2B.

As expected, it was found that the cells contracted when treated with latrunculin A. It was also observed that membrane tethers were massively formed on a region occupied by the cells before contraction, and these newly formed membrane tethers significantly enhanced the formation of engineered migrasomes. Thus, the latrunculin A was able to significantly promote an increase in the number of engineered migrasomes, and this promotion was dose-dependent. This suggested that the formation of engineered migrasomes could be facilitated by disrupting the cytoskeletons.

Example 3 Production of Engineered Migrasomes by Suppressing Cell Volume-Regulatory Function The cells may withstand the changes of osmolality by means of their regulated volume changes. To test whether regulated volume changes affected the formation of engineered migrasomes, SWELL 1 (which maintained a constant cell volume in response to changes in osmolality), a key component of a volume-regulatory anion channel, was knocked down or knocked out.

Figure 3A:
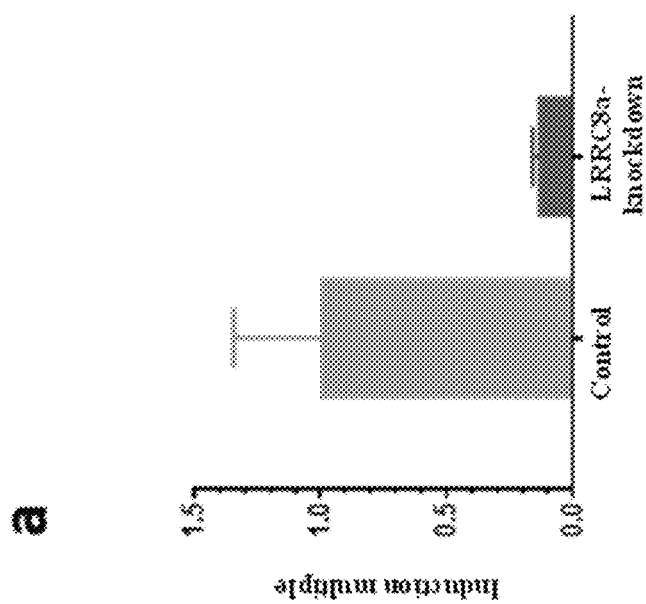
FIGS. 3A-3C show effects of knockdown of SWELL1-encoding genes Lrrc8a in cells on the formation of engineered migrasomes.
Figure 3B:
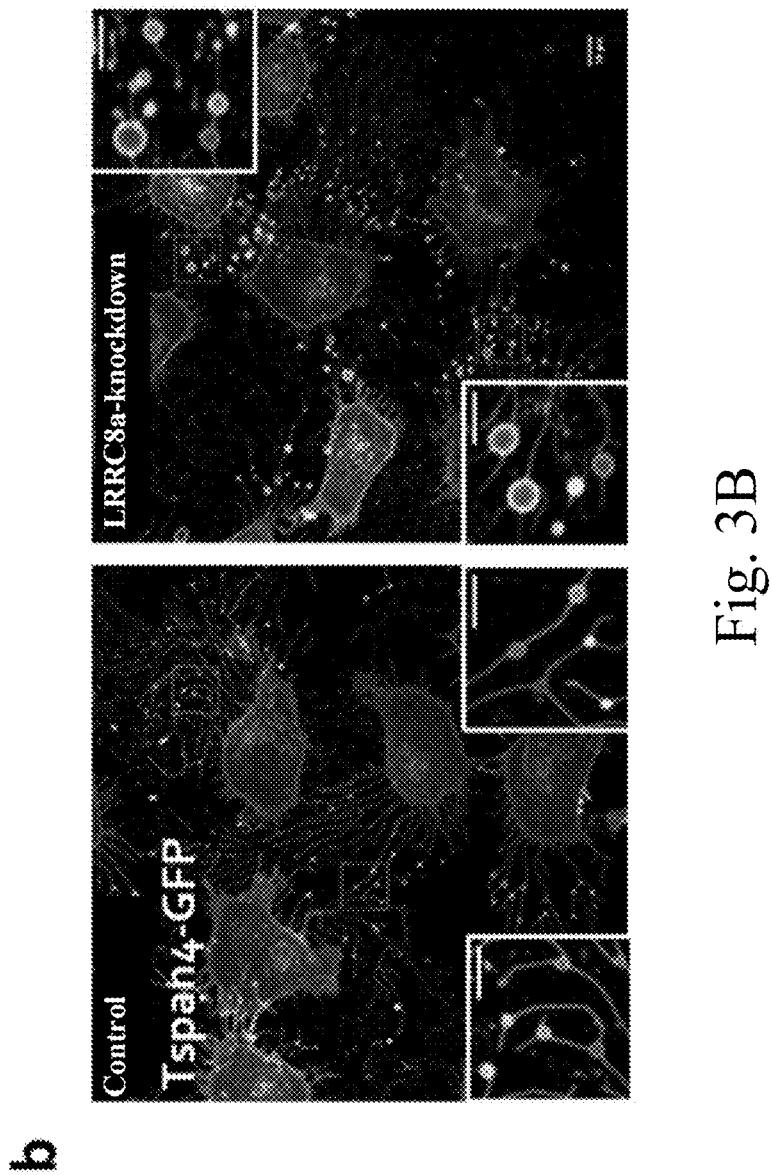
Figure 3C:
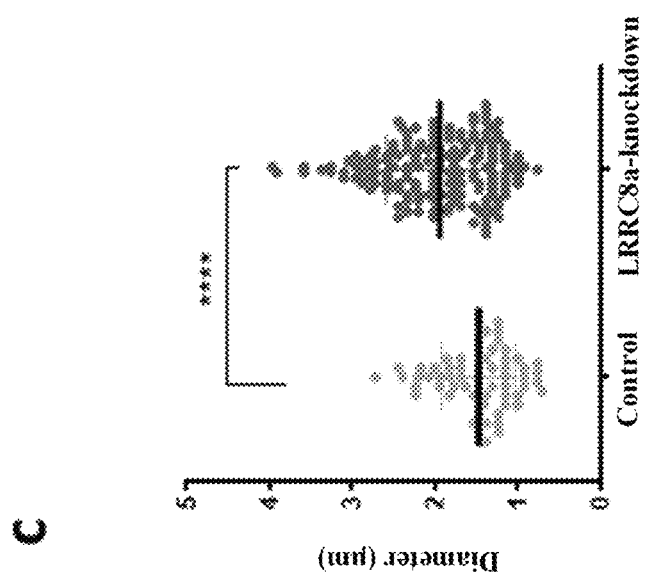

The gene Lrrc8a encoding SWELL 1 in the Tspan4-GFP-expressing NRK cells was knocked down, and the knockdown efficiency for the Lrrc8a in cells was verified by qPCR. The results showed that the gene Lrrc8a encoding the SWELL 1 was successfully knocked down to approximately 15% of wild-type cells (FIG. 3A). The cells with the gene Lrrc8a knocked down (Lrrc8a-KD) and the control cells (NC) without knockdown were placed in DPBS respectively; and the cells were step-wised hypotonically stimulated in three steps consecutively in a manner of reducing the salt concentration by ⅓ every 2 min by stepwise adding water, and then observed by a laser confocal microscope, with the results shown in FIG. 3B. The statistical results on the size of engineered migrasomes were shown in FIG. 3C.

Figure 4A:
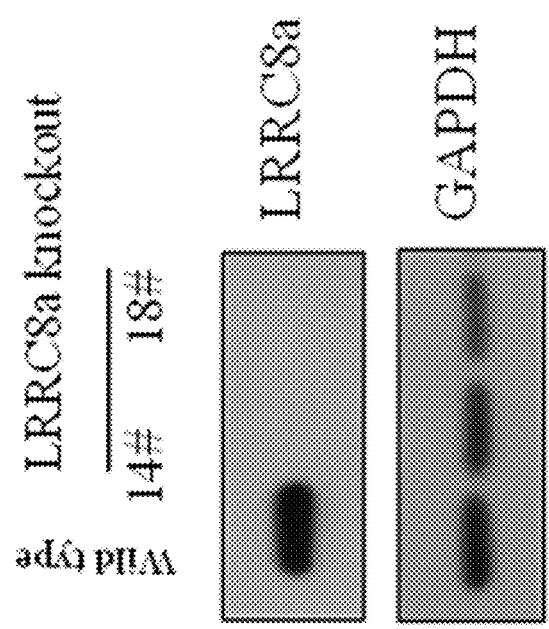
FIGS. 4A-4B show effects of knockout of SWELL1-encoding genes Lrrc8a in cells on the formation of engineered migrasomes.

The gene Lrrc8a encoding SWELL 1 in the Tspan4-GFP-expressing NRK cells was knocked out. The knockout of Lrrc8a in the cells was verified by Western blotting, and no expression of SWELL 1 was observed in the knocked-out cells (Lrrc8a-KO), indicating that the gene Lrrc8a encoding SWELL 1 was successfully knocked out (FIG. 4A). The Lrrc8a-KO cells (KO14 #cell line and KO018 #cell lines) and the control cells (WT) without knockout were placed in DPBS respectively; and the cells were step-wise hypotonically stimulated in five steps consecutively in a manner of reducing the salt concentration by ⅙ every 1 min by stepwise adding water, and then observed by a laser confocal microscope, with the results shown in FIG. 4B.

Figure 4B:
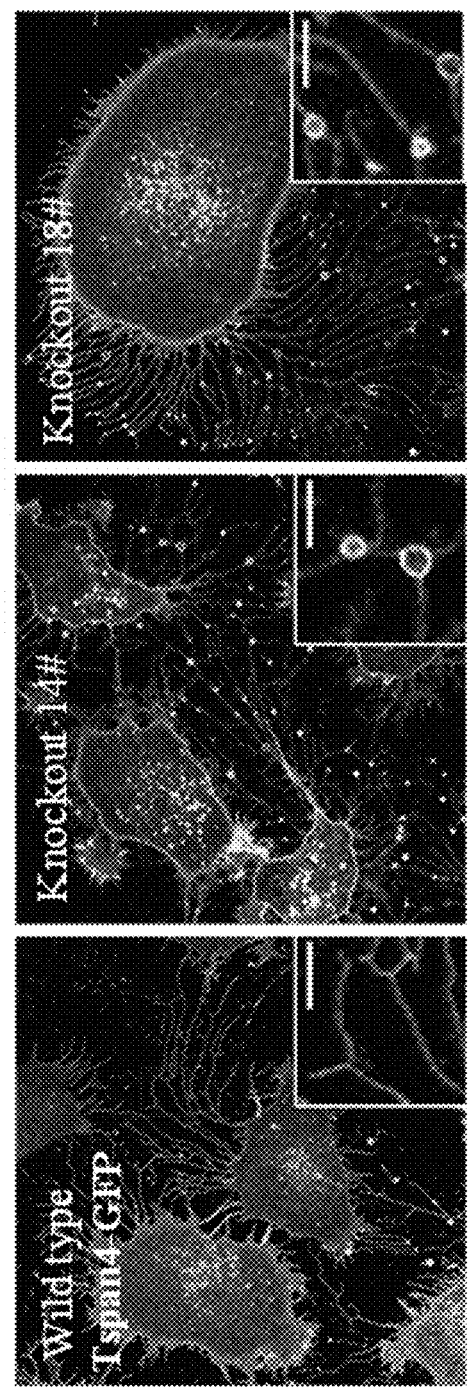

The results showed that after hypotonic treatment, the engineered migrasomes produced by the Lrrc8a-knockdown cells had a size that was significantly larger than those produced by the cells without knockdown (FIGS. 3B and 3C); and the engineered migrasomes produced by the Lrrc8a-knockout cells also had a size that was significantly larger than those produced by the cells without knockout (FIG. 4B). This indicated that the knockdown or knockout of SWELL 1 significantly enhanced the formation of engineered migrasomes, suggesting that the formation of engineered migrates could be enhanced by reducing the ability of cells to adjust their volume during osmolality changes.

Figure 5A:
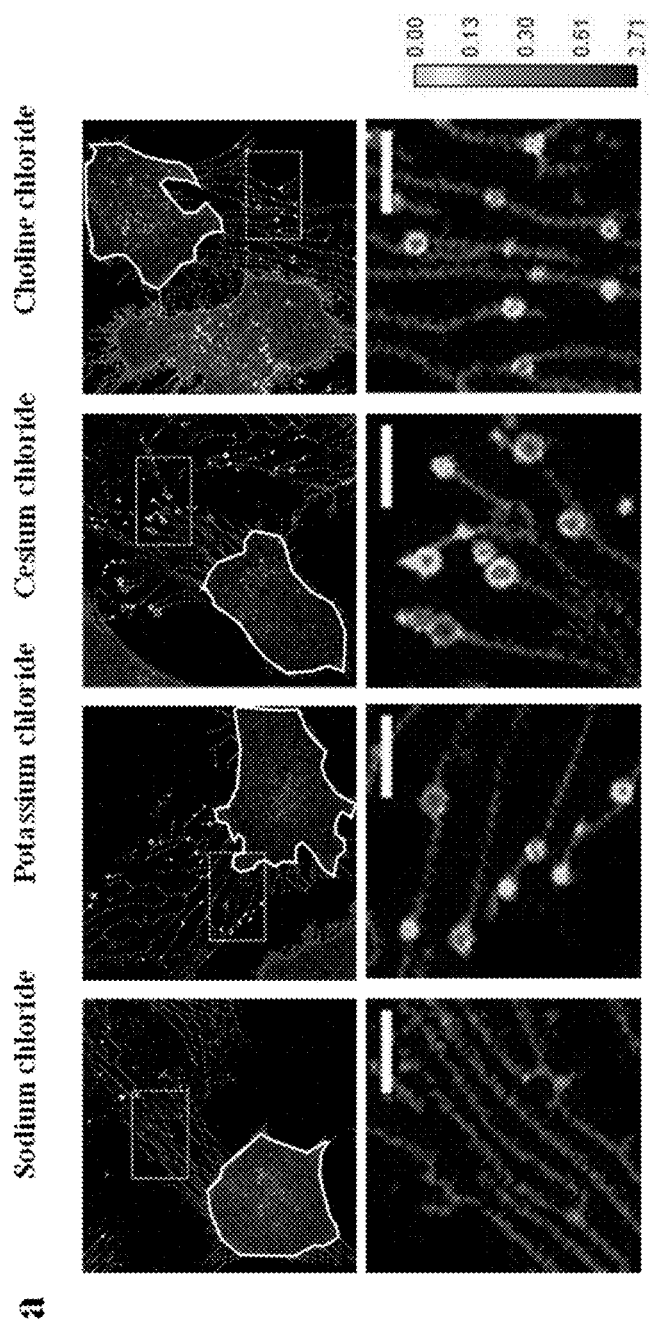
FIGS. 5A-5B show effects of treatment with different cations on the formation of engineered migrasomes.
Figure 5B:
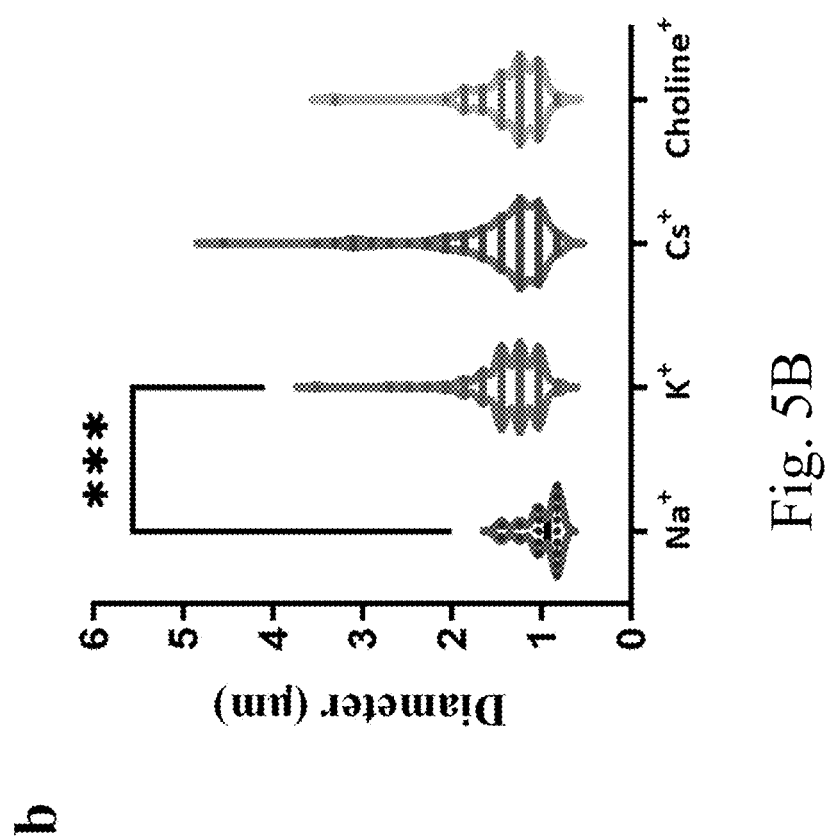

Cations were known to regulate the cell volume. If different cations showed different abilities to regulate the cell volume during osmolality changes, the regulated cell volume changes can be reduced by cation replacement, thereby promoting the formation of engineered migrasomes. Next, the effect of different cations on the formation of engineered migrasomes was tested. Sodium chloride in DPBS was replaced with potassium chloride, cesium chloride, or choline chloride at an equal molar concentration to formulate an isotonic buffer solution containing different cations; and the cells were incubated respectively by using these isotonic buffer solutions, and were step-wise hypotonically stimulated consecutively in five steps in the corresponding buffer solution in a manner of reducing the salt concentration by ⅙ every 2 min by stepwise adding water. The results after stepwise hypotonic treatment were shown in FIG. 5A, and the statistical results of the size of engineered migrasomes were shown in FIG. 5B.

The results showed that different cations had different abilities to promote the formation of engineered migrasomes, and among the tested cations, sodium ions had relatively weak ability to promote the formation of engineered migrasomes, while potassium ions, cesium ions, and choline ions had significantly stronger ability to promote the formation of migrasome-like structures.

Example 4 Production of Engineered Migrasomes by Overexpressing Tspan4 in Cells

Figure 6A:
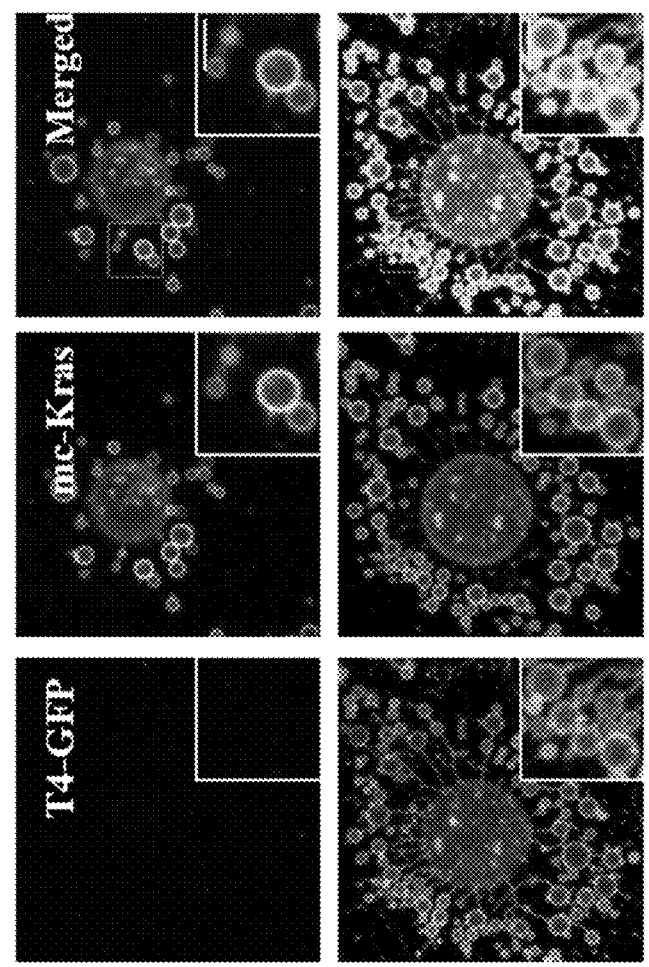
FIGS. 6A-6B show effects of overexpression of Tspan4 on the number of engineered migrasomes.
Figure 6B:
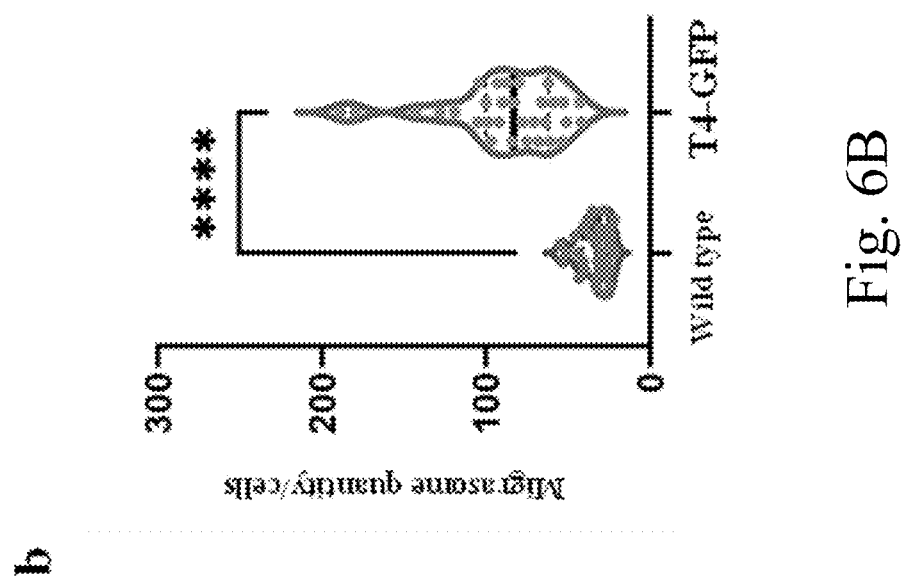

Tspan4 was a key protein for migrasome formation. To test whether Tspan4 could promote the formation of engineered migrasomes, stepwise hypotonic stimulation was carried out on NRK cells that only overexpressed mCherry-Kras or NRK cells that overexpressed both Tspan4-GFP and mCherry-Kras. After incubating the NRK cells for 10 min in KDPBS containing 2 μM latrunculin A, step-wise hypotonic stimulation was carried out in three steps consecutively in a manner of reducing the salt concentration by ⅙ every 2 min, and then the formation of engineered migrasomes was observed by a differential interference contrast microscope. The results after stepwise hypotonic treatment were shown in FIG. 6A, and the statistical results of the number of engineered migrasomes produced per cell were shown in FIG. 6B.

The results showed that the overexpression of Tspan4 significantly increased the number of engineered migrasomes.

Figure 7A:
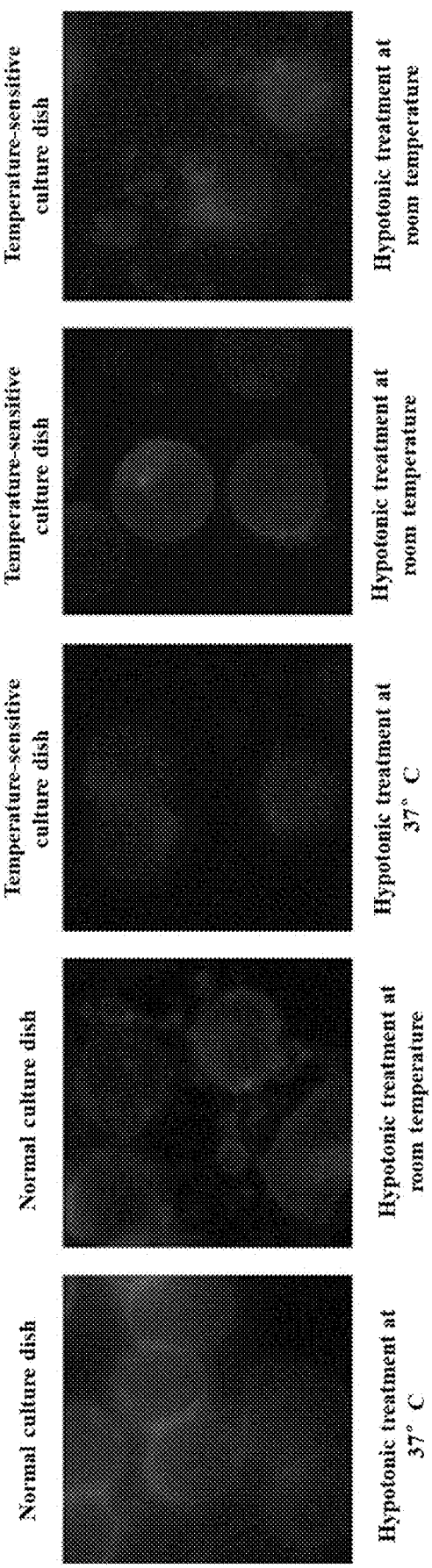
FIGS. 7A-7B show migrasomes produced by MGC803-T4-GFP cells in a temperature-sensitive coated culture dish.
Figure 7B:
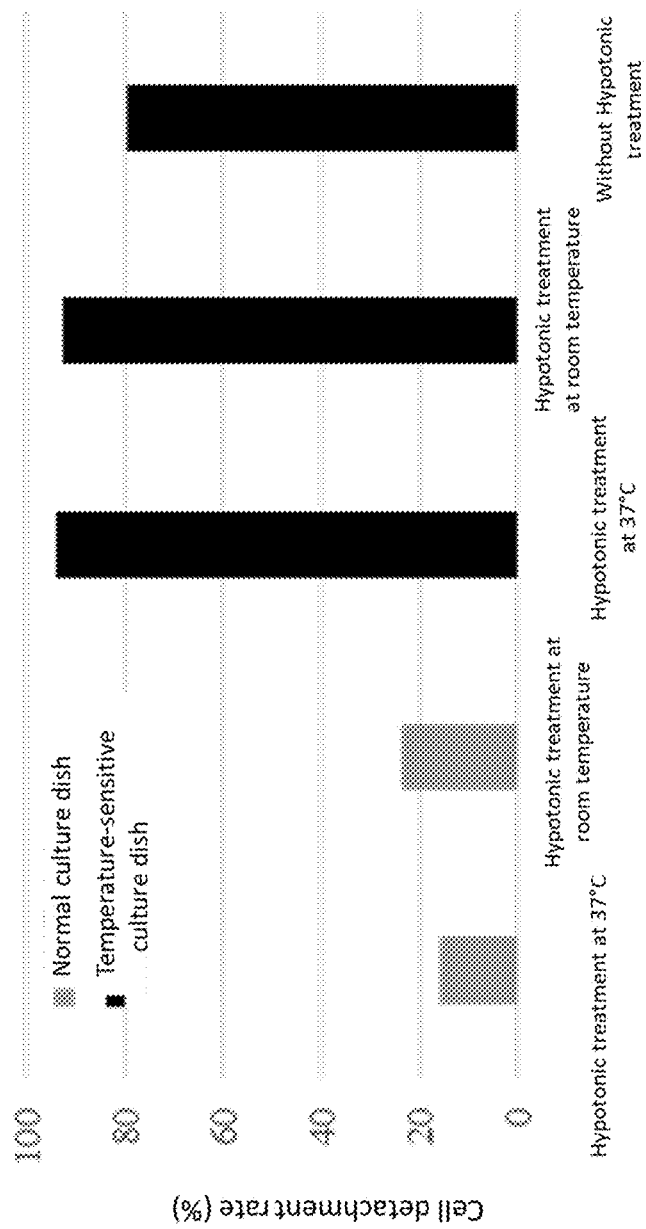

Example 5 Production of Engineered Migrasomes by Rapid Cell Detachment with Temperature-Sensitive Coating of Culture Dish MGC803-T4-GFP cells were cultured on a temperature-sensitive culture dish; after cytoskeleton disruption treatment, hypotonic treatment was carried out at room temperature or at 37° C., or no hypotonic treatment was carried out; and the culture dish was left still at room temperature for 45 minutes. More than 80% of the cells were detached from the bottom of the culture to form migrasomes, some of which were detached from the bottom of the dish along with the cells (see FIG. 7). The supernatant was collected and pipetted to collect residual cells and migrasomes.

Example 6 Production of Engineered Migrasomes in Various Cell Lines

To test whether engineered migrasomes could be produced under induction in cell lines of different species and genetic background, three different rodent cell lines (including normal rat kidney (NRK) cells, mouse breast cancer cell lines (4T1) and mouse colon cancer cell lines (MC38)), two commonly used human embryonic kidney cell lines/lines (HEK-293T and HEK-293FT), three different human cell lines (human gastric cancer MGC-803 cells, human T lymphocytoma Jurkat cells, and human skin fibroblasts BJ cells), all of which overexpressed Tspan4, were subject to hypotonic induction. After the NRK cells were incubated for 10 min in K-DPBS containing 2 μM latrunculin A, step-wise hypotonic stimulation was carried out in three steps consecutively in a manner of reducing the salt concentration by ⅙ every 2 min; after the 4T1 cells were incubated for 20 min in K-DPBS containing 2 μM latrunculin A, step-wise hypotonic stimulation was carried out in three steps consecutively in a manner of reducing the salt concentration by ¼ every 2 min; and after the MC38 cells were incubated for 45 min in K-DPBS containing 2 μM latrunculin A, step-wise hypotonic stimulation was caned out in three steps consecutively in a manner of reducing the salt concentration by ¼ every 2 min. The results were shown in FIG. 8. It could be seen that vesicle structures were produced in different cell lines.

Figure 8A:
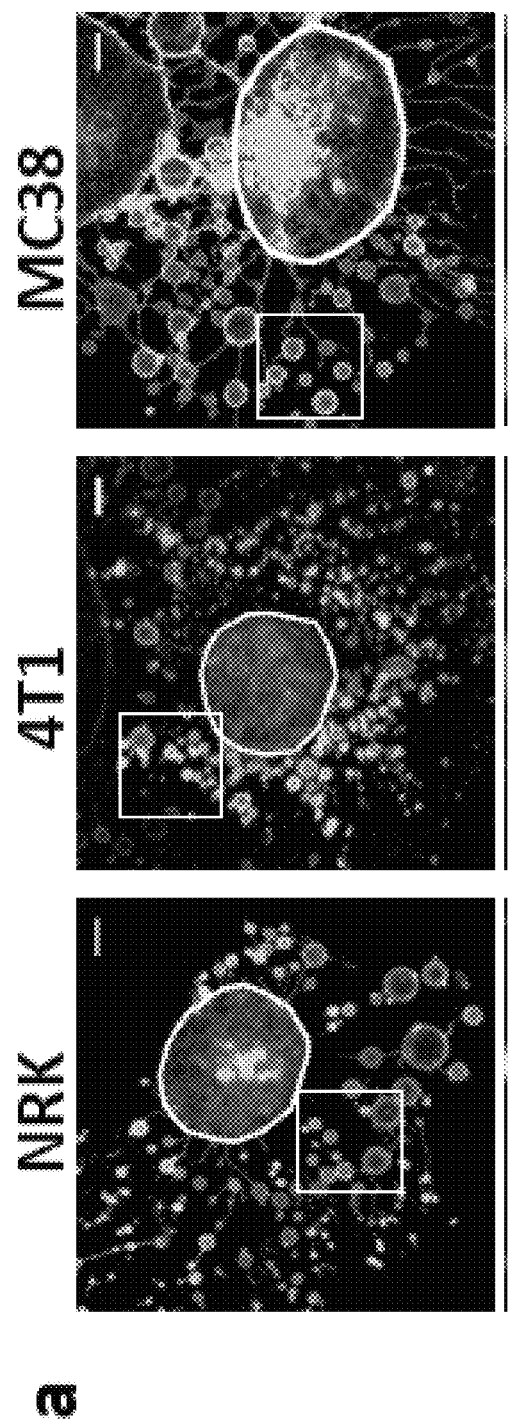
FIGS. 8A-8D show engineered migrasomes induced in different cell lines.
Figure 8B:
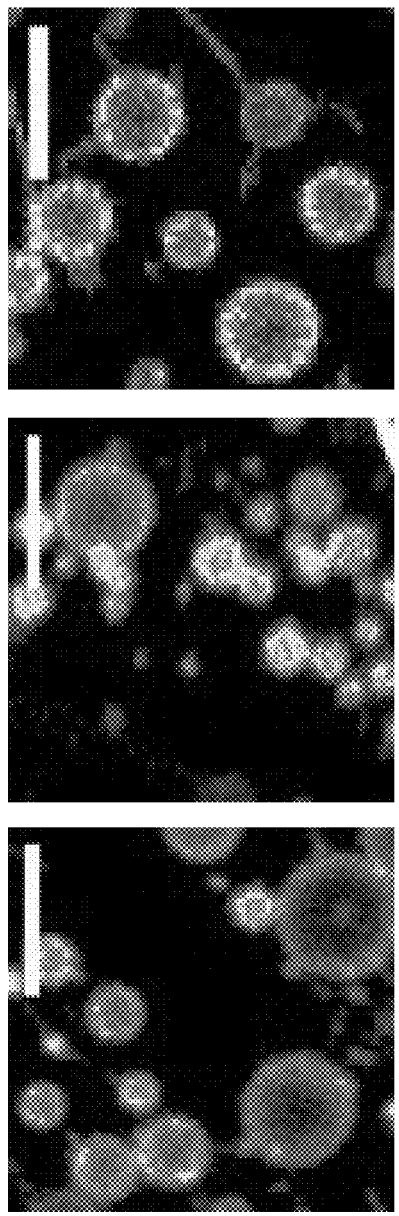
Figure 8C:
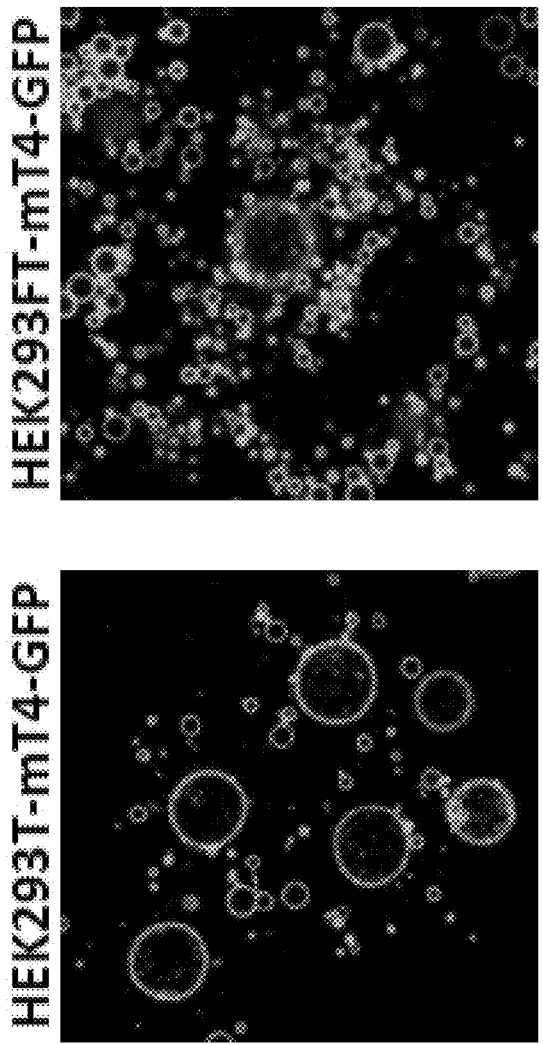
Figure 8D:
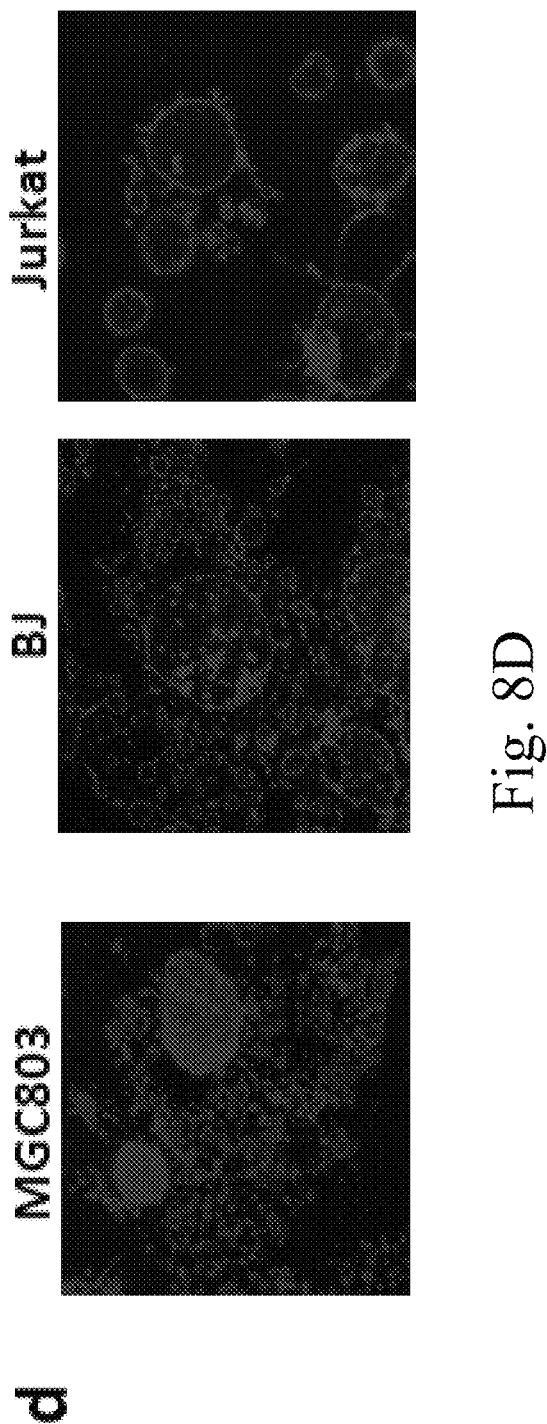

The hypotonically treated cell lines described above were further stained with a migrasome-specific probe, tetramethylrhodamine-labeled WGA, and then observed by a laser confocal microscope. The results were shown in FIG. 8B. Human cell lines (human embryonic kidney cells (HEK293T and HEK293FT; FIG. 8C), human gastric cancer cells (MGC803), human skin fibroblasts (BJ), and human peripheral blood leukemia T cells (Jurkat); FIG. 8D) were also tested. It was found that the methods of embodiments 1-5 can generate engineered migrasomes. The results showed that the vesicle structures produced in the eight cell lines under induction were stained by the migrasome probe WGA, indicating the production of engineered migrasomes.

The above results showed that the engineered migrasomes could be produced in different cell lines by the methods of Examples 1-5.

Figure 9A:
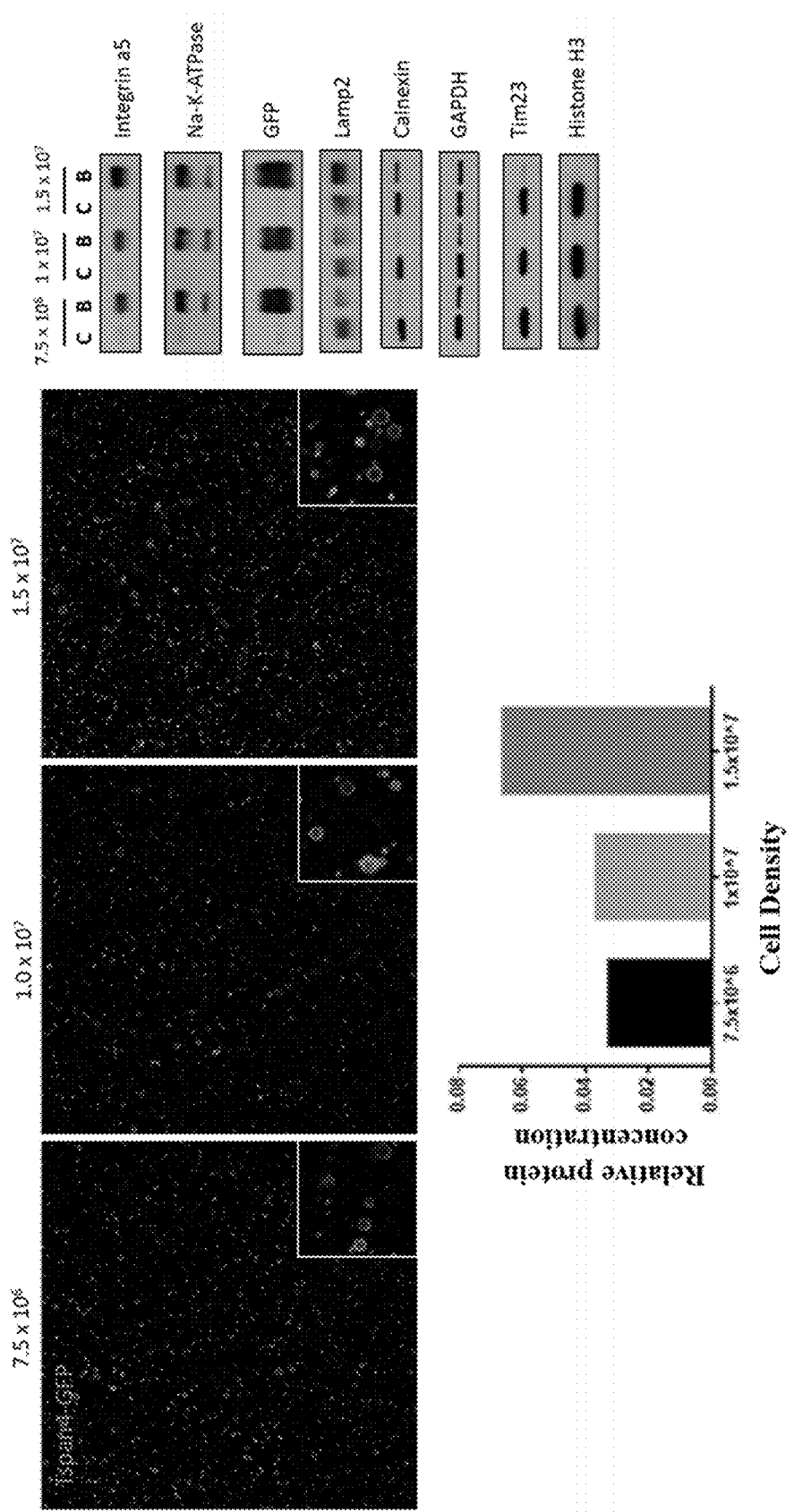
FIGS. 9A-9B show engineered migrasomes induced differentially in NRK (FIG. 9A) and MC38 (FIG. 9B) cells cultured in suspension at different cell concentrations.
Figure 9B:
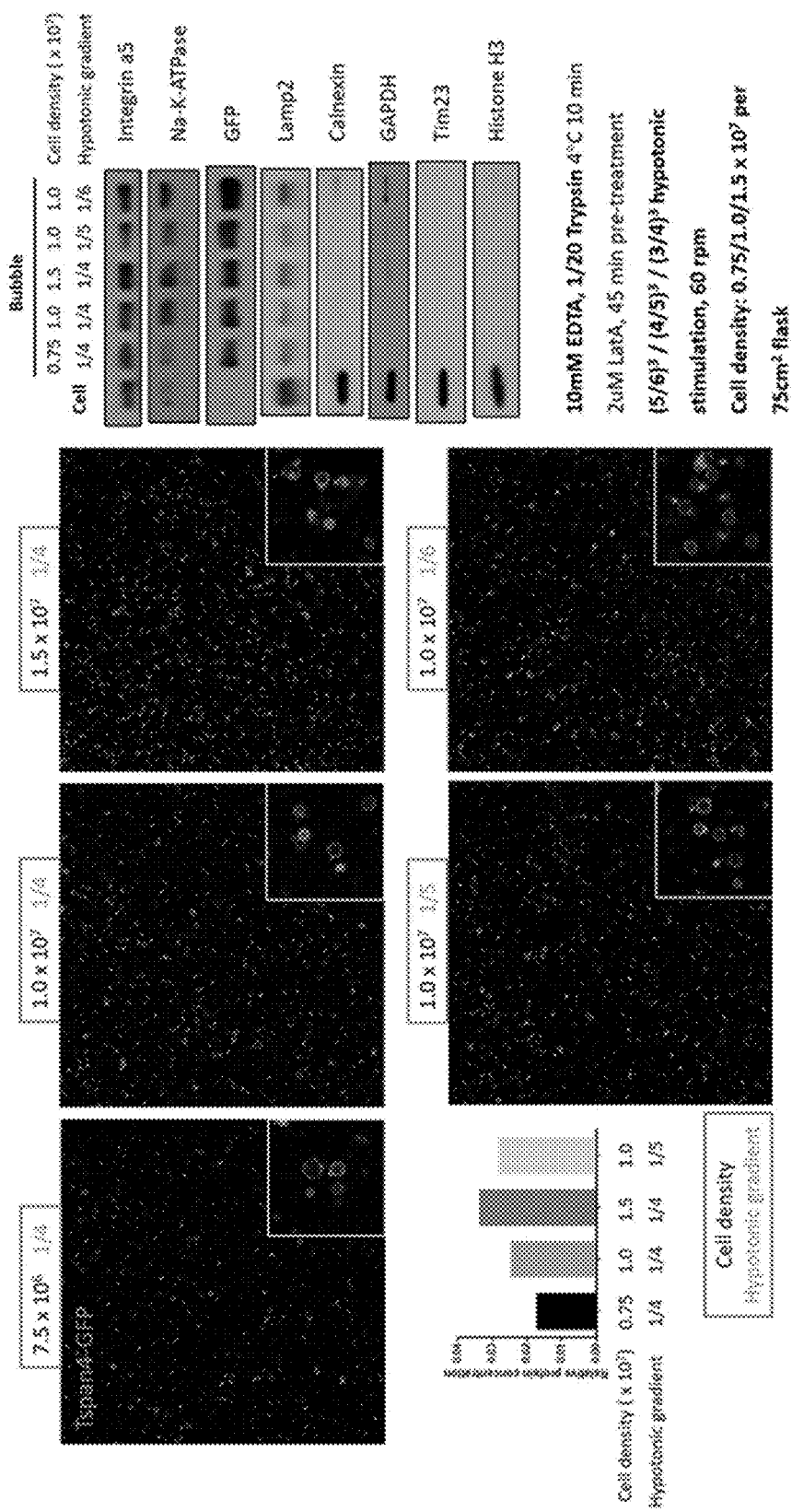

Example 7 Isolation, Purification, and Characterization of Engineered Migrasomes (FIGS. 9a-b)

a. Production of Engineered Migrasomes by Stimulation of Adherent Cells

I. Coating of Culture Flasks and Spreading of Cells

2 μg/ml human fibronectin was prepared with PBS to coat the bottom surface of the culture flask at 37° C. for more than one hour, and then the cells were spread at a density of $1\times10^7$ cells/T175 culture flask.

II. Production of Induced Engineered Migrasomes

1. After 14-16 h of cell culture, the culture medium was discarded and the cells were washed once with PBS.
2. K-DPBS containing 2 μM latrunculinA was added to incubate the cells at 37° C. (the specific incubation time was adjusted according to the sensitivity of the cell line to latrunculin A, for example, 10 min for treatment of NRK cells and 45-60 min for treatment of MC38 cells; and after the treatment was completed, the cells should be in a wrinkled state, with lots of reticulated structures similar to retraction fibers around the cell bodies).
3. The culture flask was placed on a horizontal shaker in a cell culture incubator at a revolving speed of 40 rpm, and water was added every three minutes for a total of three operations (the volume of water added at each step was determined by the hypotonic induction gradient and the initial volume of liquid in the culture flask; the hypotonic induction gradient varies by cell line; for MC38 cells, the salt concentration was reduced by ¼ at each step, the initial volume was 15 ml and the volumes of water added three times were 5 ml, 6.5 ml and 8.5 ml, respectively; and for NRK cells, the initial volume was 15 ml, and the volumes of water added three times were 3 ml, 3.6 ml, and 4.4 ml);
4. The revolving speed was adjusted to 60 rpm to shake for 5 min.

b. Suspension Cells were Stimulated to Produce the Engineered Migrasomes

The cells (the number of which depends on the cell line) were taken out and washed once with PBS, and the supernatant was discarded.

K-DPBS containing 2 μM latrunculin A was added to resuspend the cells in the culture flask, which was placed in the horizontal shaker and incubated at the revolving speed of 40 rpm (the time varies by cell line).

Sterile water was added to the culture flask to reduce the osmolality (at a ratio varying by cell line).

The revolving speed was adjusted to 60 rpm to shake for 5 min.

To test whether engineered migrasomes could be produced in cell lines in suspension by induction, hypotonic induction was carried out on two different rodent cell lines (normal rat kidney cells (NRK) and mouse colon cancer cell lines (MC38)) overexpressing Tspan4. The results were shown in FIGS. 9a and 9b. Vesicle structures were produced in both cell lines in suspension, and the Western blotting showed that vesicles purified from both cell lines showed enrichment of distinctive membrane proteins of engineered migrasomes and deletion of intracellular substances.

Figure 10:
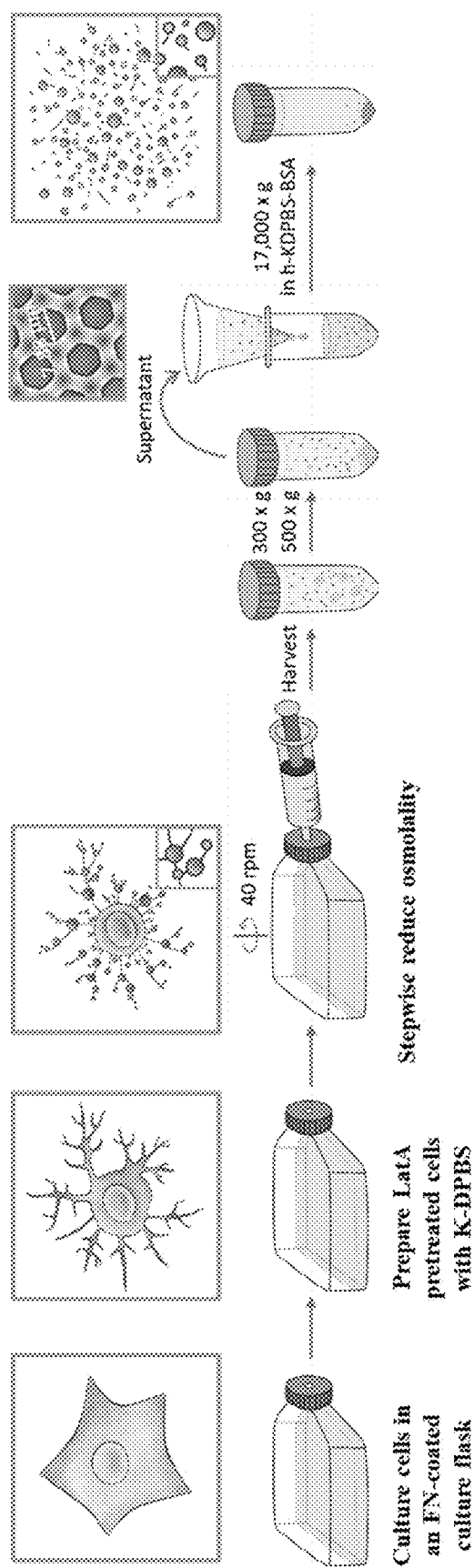
FIG. 10 shows a schematic flowchart of the isolation and purification of engineered migrasomes induced from engineered NRK cells.

III. Isolation and Purification of Engineered Migrasomes (FIG. 10)

a. Method for Purifying Engineered Migrasomes Produced by Adherent Cells

1. The supernatant was discarded, and the cells were washed twice with hypotonic KDPBS (hKDPBS; its salt concentration was similar to that in the solution system when hypotonic induction was completed; for MC38 cells, h-KDPBS was 40% KDPBS; and for NRK cells, h-KDPBS was 60% KDPBS).
2. h-KDPBS (h-KDPBS-BSA) containing 1 mg/ml BSA was added and shaken for 3 min at 130 rpm.
3. The supernatant was collected into a 50 ml centrifuge tube.
4. h-KDPBS-BSA was added, the bottom surface of the culture flask was gently pipetted using a pipette, and the collected liquid and the supernatant from step 3 were combined.
5. Centrifugation was carried out for 10 min at 4° C. at 300×g and the supernatant was retained.
6. Centrifugation was carried out for 10 min at 4° C. at 500×g and the supernatant was retained.
7. The supernatant was filtered into a 50 ml low-adsorption tube by using a parylene filter membrane having a pore size of 8 μm.
8. Centrifugation was carried out for 45-60 min at 4° C. at 17000×g and the supernatant was discarded.
9. Pellets were resuspended with h-KDPBS-BSA, transferred to an EP tube (centrifuge tube 1), and added with an equal volume of PBS-BSA. Here, a small portion of liquid (about 1/50 the total volume) was taken and put in another centrifuge tube (centrifuge tube 2) for measurement of protein concentration.
10. Centrifugation was carried out for 15-20 min at 4° C. at 17000×g, the supernatant was discarded, PBS was added, and the pellets were resuspended before injection to obtain the engineered migrasomes resuspended in PBS.

b. Method for Purifying Engineered Migrasomes Produced by Suspension Cells

1. The supernatant was collected and put into a 15 ml centrifuge tube and then pipetted gently using a pipette.
5. Centrifugation was carried out for 10 min at 4° C. at 300×g and the supernatant was retained.
6. Centrifugation was carried out for 10 min at 4° C. at 500×g and the supernatant was retained.
7. The supernatant was filtered into a low-adsorption tube by using a parylene filter membrane having a pore size of 8 μm.
8. Centrifugation was carried out for 45-60 min at 4° C. at 17000×g and the supernatant was discarded.
9. The pellets were resuspended with PBS and transferred into an EP tube to obtain the engineered migrasomes resuspended in PBS.

IV. Characterization of Engineered Migrasome

1. Determination of Total Protein

The liquid in the centrifuge tube 2 was centrifuged for 5 min at 4° C. at 17000×g; the supernatant was discarded, the pellets were then washed once with PBS, and the supernatant was discarded; the pellets were lysed with 30 µl of 2% SDS; and the resultant sample was boiled in a metal bath at 95° C. The protein concentration was determined by the BCA method to convert the total amount of protein in the centrifuge tube 1, and the corresponding resuspension volume was converted according to an injected dose.

2. Morphological Observation

Figure 11A:
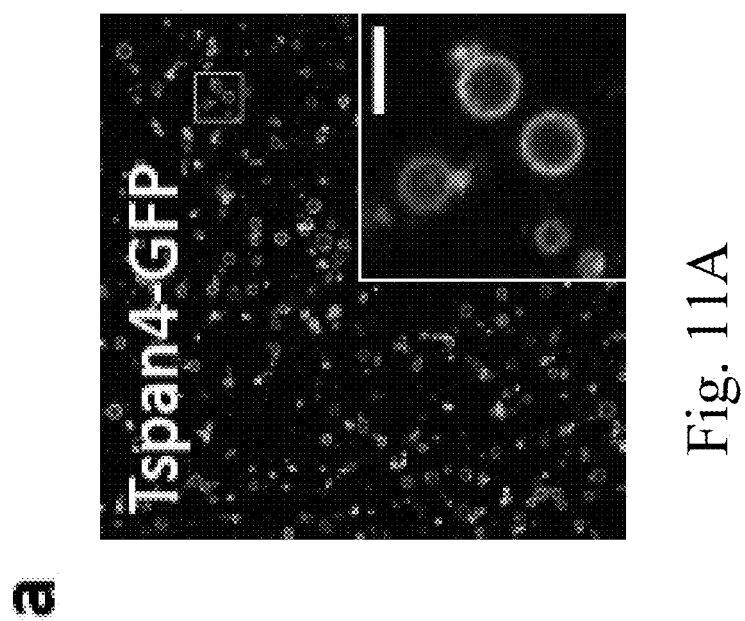
FIGS. 11A-11C show morphological observations of engineered migrasomes induced in engineered NRK cells, with FIG. 11A: laser confocal microscopic images of engineered migrasomes.

1 µl of the engineered migrasome sample obtained from step III was diluted to 10 µl (a WGA dye could be added to the diluent at a ratio of 1:500-1:1000 to observe the morphology of vesicles and the detachment on the membrane surface), added dropwise to a confocal capsule previously coated with 10 µg/ml fibronectin, allowed to stand for more than 1 h at room temperature, and observed under a laser confocal microscope. The results were shown in FIG. 11A.

Figure 11B:
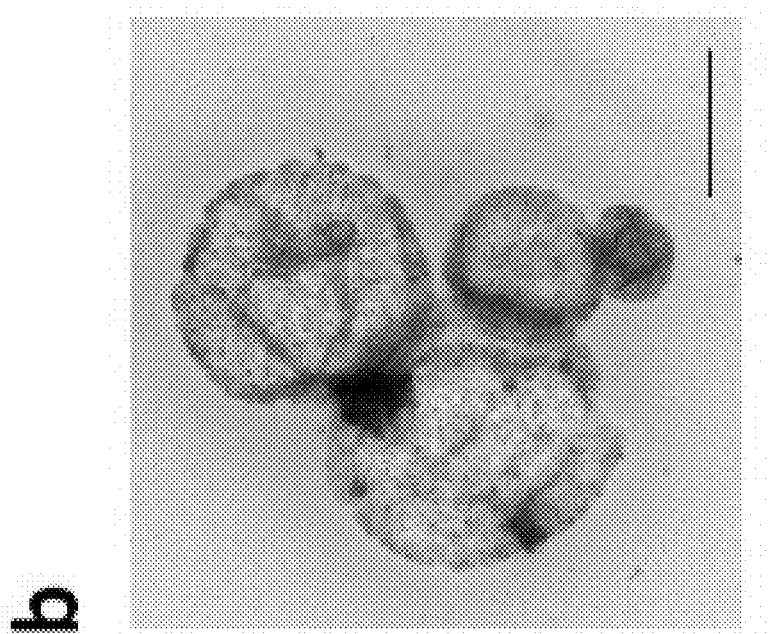
Figure 11C:
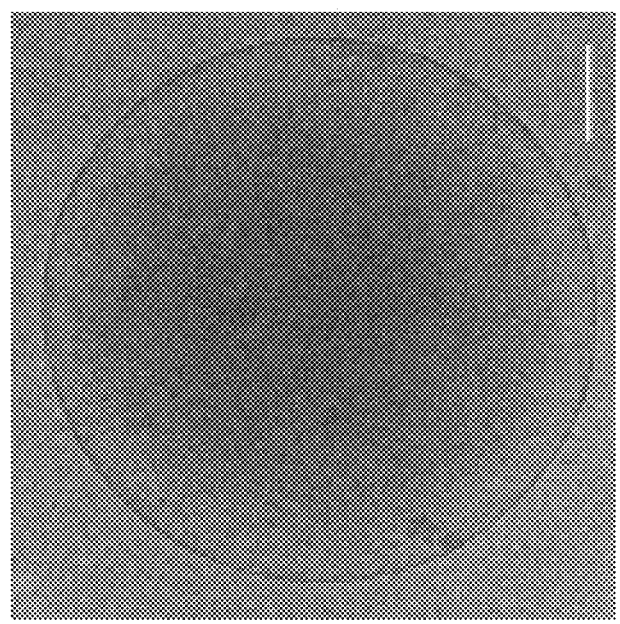

In addition, the engineered migrasomes obtained in step III were observed with a negative-staining transmission electron microscope and a cryo-electron microscope, and the results were shown in FIGS. 11b and 11c, respectively.

3. Flow Cytometry

1 µl of liquid at step III-9 or 10 was diluted to 100 µl. If the vesicles showed two-color fluorescence, they could be directly diluted with PBS; and if the vesicles only showed monochromatic fluorescence, they can be stained with a 1:500 WGA dye to improve the effect of clustering.

4. Western Blotting

Figure 12:
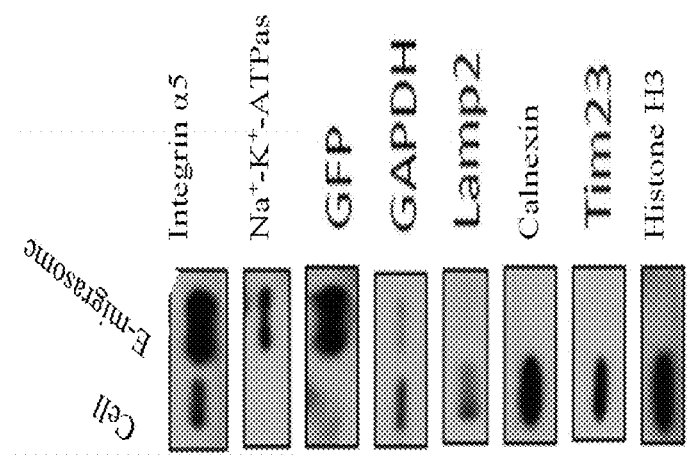
FIG. 12 shows Western blotting of isolated and purified engineered migrasomes.

A small amount of liquid was taken from the supernatant in step III-1, and centrifuged at 100×g, and the pellets were lysed with 2% SDS to serve as cell samples; and the samples obtained in step IV-1 were used as engineered migrasome samples. The cell samples and the engineered migrasome (eMig) samples were loaded at equal protein content for Western blotting to detect classical markers of a variety of organelles, including: nucleus (histone H3), mitochondria (Tim23), endoplasmic reticulum (calnexin), lysosomal (Lamp2), cytoplasm (GAPDH), cytomembrane ($Na^+$—$K^+$-ATPase), cytomembrane adhesion plaque (integrin α5), and Tspan4-GFP (GFP). The result was shown in FIG. 12.

The results showed that the isolated and purified engineered migrasomes were highly enriched with cytomembrane proteins such as Tspan4, integrin a5, and $Na^+$—$K^+$-ATPase, with little or no contamination from intracellular organelles and soluble proteins.

5. Permeability Assessment

Figure 13A:
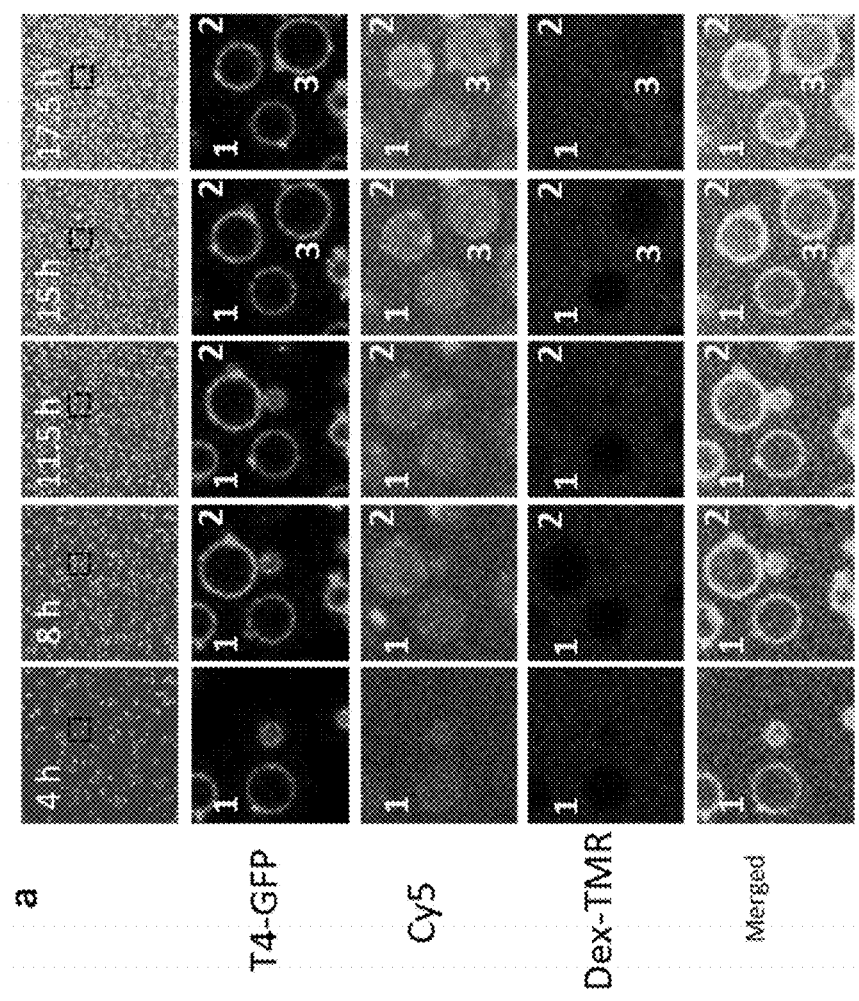
FIGS. 13A-13B show permeability of engineered migrasomes to Cy5 and dextran-TMR over time as observed by a laser confocal microscope.
Figure 13B:
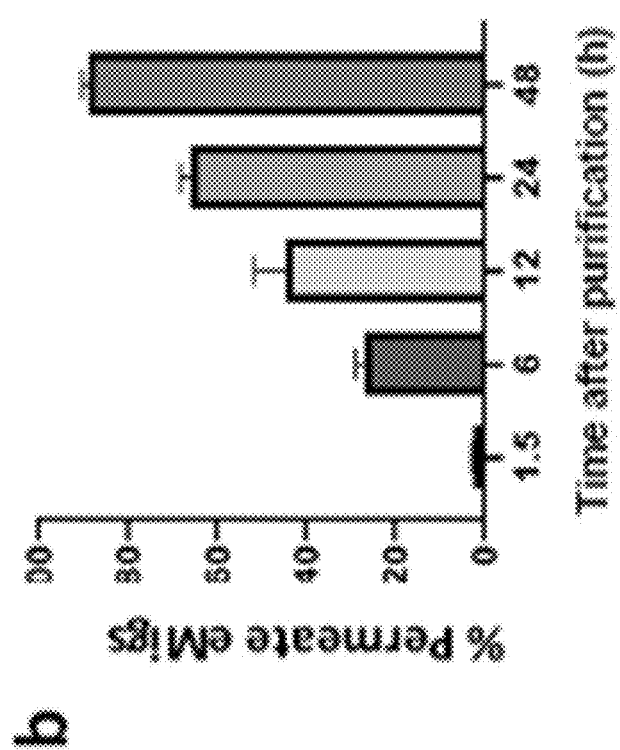

The isolated and purified engineered migrasomes were dropwise added to a confocal capsule, and Cy5 (a fluorescent dye that cannot pass through intact membranes) and dextran-TMR (Dex-TMR) were added to the buffer solution to indicate the permeability of vesicles. Long-term shooting was carried out on droplets using a laser confocal microscope, with the results shown in FIG. 13A. It could be observed that the engineered migrasomes were almost completely permeable to Cy5 (MW<1 kDa) at room temperature from the beginning, and showed slow permeability to dextran-TMR (MW=40 kDa) with a larger molecular weight; and after the engineered migrasomes stored for 1.5 h, 6 h, 12 h, 24 h, and 48 h at room temperature, their permeability ratio to the dextran-TMR were shown in the statistical results in FIG. 13B.

6. Stability Assessment

Figure 14A:
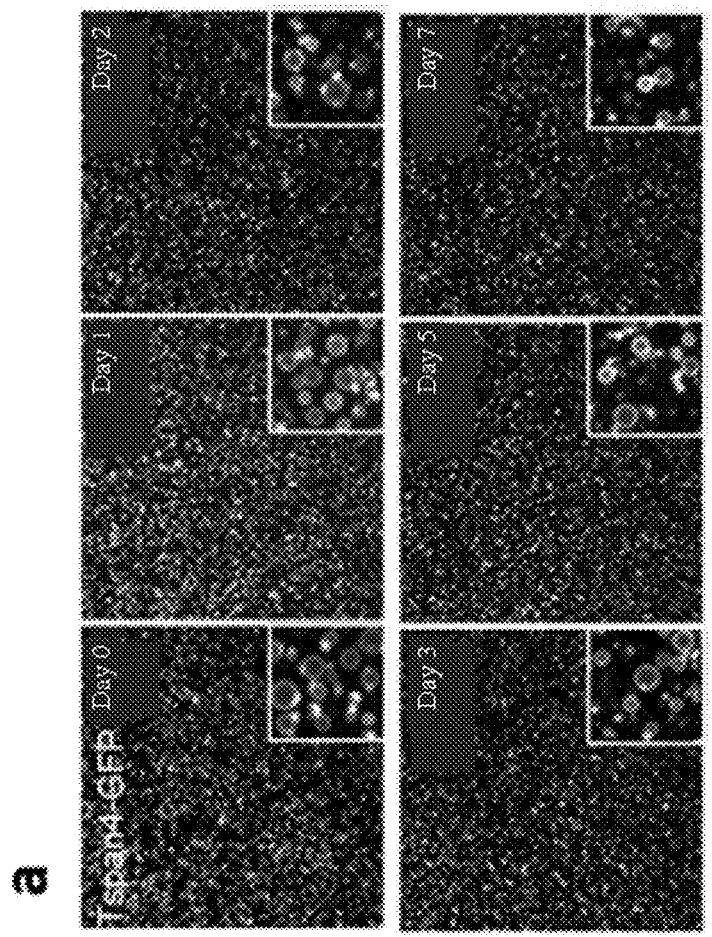
Figure 14B:
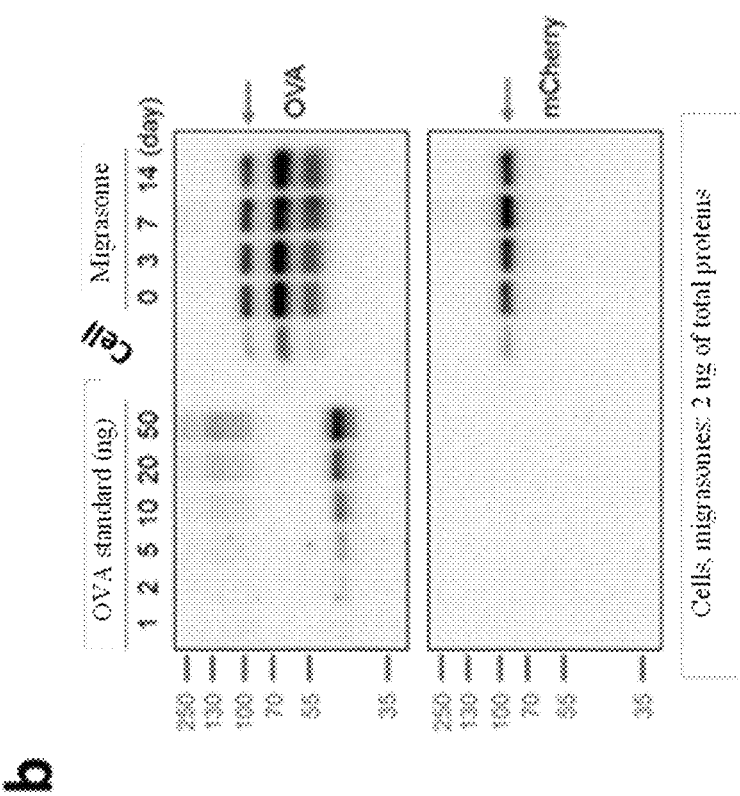

To explore the stability of engineered migrasomes at room temperature, the isolated and purified engineered migrasomes were added dropwise to a confocal capsule, and morphologically observed on days 0, 1, 2, 3, 5, and 7, respectively, with the results shown as in FIG. 14A. Six samples retained in parallel were subject to Western blotting to detect the loaded OVA and mCherry (FIG. 14B) on days 0, 3, 7, and 14, and they were used to immunize mice to detect the concentration of OVA-specific antibodies in serum (FIG. 14C).

The results showed that the engineered migrasomes had intact vesicle morphology, stable protein expression, and basically no change in immunogenicity as a vaccine during storage for 7-14 days at room temperature, indicating that the engineered migrasomes were very stable.

7. Effect of Cholesterol on Stability of Engineered Migrasomes

Figure 15:
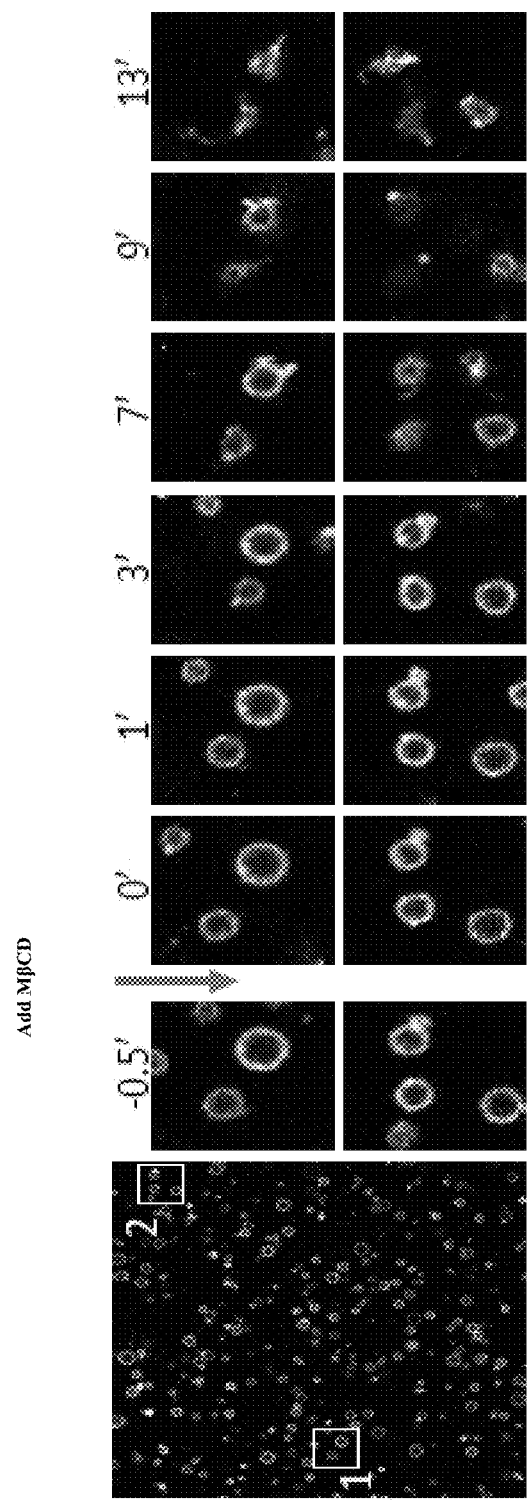
FIG. 15 shows effects of a cholesterol extraction reagent MβCD on the stability of engineered migrasomes as observed by a laser confocal microscope.

It was previously reported that cholesterol was essential for the formation of migrasomes (Huang Y, Zucker B, Zhang S, Elias S, Zhu Y, Chen H, Ding T, Li Y, Sun Y, Lou J, Kozlov M M, Yu L. Migrasome formation was mediated by assembly of micron-scale tetraspanin macrodomains. Nat Cell Biol. 2019 August; 21(8): 991-1002). To explore the effect of cholesterol on the formation of engineered migrasomes, the isolated and purified engineered migrasomes were treated with methyl-β-cyclodextrin (MβCD) of cholesterol which was selectively extracted from plasma membranes. A cholesterol extraction reagent MβCD (10 mM) was added to droplets, which were inspected by a laser confocal microscope, with the results shown in FIG. 15. It was found that most of the engineered migrasomes underwent severe deformation and damage within 10 min, indicating that cholesterol had a crucial effect on the stability of the engineered migrasomes.

Drug Loading of Engineered Migrasomes

Example 8 Loading of Membrane Proteins on Engineered Migrasomes

Figure 16A:
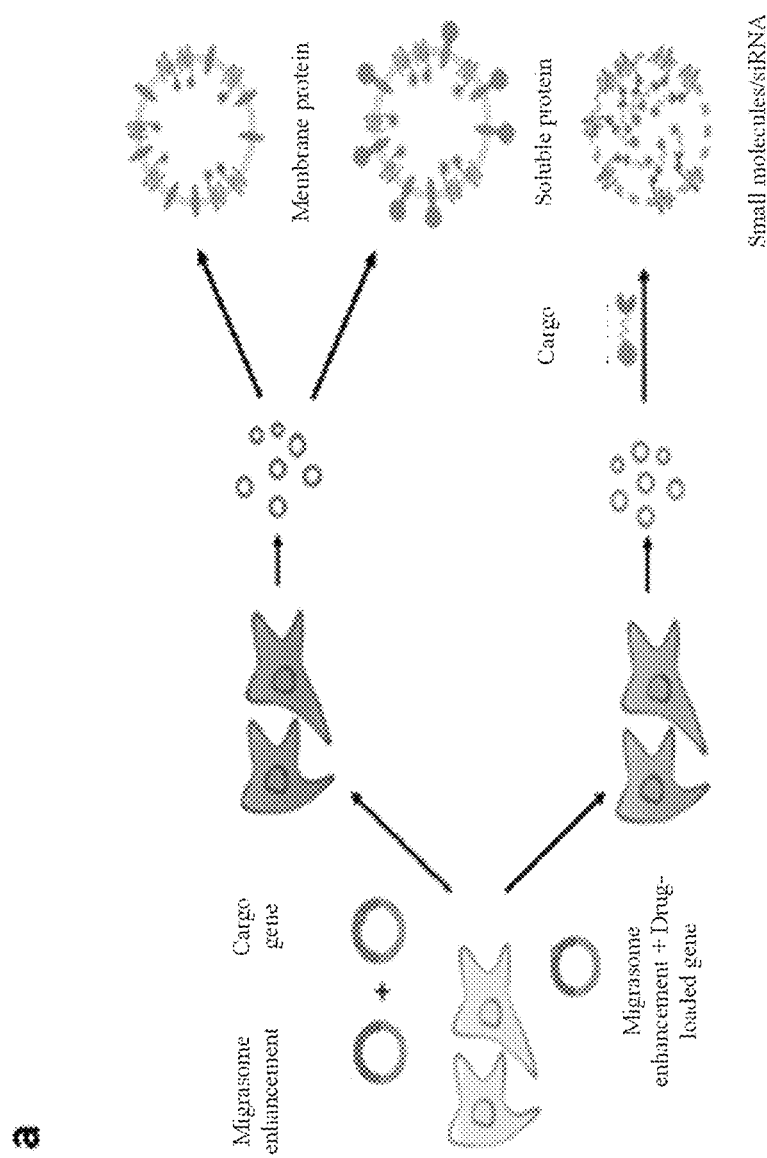
FIGS. 16A-16B show a schematic diagram of loading of membrane proteins, soluble proteins, and small molecules on engineered migrasomes (FIG. 16A) and a schematic diagram of loading of soluble proteins by using an OVA as an example (FIG. 16B).

During the preparation of engineered migrasomes, a portion of a cytomembrane could be converted into a migrasome membrane, and thus, the delivery of membrane proteins could be achieved by transferring plasmids encoding the genes of interest and Tspan4 directly into producer cells (FIG. 16A). The overexpression of Tspan4 combined with other steps in the preparation of engineered migrasomes could greatly increase the productivity of engineered migrasomes, and the overexpressed membrane proteins would be enriched on the resulting engineered migrasomes, thereby loading the membrane proteins on the engineered migrasomes. Loadable membrane proteins included various cellular receptors (such as various GPCR, PD-1, VEGFR or the like), extracellular enzymes (such as CD36 and CD73), ion channels, transporters, and various antigens (such as S proteins) and the like.

Figure 17:
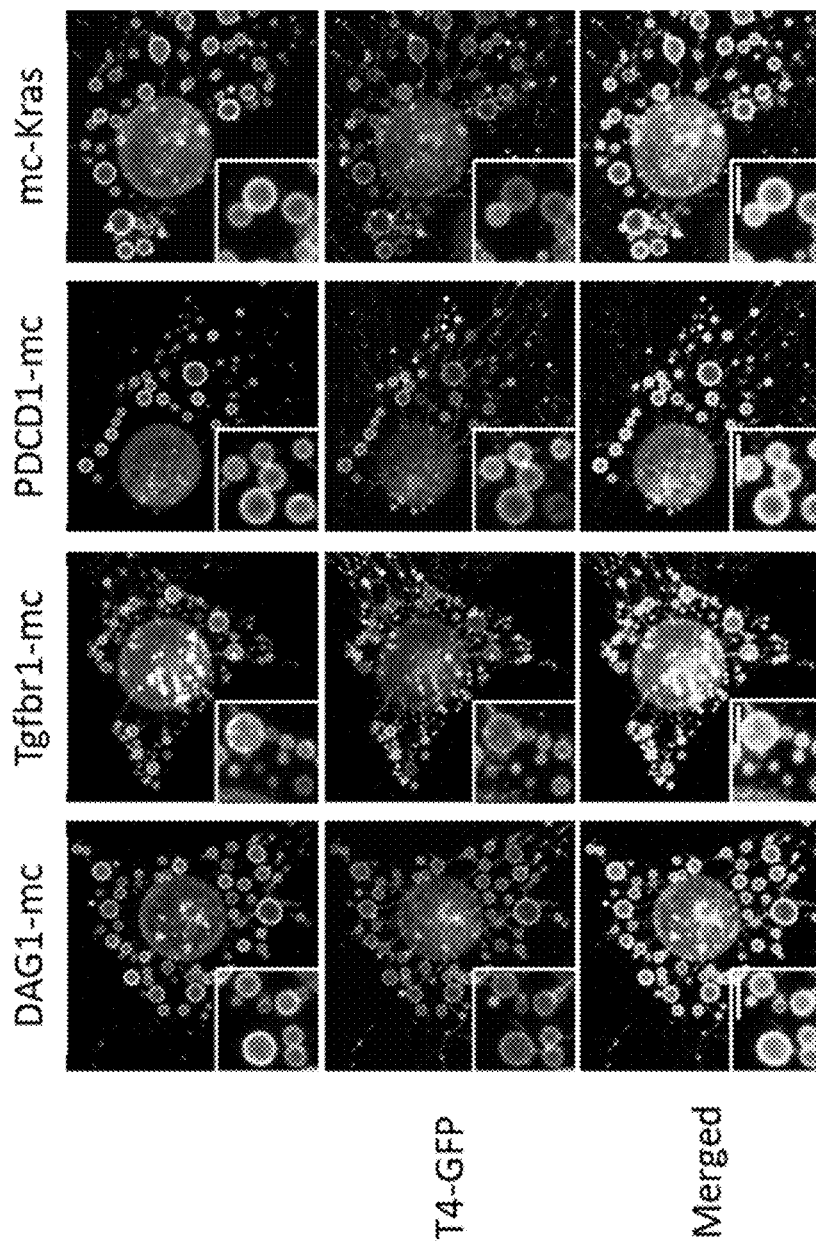
FIG. 17 shows locations of various loaded membrane proteins on engineered migrasomes as observed by a laser confocal microscope.
Figure 18:
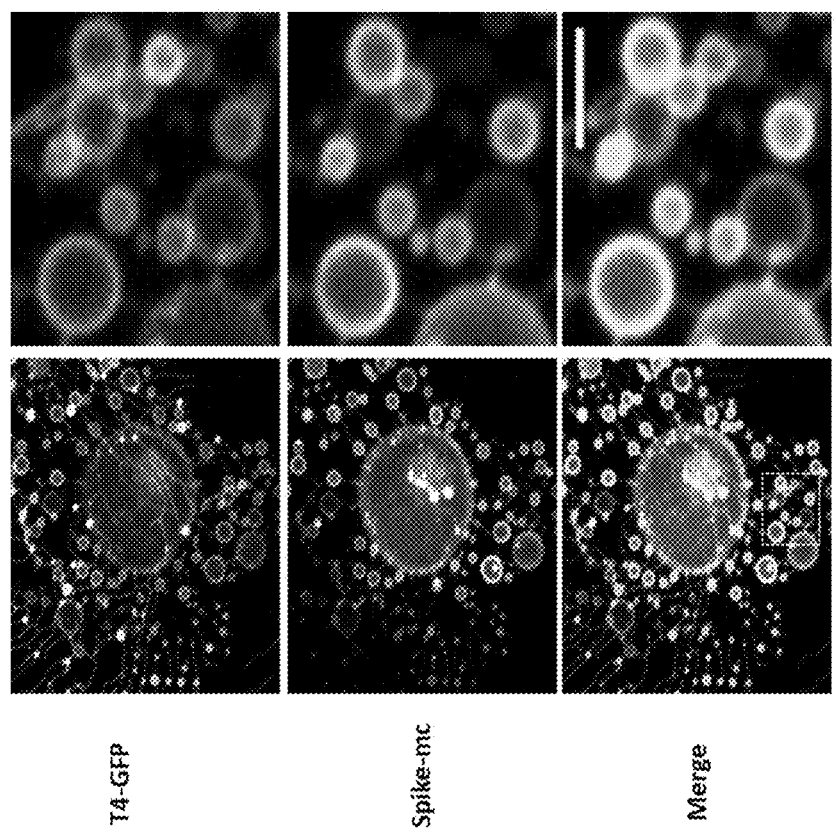
FIG. 18 shows locations of spike proteins on engineered migrasomes as observed by a laser confocal microscope.

As an example, the loading of three typical plasma membrane proteins DAG1, Tgfbr1 and PDCD1, a membrane-binding protein Kras (FIG. 17), and a spike (S) protein of SARS-CoV-2 (FIG. 18) on engineered migrasomes was verified.

For the membrane proteins DAG1, Tgfbr1, PDCD1, and Kras, plasmids containing Tspan4-GFP and the gene sequences of interest were transfected into producer NRK cells; and to facilitate the observation of subcellular localization and expression of the proteins of interest, the gene fragments of interest were fused to mCherry tags via linkers. The amino acid sequence and vector information of each fusion protein was shown as below.

Figure 19:
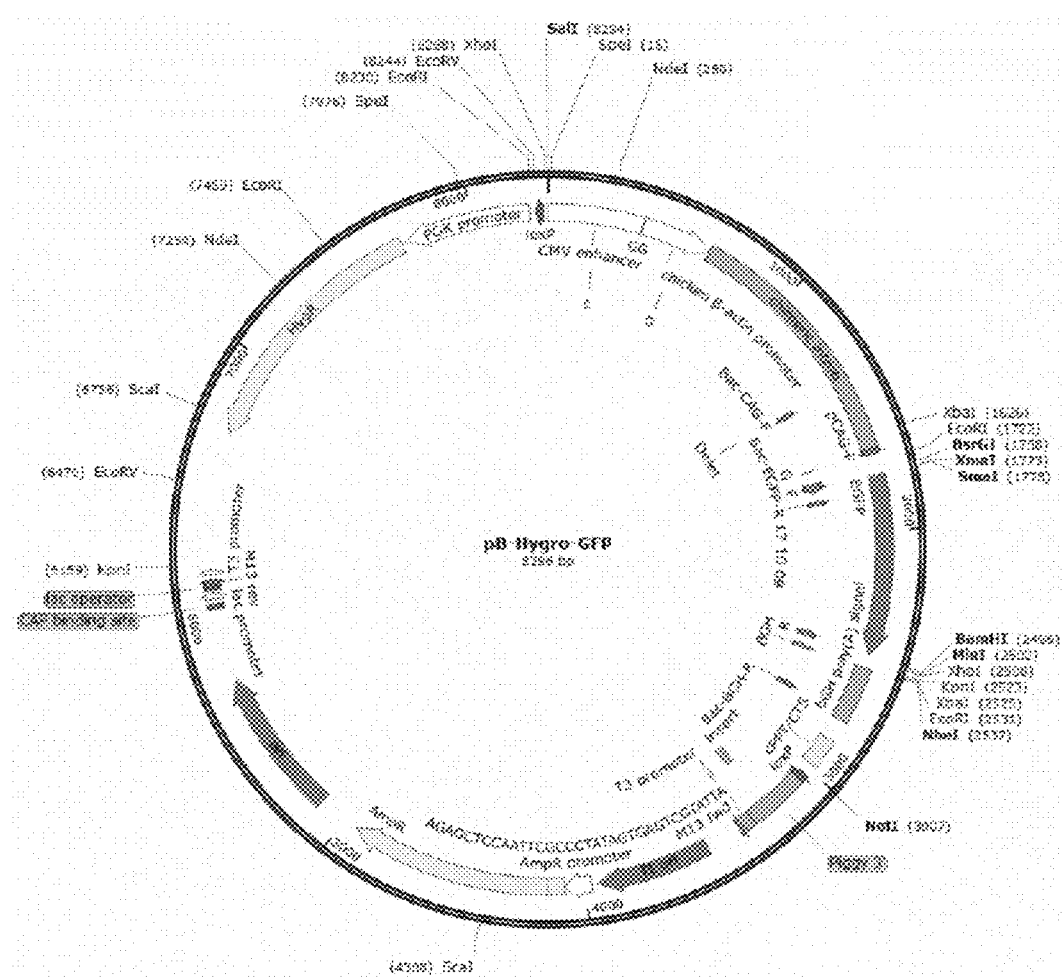
FIG. 19 shows a map of a vector pB-Hygro-GFP.

Tspan4-Linker-GFP (vector: pB-Hygro-GFP (with a vector map shown in FIG. 19), insertion site BsrGI+BamHI): (SEQ ID NO: 1)

MARGCLQGVKYLMFAFNLLFWLGGCGVLGVGIWLAATQGNFATLSSSFPSLSAANLLIVT

GTFVMAIGFVGCIGALKENKCLLLTFFVLLLLVFLLEATIAVLFFAYSDKIDSYAQQDLKKG

LHLYGTQGNVGLTNAWSIIQTDFRCCGVSNYTDWFEVYNATRVPDSCCLEFSDSCGLHEP

GTWWKSPCYETVKAWLQENLLAVGIFGLCTALVQILGLTFAMTMYCQVVKADTYCAPG

*MVSKGEELFTGVVPILVELDGDVNGHKFSVSGEGEGDATYGKLTLKFICTTGKLPVPWPTL*

*VTTLTYGVQCFSRYPDHMKQHDFFKSAMPEGYVQERTIFFKDDGNYKTRAEVKFEGDTLV*

*NRIELKGIDFKEDGNILGHKLEYNYNSHNVYIMADKQKNGIKVNFKIRHNIEDGSVQLADH*

*YQQNTPIGDGPVLLPDNHYLSTQSALSKDPNEKRDHMVLLEFVTAAGITLGMDELYK*

The amino acid sequence of Tspan4 was indicated by an underline; the amino acid sequence of GFP was indicated in bold italics; and the amino acid sequence between Tspan4 and GFP was a linker sequence (PG).

Figure 20:
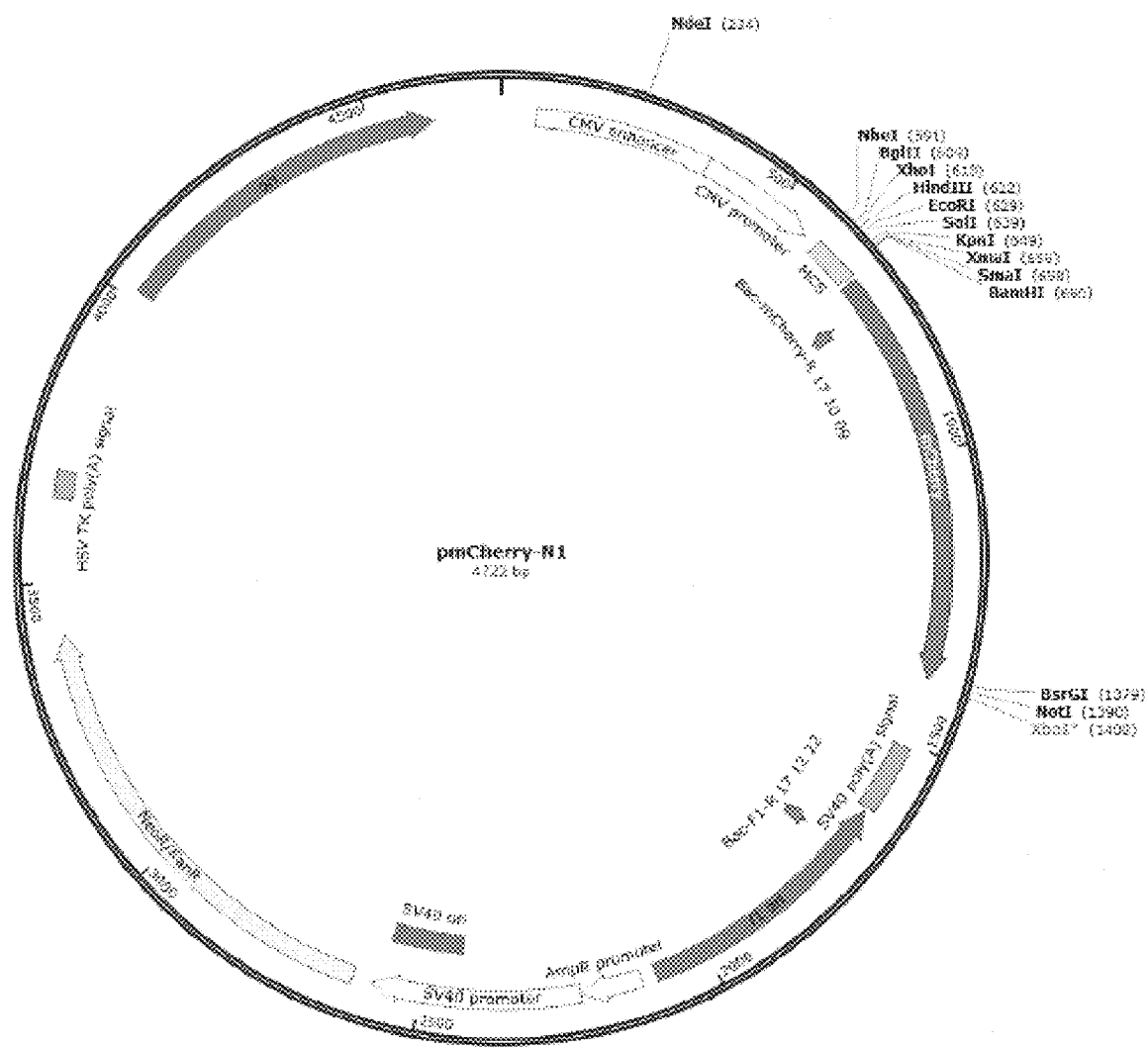
FIG. 20 shows a map of a vector pmCherry-N1.

DAG1-linker-mCherry (vector: pmCherry-N1 (with a vector map shown in FIG. 20), insertion site: EcoRI+KpnI): (SEQ ID NO:2)

MSVDNWLLHPLWGQTFLLLLSVAVAQAHWPSEPSEAVRDWKNQLEASMHSVLSDFQEA

VPTVVGIPDGTAVVGRSFRVSIPTDLIASSGEIIKVSAAGKEALPSWLHWDPHSHILEGLPLD

TDKGVHYISVSAARLGANGSHVPQTASVFSIEVYPEDHSEPQSVRAASSDPGEVVSSACAA

DEPVTVLTVILDADLTKMTPKQRIDLLNRMQSFSEVELNNMKLVPVVNNRLFDMSAFMAG

PGNAKKVVENGALLSWKLGCSLNQNSVPDIRGVETPAREGTMSAHLGYPVVGWHIANKK

PTLPKRIRRQIHATPTPVTAIGPPTTAIQEPPSRIVPTPTSPAIAPPTETMAPPVRDPVPGKPTV

TIRTRGAIIQTPTLGPIPPTRVSEAGTTVPGQIRPTLTIPGYVEPTAVVTPPTTTTKKPRVSTPK

PATPSTDSSTTTTRRPTKKPRTPRPVPRVTTKAPITRLETASPPTRIRTTTSAVPRGGEANQRP

ELKNHIDRVDAWVGTYFEVKIPSDTFYDNEDTTTDKLKLTLKLREQQLVGEKSWVQFNSN

SQLMYGLPDSSHVGKHEYFMHATDKGGLSAVDAFEIHVHKRPQGDKAPARFKAKLAGDP

APVVNDIHKKIALVKKLAFAFGDRNCSSITLQNITRGSIVVEWINNTLPLEPCPKEQIVGLSR

RIADENGKPRPAFSNALEPDFKALSVAVAGSGSCRHLQFIPVAPPSPGTSAAPATEVPDRDP

EKSSEDDVYLHTVIPAVVVAAILLIAGIIAMICYRKKRKGKLTLEDQATFIKKGVPIIFADEL

DDSKPPPSSSMPLILQEEKAPLPPPEYPNQSVPETTPLNQDTVGEYTPLRDEDPNAPPYQPPP

PFTAPMEGKGSRPKNMTPYRSPPPYVPPGDPPVAT*MVSKGEEDNMAIIKEFMRFKVHMEG*

*SVNGHEFEIEGEGEGRPYEGTQTAKLKVTKGGPLPFAWDILSPQFMYGSKAYVKHPADIPD*

*YLKLSFPEGFKWERVMNFEDGGVVTVTQDSSLQDGEFIYKVKLRGTNFPSDGPVMQKKT*

*MGWEASSERMYPEDGALKGEIKQRLKLKDGGHYDAEVKTTYKAKKPVQLPGAYNVNIKLD*

*ITSHNEDYTIVEQYERAEGRHSTGGMDELYK*

The amino acid sequence of DAG1 was indicated by an underline; the amino acid sequence of mCherry was indicated in bold italics; and the amino acid sequence between DAG1 and mCherry was a linker sequence (GDPPVAT).

Figure 21:
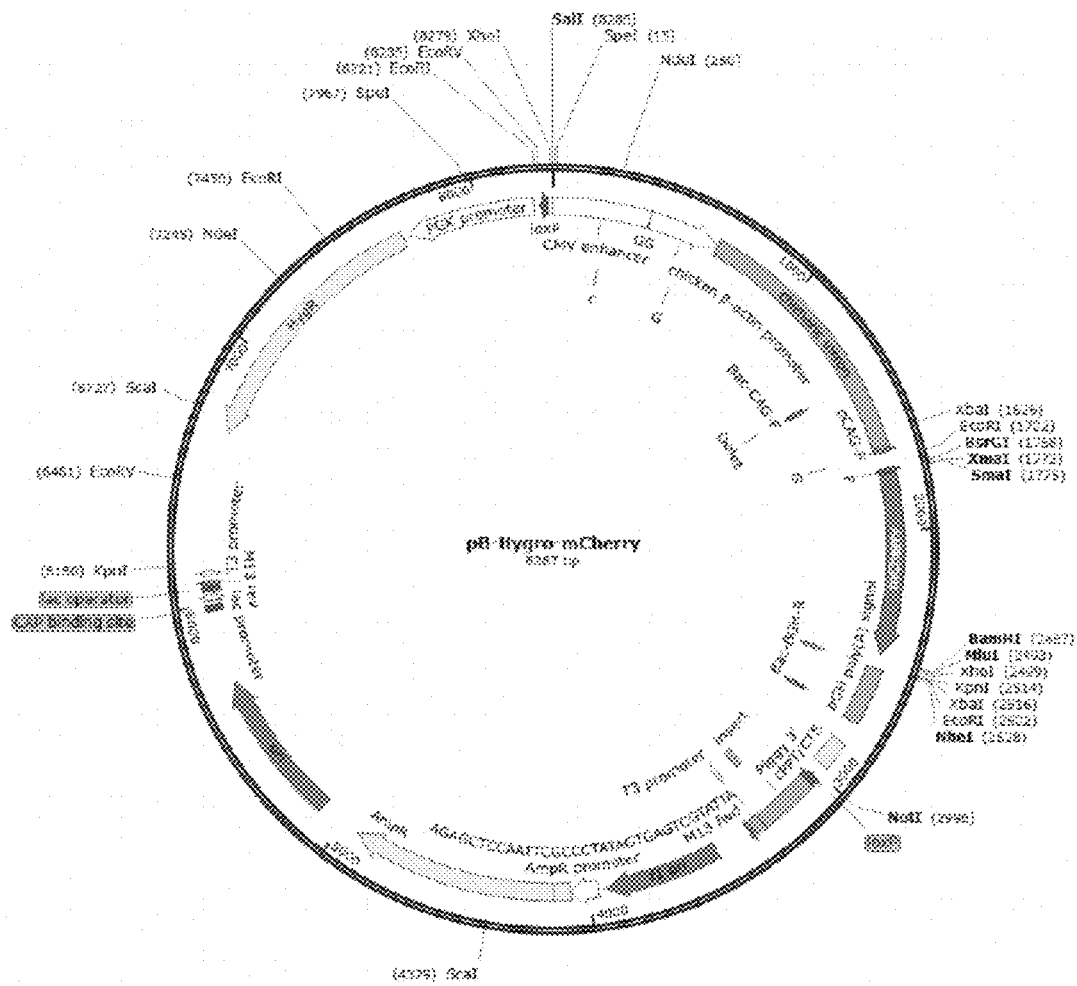
FIG. 21 shows a map of a vector pB-Hygro-mCherry.

PDCD1-linker-mCherry (vector: pB-Hygro-mCherry, (with a vector map shown in FIG. 21), insertion site: BsrGI+MluI): (SEQ ID NO: 3)

MWVRQVPWSFTWAVLQLSWQSGWLLEVPNGPWRSLTFYPAWLTVSEGANATFTCSLSN

WSEDLMLNWNRLSPSNQTEKQAAFCNGLSQPVQDARFQIIQLPNRHDFHMNILDTRRNDS

GIYLCGAISLHPKAKIEESPGAELVVTERILETSTRYPSPSPKPEGRFQGMVIGIMSALVGIPV

LLLLAWALAVFCSTSMSEARGAGSKDDTLKEEPSAAPVPSVAYEELDFQGREKTPELPTAC

VHTEYATIVFTEGLGASAMGRRGSADGLQGPRPPRHEDGHCSWPLTVPRARDPPVAT*MVS*

*KGEEDNMAIIKEFMRFKVHMEGSVNGHEFEIEGEGEGRPYEGTQTAKLKVTKGGPLPFA*

*WDILSPQFMYGSKAYVKHPADIPDYLKLSFPEGFKWERVMNFEDGGVVTVTQDSSLQDGE*

*FIYKVKLRGTNFPSDGPVMQKKTMGWEASSERMYPEDGALKGEIKQRLKLKDGGHYDAE*

*VKTTYKAKKPVQLPGAYNVNIKLDITSHNEDYTIVEQYERAEGRHSTGGMDELYK*

The amino acid sequence of PDCD1 was indicated by an underline; the amino acid sequence of mCherry was indicated in bold italics; and the amino acid sequence between PDCD1 and mCherry was a linker sequence (TVPRARDPPVAT).

Tgfbr1-linker-mCherry (vector: pmCherry-N1 (with a vector map shown in FIG. 20), insertion site: EcoRI+KpnI): (SEQ ID NO:4)

MEAAAAAPRRPQLLIVLVAAATLLPGAKALQCFCHLCTKDNFTCETDGLCFVSVTETTDK

VIHNSMCIAEIDLIPRDRPFVCAPSSKTGAVTTTYCCNQDHCNKIELPTTGPFSEKQSAGLGP

VELAAVIAGPVCFVCIALMLMVYICHNRTVIHHRVPNEEDPSLDRPFISEGTTLKDLIYDMT

TSGSGSGLPLLVQRTIARTIVLQESIGKGRFGEVWRGKWRGEEVAVKIFSSREERSWFREAE

IYQTVMLRHENILGFIAADNKDNGTWTQLWLVSDYHEHGSLFDYLNRYTVTVEGMIKLAL

STASGLAHLHMEIVGTQGKPAIAHRDLKSKNILVKKNGTCCIADLGLAVRHDSATDTIDIAP

NHRVGTKRYMAPEVLDDSINMKHFESFKRADIYAMGLVFWEIARRCSIGGIHEDYQLPYY

DLVPSDPSVEEMRKVVCEQKLRPNIPNRWQSCEALRVMAKIMRECWYANGAARLTALRI

KKTLSQLSQQEGIKMTVPRARDPPVAT*MVSKGEEDNMAIIKEFMRFKVHMEGSVNGHEF*

*EIEGEGEGRPYEGTQTAKLKVTKGGPLPFAWDILSPQFMYGSKAYVKHPADIPDYLKLSFP*

*EGFKWERVMNFEDGGVVTVTQDSSLQDGEFIYKVKLRGTNFPSDGPVMQKKTMGWEASS*

*ERMYPEDGALKGEIKQRLKLKDGGHYDAEVKTTYKAKKPVQLPGAYNVNIKLDITSHNEDY*

*TIVEQYERAEGRHSTGGMDELYK*

The amino acid sequence of Tgfbr1 was indicated by an underline; the amino acid sequence of mCherry was indicated in bold italics; and the amino acid sequence between Tgfbr1 and mCherry was a linker sequence (TVPRARDPPVAT).

mCherry-linker-Kras (vector: pB-Hygro-mCherry (with a vector map shown in FIG. 21), insertion site: BsrGI+MluI): (SEQ ID NO: 5)

MVSKGEEDNMAIIKEFMRFKVHMEGSVNGHEFEIEGEGEGRPYEGTQTAKLKVTKGG

PLPFAWDILSPQFMYGSKAYVKHPADIPDYLKLSFPEGFKWERVMNFEDGGVVTVTQDSS

LQDGEFIYKVKLRGTNFPSDGPVMQKKTMGWEASSERMYPEDGALKGEIKQRLKLKDGG

HYDAEVKTTYKAKKPVQLPGAYNVNIKLDITSHNEDYTIVEQYERAEGRHSTGGMDELYK

SGLRSRG*MTEYKLVVVGAGGVGKSALTIQLIQNHFVDEYDPTIEDSYRKQVVIDGETCLLDI*

*LDTAGQEEYSAMRDQYMRTGEGFLCVFAINNTKSFEDIHHYREQIKRVKDSEDVPMVLVG*

*NKCDLPSRTVDTKQAQELARSYGIPFIETSAKTRQGVDDAFYTLVREIRKHKEKMSKDGKK*

*KKKKSRTRCIVM*

The amino acid sequence of mCherry was indicated by an underline; the amino acid sequence of Kras was indicated in bold italics; and the amino acid sequence between mCherry and Kras was a linker sequence (SGLRSRG).

After transfection, the cells were treated with antibiotics and screened for resistance encoded by the plasmids, so as to establish cell lines that stably expressed various mCherry-tagged membrane proteins. Then, with the hypotonic treatment conditions for NRK cells in Example 5, the cell lines were induced to produce engineered migrasomes that had been reloaded with corresponding membrane proteins, and then observations were carried out by the laser confocal microscope. The results showed that all four membrane proteins of interest were correctly localized on the engineered migrasomes (FIG. 17), indicating that the membrane proteins could be incorporated onto the engineered migrasomes.

For S proteins, plasmids containing Tspan4-GFP and the gene sequences of interest were transfected into producer MC38 cells, and to facilitate the observation of subcellular localization and expression of the proteins of interest, mCherry tags were fused to the gene fragments of interest. After transfection, the cells were treated with antibiotics and screened for resistance encoded by plasmids, so as to establish cell lines that stably expressed mCherry-tagged S proteins. Then, with the hypotonic treatment conditions for MC38 cells in Example 5, the cell lines were induced to produce engineered migrasomes that had been loaded with S proteins, and then observations were carried out by the laser confocal microscope. The results showed that the S proteins of interest were correctly localized on the engineered migrasomes (FIG. 18), indicating that the S proteins could be effectively incorporated onto the engineered migrasomes.

Example 9 Loading of Soluble Proteins on Engineered Migrasomes

Figure 16B:
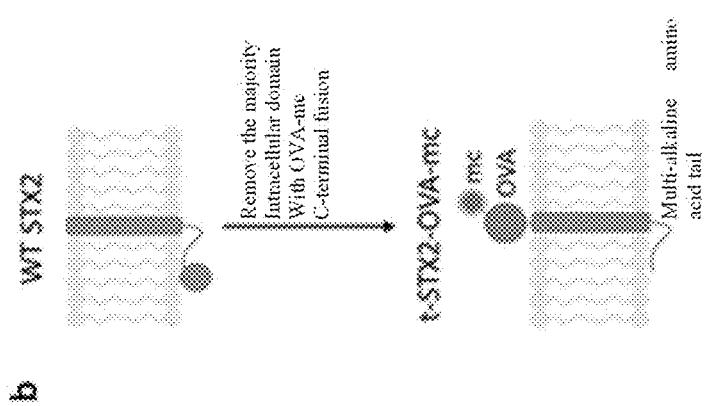

Since the engineered migrasomes were permeable, they were not likely to be used for direct delivery of cytosolic soluble proteins. To achieve the delivery of soluble proteins, the permeation of soluble proteins could be prevented by allowing producer cells to express the fusion proteins of the proteins of interest and membrane proteins, so as to anchor the soluble proteins on membranes (FIGS. 16*a* and 16B). For example, the N-terminus of syntaxin-2 (STX2) of the membrane protein could be modified to remove its intracellular terminal function to obtain truncated t-STX2. Then, the soluble protein was linked to the extracellular C-terminus of t-STX2 to form a soluble protein-t-STX2 fusion protein (FIG. 16*b*), allowing the soluble protein to be expressed as an artificial plasma membrane localization fusion protein. The topology of t-STX2 itself caused the soluble proteins of interest to be eventually hung outside the cytomembrane, making it easier for the proteins to be recognized by the immune system as intact antigens, for example.

In addition to STX2, a variety of other membrane proteins were often used as membrane-anchored proteins, for example, Tetraspanin-4, CD81, CD9, CD63, PDGFR, Lamp2b and the like.

As an example, the loading of soluble proteins OVAs on engineered migrasomes was verified. Plasmids containing Tspan4-GFP and t-STX2-OVA-mCherry encoding sequences were transfected into producer MC38 cells. The amino acid sequence and vector information for the fusion proteins of t-STX2 and OVA were shown as below.

t-STX2-linker-OVA-linker-mCherry (vector pmCherry-N1 (with a vector map shown in FIG. 20), insertion site: HindIII+BamHI): (SEQ ID NO: 6)

MKKAIKYQSKARRKKWIIAAVAVAVIAVLALIIGLSVGKGSMGSIGAASMEFCFDVF

KELKVHHANENIFYCPIAIMSALAMVYLGAKDSTRTQINKVVRFDKLPGFGDSIEAQCGTS

VNVHSSLRDILNQITKPNDVYSFSLASRLYAEERYPILPEYLQCVKELYRGGLEPINFQTAA

DQARELINSWVESQINGIIRNVLQPSSVDSQTAMVLVNAIVFKGLWEKAFKDEDTQAMPF

-continued

```
RVTEQESKPVQMMYQIGLFRVASMASEKMKILELPFASGTMSMLVLLPDEVSGLEQLESII

NFEKLTEWTSSNVMEERKIKVYLPRMKMEEKYNLTSVLMAMGITDVFSSSANLSGISSAES

LKISQAVHAAHAEINEAGREVVGSAEAGVDAASVSEEFRADHPFLFCIKHIATNAVLFFGR

CVSPGDPPVAT*MVSKGEEDNMAIIKEFMRFKVHMEGSVNGHEFEIEGEGEGRPYEGTQT*

*AKLKVTKGGPLPFAWDILSPQFMYGSKAYVKHPADIPDYLKLSFPEGFKWERVMNFEDGG*

*VVTVTQDSSLQDGEFIYKVKLRGTNFPSDGPVMQKKTMGWEASSERMYPEDGALKGEIKQ*

*RLKLKDGGHYDAEVKTTYKAKKPVQLPGAYNVNIKLDITSHNEDYTIVEQYERAEGRHSTG*

*GMDELYK*
```

The amino acid sequence of t-STX2 was indicated in bold; the amino acid sequence of OVA was indicated by an underline; and the amino acid sequence of mCherry was indicated in bold italics.

Figure 22:
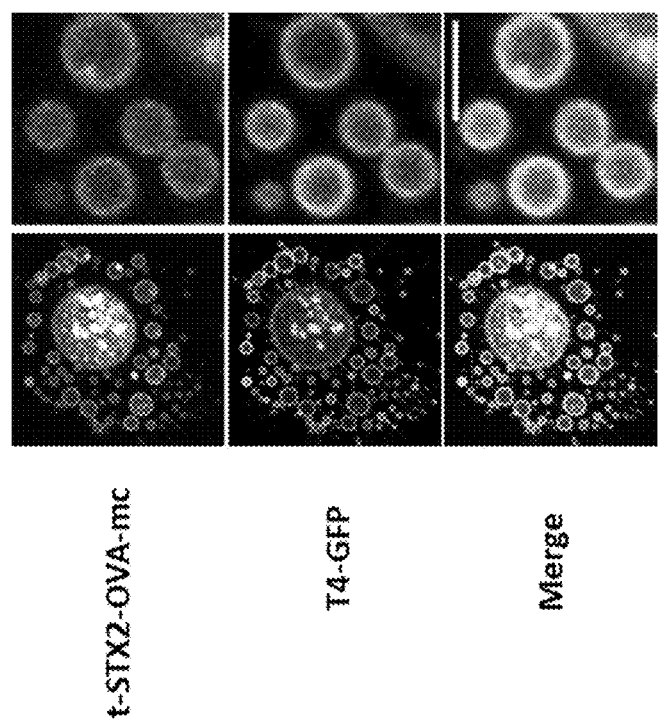
FIG. 22 shows locations of fusion proteins t-STX2-OVA on engineered migrasomes as observed by a laser confocal microscope.

After transfection, the cells were treated with antibiotics and screened for resistance encoded by the plasmids, so as to establish cell lines that stably expressed the mCherry-tagged t-STX2-OVA fusion proteins. Then, with the hypotonic treatment conditions for MC38 cells in Example 5, the cell lines were induced to produce engineered migrasomes that had been loaded with t-STX2-OVA fusion proteins, and then observations were carried out by the laser confocal microscope, with the results shown in FIG. 22.

The results showed that the t-STX2-OVA fusion proteins were correctly localized on the engineered migrasomes, indicating that the soluble proteins OVAs were successfully loaded onto the engineered migrasomes.

Example 10 Loading of Other Molecules of Interest on Engineered Migrasomes

The loading of small molecule drugs, small nucleic acid drugs, peptide fragments or other molecules of interest in engineered migrasomes could be achieved by modifying the molecules of interest and producer cells by means of antigen-antibody, receptor-ligand, and biotin-avidin binding systems (FIG. 16A). For example, the receptor-ligand interaction between HaloTag and an artificial ligand thereof (Los, G. V., Encell, L. P., McDougall, M. G., Hartzell, D. D., Karassina, N., Zimprich, C., Wood, M. G., Learish, R., Ohana, R. F., Urh, M., Simpson, D., Mendez, J., Zimmerman, K., Otto, P., Vidugiris, G., Zhu, J., Darzins, A., Klaubert, D. H., Bulleit, R. F., & Wood, K. V. (2008). HaloTag: a novel protein labeling technology for cell imaging and protein analysis. ACS chemical biology, 3(6), 373-382.) could be used to achieve the loading of the molecules of interest on the engineered migrasomes. First, the plasmids of fusion proteins Tspan4-HaloTag encoding membrane proteins Tspan4 and receptor proteins HaloTag were constructed. Then, the plasmids were transfected into producer cells for engineered migrasomes to modify the producer cells. The modified producer cells were induced to produce engineered migrasomes, and after isolation and purification, the engineered migrasomes contained the receptor proteins HaloTag on their membranes. The molecules of interest were modified by conjugating the molecules of interest to the ligands of HaloTag to form molecule of interest-ligand conjugates. Then, the molecule of interest-ligand conjugates were then co-incubated in vitro with the engineered migrasomes containing HaloTags in their membranes, and the molecules of interest were immobilized to the membranes and/or interiors of the engineered migrasomes by the interaction of HaloTags with their ligands. The covalent conjugation of HaloTags to their ligands was specific, efficient, and irreversible.

In addition to Tspan4, other membrane proteins, for example the membrane proteins described elsewhere herein, could also be used as membrane-anchored proteins for loading of the molecules of interest on the engineered migrasomes. In addition to HaloTags and their ligands, other antigen-antibody, receptor-ligand, biotin-avidin, or other binding systems, for example, a CP05-CD63 binding system, could also be used for loading of the molecules of interest on the engineered migrasomes (X. Gao, N. Ran, X. Dong, B. Zuo, R. Yang, Q. Zhou, H. M. Moulton, Y. Seow, H. Yin, Anchor peptide captures, targets, and cargos exosomes of diverse origins for diagnostics and therapy, Sci. Transl. Med. 10 (2018)), where the receptor CD63 was first loaded onto the membrane of the engineered migrasome, and then, the molecule of interest-CP05 conjugate was loaded onto the membrane of the C063-containing engineered migrasome by using the binding of CD63 to its ligand CP05. When the antigen-antibody, receptor-ligand, or biotin-avidin binding system was selected, receptors (e.g., PD-1) with a large number of natural ligands in vivo could be avoided to the greatest extent.

To achieve a proof of concept for this loading method, plasmids containing Tspan4-HaloTag-GFP encoding sequences were transfected into producer NRK cells, and plasmids containing Tspan4-GFP encoding sequences were transfected as controls. The amino acid sequence and vector information for the fusion proteins of Tspan4 and HaloTag were shown as below.

Tspan4-linker-GFP-linker-Halo (vector: pB-Hygro-GFP (with a vector map shown in FIG. 19), insertion site: BsrGI+MluI): (SEQ ID NO: 7)

```
MARGCLQGVKYLMFAFNLLFWLGGCGVLGVGIWLAATQGNFATLSSSFPSLSA

ANLLIVTGTFVMAIGFVGCIGALKENKCLLLTFFVLLLLVFLLEATIAVLFFAYSDKIDS

YAQQDLKKGLHLYGTQGNVGLTNAWSIIQTDFRCCGVSNYTDWFEVYNATRVPDSC

CLEFSDSCGLHEPGTWWKSPCYETVKAWLQENLLAVGIFGLCTALVQILGLTFAMT
```

-continued

MYCQVVKADTYCAPG<u>MVSKGEELFTGVVPILVELDGDVNGHKFSVSGEGEGDATYGKL</u>

<u>TLKFICTTGKLPVPWPTLVTTLTYGVQCFSRYPDHMKQHDFFKSAMPEGYVQERTIFFKDD</u>

<u>GNYKTRAEVKFEGDTLVNRIELKGIDFKEDGNILGHKLEYNYNSHNVYIMADKQKNGIKV</u>

<u>NFKIRHNIEDGSVQLADHYQQNTPIGDGPVLLPDNHYLSTQSALSKDPNEKRDHMVLLEFV</u>

<u>TAAGITLGMDELYKGS</u>*MAEIGTGFPFDPHYVEVLGERMHYVDVGPRDGTPVLFLHGNPT*

*SSYVWRNIIPHVAPTHRCIAPDLIGMGKSDKPDLGYFFDDHVRFMDAFIEALGLEEVVLVI*

*HDWGSALGFHWAKRNPERVKGIAFMEFIRPIPTWDEWPEFARETFQAFRTTDVGRKLIID*

*QNVFIEGTLPMGVVRPLTEVEMDHYREPFLNPVDREPLWRFPNELPIAGEPANIVALVEE*

*YMDWLHQSPVPKLLFWGTPGVLIPPAEAARLAKSLPNCKAVDIGPGLNLLQEDNPDLIGSE*

*IARWLSTLEISG*

The amino acid sequence of Tspan4 was indicated in bold; the amino acid sequence of GFP was indicated by an underline; and the amino acid sequence of Halo was indicated in bold italics.

Figure 23:
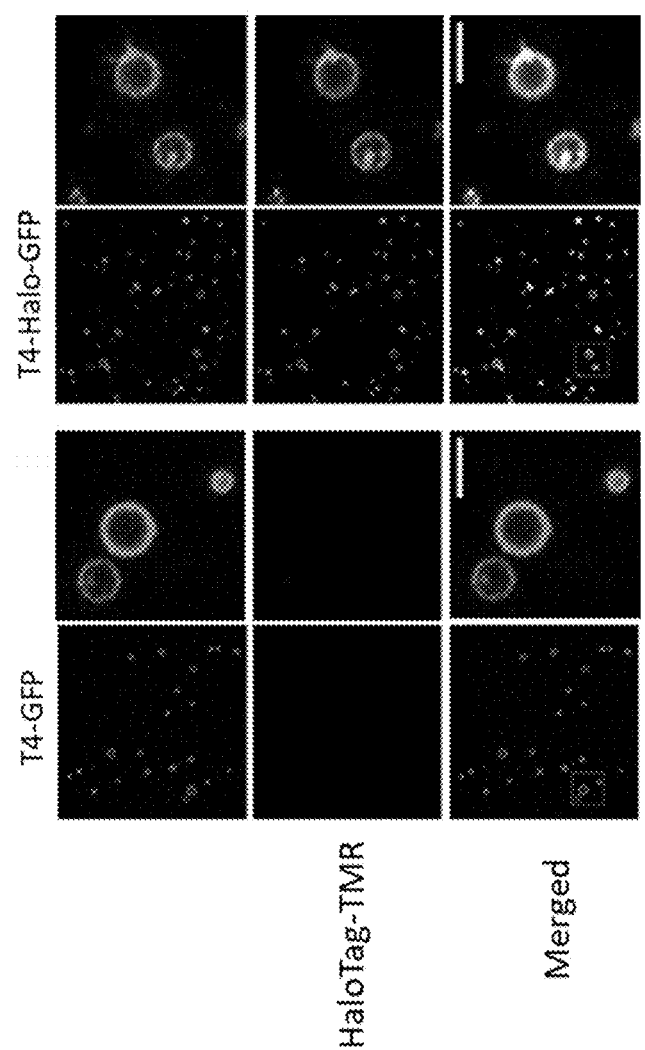
FIG. 23 shows colocalization of Tspan4-HaloTag-GFP and HaloTag ligand-TMR on engineered migrasomes as observed by a laser confocal microscope.

After transfection, the cells were treated with antibiotics and screened for resistance encoded by the plasmids, so as to establish cell lines with stable expression. Then, with the hypotonic treatment conditions for NRK cells in Example 5, the cell lines were induced to produce engineered migrasomes. A fluorescent HaloTag ligand-TMR dye was added to the engineered migrasomes, which were then incubated for 15 min at room temperature, washed twice with a dye-free buffer solution, added dropwise to a confocal capsule, allowed to stand for 5 h at room temperature, and then observes with a laser confocal microscope, with the results shown in FIG. 23.

The results showed that the HaloTag ligand-TMR and Tspan4-HaloTag-GFP were colocalized on the engineered migrasomes, indicating that the molecules of interest could be loaded onto the engineered migrasomes by means of the interaction of HaloTags and their ligands. Such loading was efficient, specific, and irreversible.

In addition to loading onto the engineered migrasomes by means of antigen-antibody, receptor-ligand, or biotin-avidin conjugation as described above, small nucleic acid drugs could also be loaded onto the membranes of engineered migrasomes by a variety of other modifications. For example, chemically modified siRNAs or antisense oligonucleotides (ASOs) could be conjugated to cholesterol to load small nucleic acid drugs onto the membranes of engineered migrasomes by means of the compatibility of cholesterol with cell membranes (S. S. Yemeni, S. Lathwal, P. Shrestha, H. Shirwan, K. Matyjaszewski, L. Weiss, E. S. Yolcu, P. G. Campbell, S. R. Das, Rapid on-demand extracellular vesicle augmentation with versatile oligonucleotide tethers, ACS Nano 13 (2019) 10555-10565). This approach was a rapid and inexpensive loading approach without additional modifications to the migrasomes. It was also possible to immobilize a siRNA conjugate onto the membrane (T. Tian, H. X. Zhang, C. P. He, S. Fan, Y. L. Zhu, C. Qi, N. P. Huang, Z. D. Xiao, Z. H. Lu, B. A. Tannous, J. Gao, Surface functionalized exosomes as targeted drug delivery vehicles for cerebral ischemia therapy, Biomaterials 150 (2018) 137-149). This approach required conjugating siRNA to a peptide fragment and then conjugating the peptide fragment to a membrane by click chemistry.

The loading of mRNA drugs on engineered migrasomes could be achieved by mRNA-binding proteins. Commonly used mRNA-binding proteins include L7Ae (Kojima, R., Bojar, D., Rizzi, G., Hamri, G. C., El-Baba, M. D., Saxena, P., Auslander, S., Tan, K. R., & Fussenegger, M. (2018). Designer exosomes produced by implanted cells intracerebrally deliver therapeutic cargo for Parkinson's disease treatment. Nature communications, 9(1), 1305; Zhitnyuk, Y., Gee, P., Lung, M., Sasakawa, N., Xu, H., Saito, H., & Hotta, A. (2018). Efficient mRNA delivery system utilizing chimeric VSVG-L7Ae virus-like particles. Biochemical and biophysical research communications, 505(4), 1097-1102) and MS2BP (Prel, A., Caval, V., Gayon, R., Ravassard, P., Duthoit, C., Payen, E., Maouche-Chretien, L., Creneguy, A., Nguyen, T. H., Martin, N., Piver, E., Sevrain, R., Lamouroux, L., Leboulch, P., Deschaseaux, F., Bouillé, P., Sensebe, L., & Pagès, J. C., Highly efficient in vitro and in vivo delivery of functional RNAs using new versatile MS2-chimeric retrovirus-like particles, Mol. Ther.—Meth. Clin. Dev. 2 (2015), 15039). First, plasmids, for example, Tspan4-L7Ae or Tspan4-MS2, encoding the fusion proteins of membrane proteins-mRNA-binding proteins were constructed. Next, mRNA expression plasmids containing protein-binding sites were constructed, the protein-binding site of L7Ae was C/D Box, and the protein-binding site of MS2BP was MS2 stem loop (MS2SL). Then, the fusion protein plasmids and the mRNA plasmids were co-transferred into producer cells, to induce the producer cells to produce engineered migrasomes, and after isolation and purification, the migrasome contained the mRNA molecules of interest on their membranes.

Figure 24A:
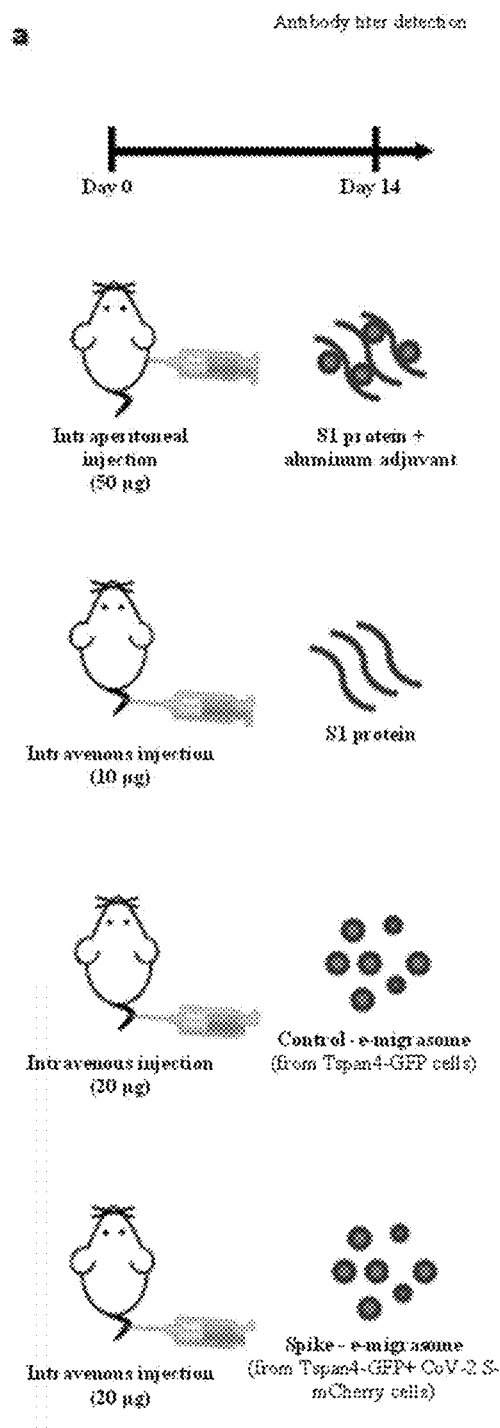
FIGS. 24A-24C show S protein-specific immune responses induced in mice immunized with engineered migrasomes (e-migrasomes) expressing SARS-CoV-2 spike proteins.

Example 11 Induction of Immune Responses in Mice with Engineered Migrasomes Loaded with SARS-CoV-2 Spike Proteins Experimental procedures were shown in FIG. 24A. Experimental animals were 8-week-old female mice of the C57BL/6 strain, with 5 mice in each group. The groups were specifically as follows:

I. 50 μg of S1 recombinant protein (SinoBiological)+aluminum adjuvant (thermo scientific), intraperitoneal injection (i.p.);

II. 10 μg of S1 recombinant protein, tail intravenous injection (i.v.);

III. Engineered migrasomes with the total protein of 20 μg and the expression of only Tspan4-GFP (NC-eMig), tail intravenous injection, as a negative control;

IV. Engineered migrasomes with the total protein of 20 μg and the co-expression of Tspan4-GFP and S protein-mCherry P (S-eMig), tail intravenous injection.

Figure 24B:
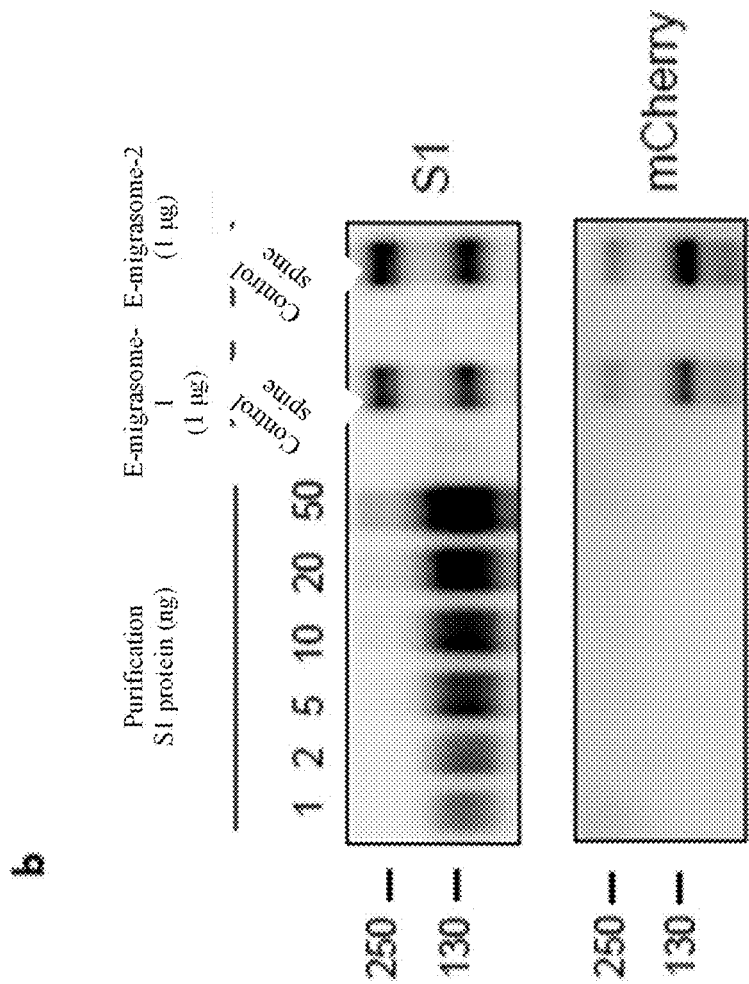

The S-eMig group was semi-quantitatively analyzed for S1 protein level by using Western blotting (FIG. 24B). The first 6 lanes from the left showed the S1 recombinant proteins of 1 ng, 2 ng, 5 ng, 10 ng, 20 ng, and 50 ng respectively, and lanes 7-10 showed NC-eMig or S-eMig with the total protein level of 1 μg, respectively (eMig-1 and eMig-2 represented samples from two independent experiments). By comparing the intensity of respective lane bands, it could be calculated that about 100 ng of the S1 protein was present in one dose (20 μg) of S-eMig, which is much less than the level of S1 recombinant protein used in the aluminum adjuvant group (50 μg).

Figure 24C:
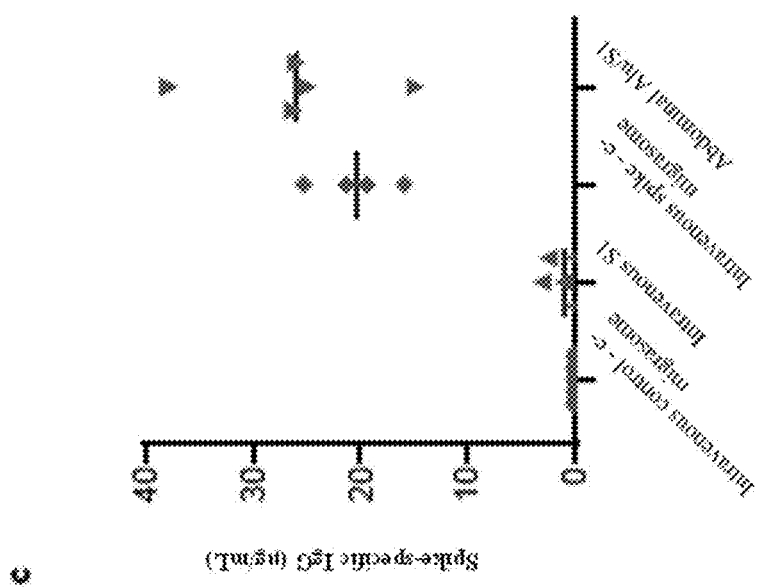

The mice were immunized once on day 0, and sacrificed on Day 14 to collect peripheral blood; and the concentration of S protein-specific IgG antibodies in serum was detected with ELISA, with the results shown in FIG. 24C. It was found that the single injection of neither the S1 protein group (Group II) nor the NC-eMig negative control group (Group III) could promote antibody production; both the S1 protein+aluminum adjuvant group (Group I) and the S-eMig group (Group IV) could effectively promote antibody production, and the immune effects of the two were roughly similar. This indicated that, compared with the traditional immunization with an adjuvant and an immunogenic protein, the engineered migrasome induced similar antibody responses without adjuvants and with low-level proteins, and thus was a more efficient delivery vector capable of effectively promoting the immune responses.

Comparison of Engineered Migrasomes with Known Extracellular Vesicles

Example 12 Comparison of Engineered Migrasomes and Naturally Occurring Migrasomes Control migrasomes (see Ma et al, Cell Res. 2015 for production and purification procedures) and engineered migrasomes (see FIG. 9 for production and purification procedures) from the same cell origin were produced and purified for a multifaceted comparison.

Figure 25A:
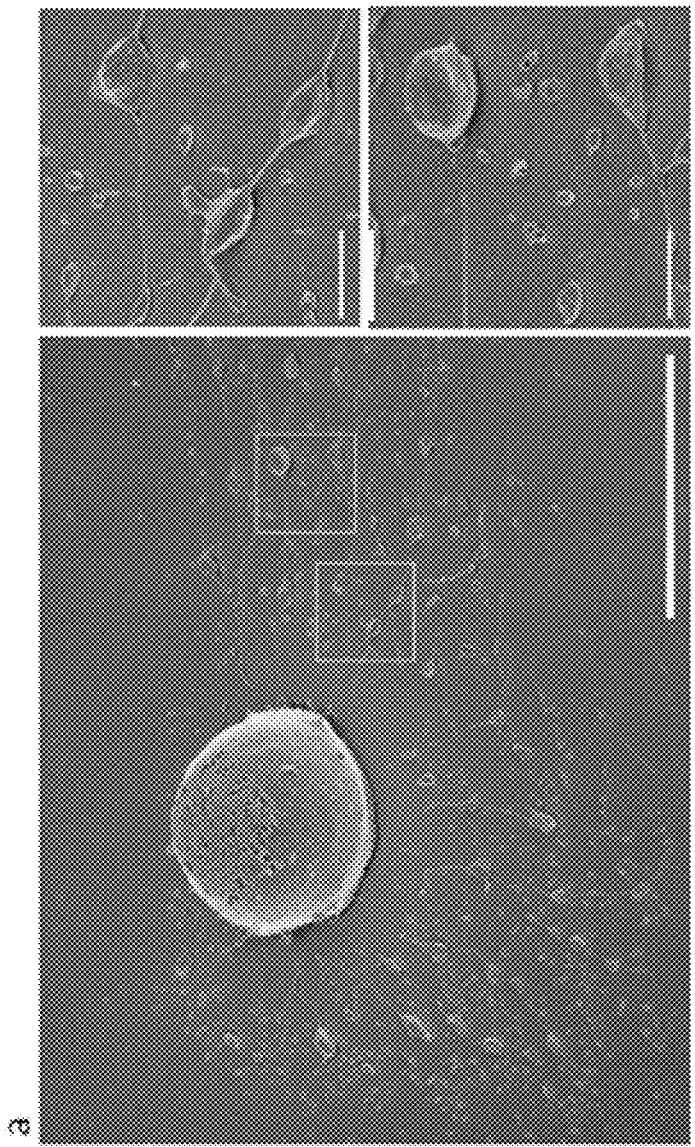
FIGS. 25A-25C show characterization of migrasomes produced by engineered NRK cells.
Figure 25B:
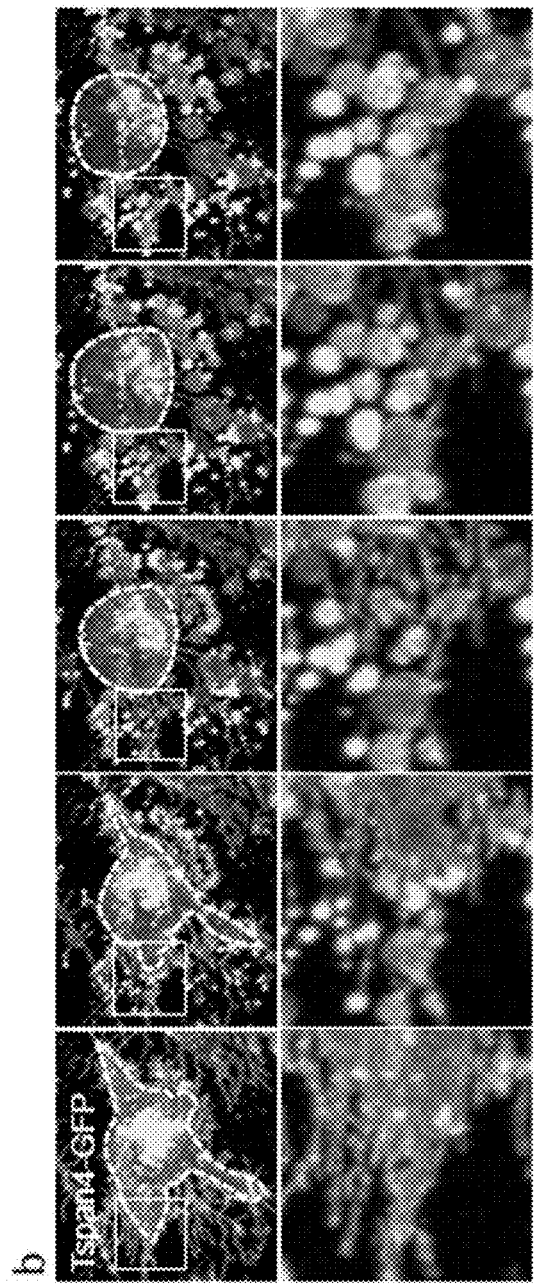

The Tspan4-GFP-overexpressing NRK cells were treated hypotonically, then fixed with 2.5% glutaraldehyde, and observed by a scanning electron microscope (FIG. 25A). 4D photography was carried out on the production of engineered migrasomes by Tspan4-GFP-overexpressing NRK cells by a spinning-disk confocal microscope. It could be observed that during hypotonic treatment, cell bodies expanded with basal surfaces retracted to produce a large number of filamentous structures, and the engineered migrasomes were grown on these filamentous structures (FIG. 25B).

Figure 26D:
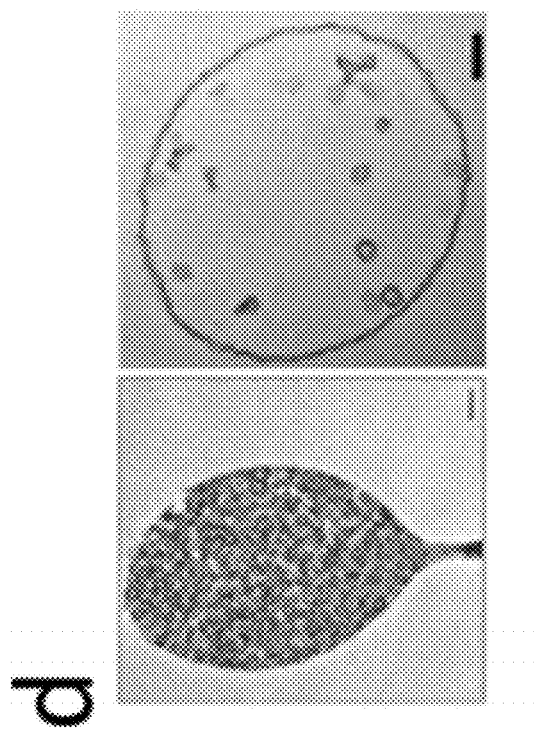
Figure 26E:
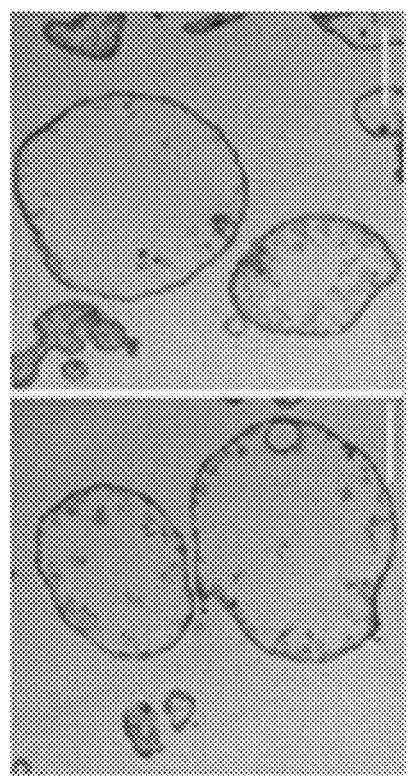
Figure 26F:
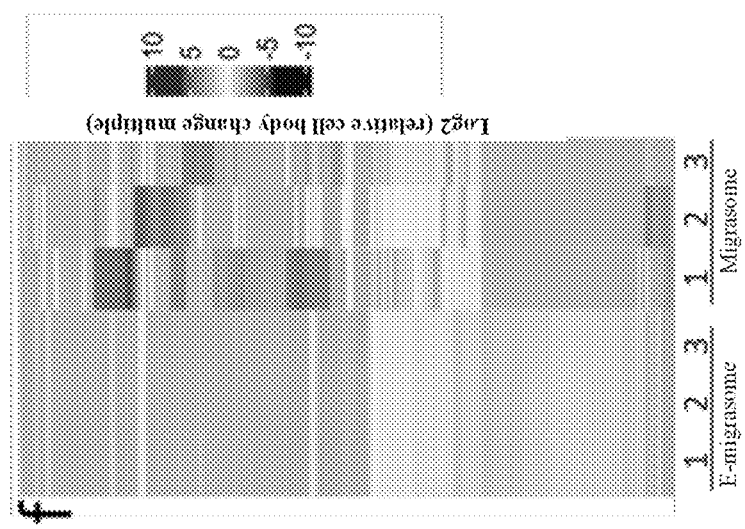
Figure 26H:
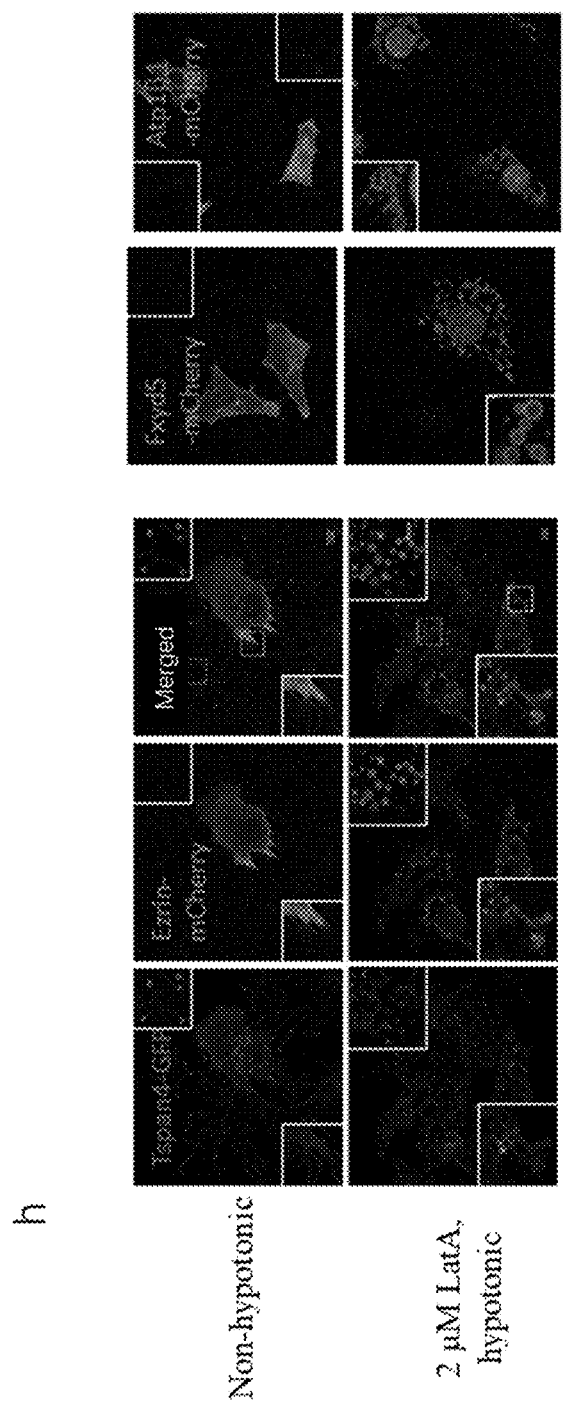

The naturally occurring migrasomes resulted from the movement of a cell center point, and were attached to retraction fibers that were located only at the wake of cell migration, and the number of these migrasomes was small (FIG. 26A). The engineered migrasomes resulted from the induced relative movement of cell membranes in different ways, and were attached to retraction fibers that could be distributed in all directions of the cells; and the number of migrasomes on each retraction fiber and in a single cell were significantly higher than that of control migrasomes (FIG. 26B). Tspan4-GFP-overexpressing NRK cells were stained with tetramethylrhodamine-labeled WGAs to clearly show the difference between the control migrasomes (top pane in FIG. 26c) and the engineered migrasomes (bottom pane in FIG. 26C). The naturally occurring migrasomes had different numbers of secretory vesicles inside under an electron microscope (FIG. 26D; from Ma et al, Cell Res. 2015), while the engineered migrasomes showed limited or no content under the electron microscope (FIG. 26E). Mass spectrometry carried out on the engineered migrasomes and control migrasomes (also called non-hypotonic migrasomes or naturally occurring migrasomes) from the same cell origin showed the absence of nearly 4000 proteins in the engineered migrasomes compared with the naturally occurring migrasomes (FIG. 26F), where some of the proteins were significantly enriched in the naturally occurring migrasomes than in cell bodies (FIG. 26G). In addition, the engineered migrasomes showed the expression of 1350 proteins that were absent in the naturally occurring migrasomes, and more proteins such as ERM family member proteins (including Ezrin) as well as Fxyd5 and Atp1β1 proteins were found expressed on the membranes of some of the engineered migrasomes (FIG. 26H). (References: Ma L, Li Y, Peng J, Wu D, Zhao X, Cui Y, Chen L, Yan X, Du Y, Yu L. Discovery of the migrasome, an organelle mediating release of cytoplasmic contents during cell migration. Cell Res. 2015 January; 25(1):24-38. doi: 10.1038/cr.2014.135.).

Example 13 Differences of Engineered Migrasomes from Other Hypotonic Vesicles

Figure 25C:
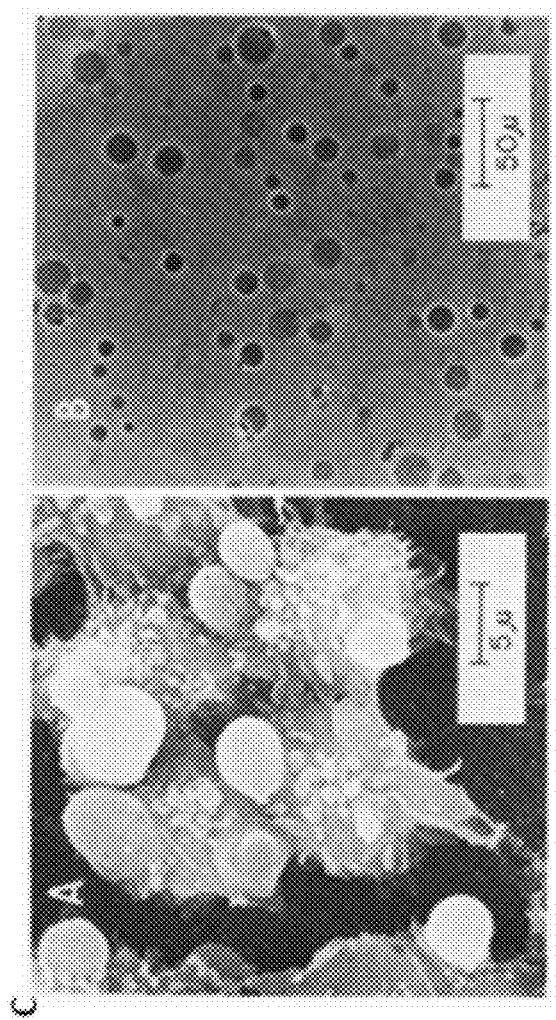

Under the scanning electron microscope, the engineered migrasomes (FIG. 25A) produced by NRK cells were found different from reported hypotonic vesicles (FIG. 25C). Their main differences in process and characteristics were as follows:
1) the engineered migrasomes were produced on fibers surrounding the cells, rather than on the upper surfaces of the cells as revealed by the experimental data from Cohen et al;
2) the engineered migrasomes had a micron-scale size and rarely exceeded 5 μm in diameter, while the vesicles made by Cohen et al. using hypoosmolality could be as large as 20 μm;
3) the hypotonic induction for the engineered migrasomes was a gentle stepwise reducing process (the final osmolality was not less than 40% in several current cell lines), while vigorous treatment with 5% PBS was used by Cohen et al., who used a 118% hypertonic buffer solution during vesiculation. (References: Cohen S, Ushiro H, Stoscheck C, Chinkers M A native 170 000 epidermal growth factor receptor-kinase complex from shed plasma membrane vesicles. J Biol Chem 257: 1523-1531.).

Example 14 Difference of Engineered Migrasomes from Small Extracellular Vesicles/Exosomes Migrasomes and exosomes were both extracellular vesicles, but differed in the mechanism of production, the size of vesicles (the exosomes were generally 50-150 nm) or other properties. Small extracellular vesicles (sEVs)/exosomes (see FIG. 27A for production and purification procedures) and engineered migrasomes (see FIG. 9 for production and purification procedures) from the same cell origin were compared in production, purification, and other different aspects. The NTA detection (FIG. 27B) and transmission electron microscope (TEM) observation (FIG. 27C) of purified exosomes demonstrated that the size and morphology of the exosomes were consistent with the literature description. In addition, Western blotting demonstrated that the purified exosomes were enriched with recognized extracellular vesicle/exosome markers such as tsg101, Alix, CD63, and CD81, while these small extracellular vesicle/exosome markers were not enriched in the engineered migrasomes. At the same time, the engineered migrasomes were enriched with more migrasome markers such as sodium/potassium ATPase and Lamp2 (FIG. 27D), indicating that the migrasomes and exosomes from the same cell origin were efficiently produced and purified, and showed significant differences in protein composition and marker.

Method for Producing an Engineered Migrasome:

Tspan4-GFP-overexpressing MC-38 cells were spread and cultured one day in advance in a cell culture dish treated with fibronectin.

On the day of the experiment, a supernatant was discarded, and the cells were washed with 40% KDPBS; h-KDPBS (h-KDPBS-BSA) containing 1 mg/ml BSA was added, and the resulting mixture was shaken for 3 min at 130 rpm; a supernatant was collected; h-KDPBS-BSA was added, the bottom surface of a culture flask was pipetted, and a collected liquid was combined with the supernatant from the previous step; centrifugation was carried out for 10 min at 4° C. at 300×g, and the supernatant was retained; centrifugation was carried out for 10 min at 4° C. at 500×g, and the supernatant was retained; the supernatant was filtered into a 50 ml low-adsorption tube by using a parylene filter membrane having a pore size of 8 μm; centrifugation was carried out for 45-60 min at 4° C. at 17000×g, and the supernatant was discarded; the pellets were resuspended with h-KDPBS-BSA and transferred into an EP tube (centrifuge tube 1), to which an equal volume of PBS-BSA was added; here, 1/50 of the total volume of the resultant was transferred to another centrifuge tube (centrifuge tube 2) for measurement of protein concentration; and centrifugation was carried out for 15-20 min at 4° C. at 17000×g, the supernatant was discarded, PBS was added, and the pellets were resuspended before injection to obtain the engineered migrasomes resuspended in PBS.

Production and Purification of Small Extracellular Vesicles;

MC-38 cell lines overexpressing mouse Tspan4-GFP proteins were seeded at the cell confluency of about 20% and cultured for 72 h; the culture medium was collected and centrifuged for 10 min at 4,000×rcf to remove cell bodies, and the supernatant was collected; the supernatant was filtered by using a filter membrane of 0.45 μm; the filtered supernatant was concentrated by using a 70 kD ultrafiltration tube; 1 mM $MgCl_2$ and 20 U/mL Benzonase were added to the concentrated supernatant and treated overnight at room temperature; the resultant was filtered by using a filter membrane of 0.22 μm; the filtered liquid was centrifuged for 1 h in an ultra-centrifuge at 4° C. at 140,000×g; the supernatant was discarded, and the pellets were collected and resuspend in PBS; the resuspended pellets were mixed with 60% iodixanol and add to the bottom of an ultra-centrifugal tube; 9 mL of 30% iodixanol, 5 mL of 23% iodixanol, and 6 mL of 18% iodixanol were added to the ultra-centrifugal tube in sequence; the resultant was centrifuged for 16 h at 150,000×g, and each inter-density gradient component (4 components in total, F1-F4) was gently pipetted and collected; the collected exosome components were mixed with 30 mL of PBS and centrifuged for 1 h at 16,000×g, and the supernatant was retained; and the supernatant was filtered with a filter membrane of 0.2 μm and then centrifuged for 2 h at 4° C. at 150,000×g, and the pellets were resuspended to $1\times10^{13}$ particles/mL and cryopreserved for later use.

Based on the production and purification of the small extracellular vesicles/exosomes and engineered migrasomes from the same cell line, the applicant found that the unit yield of the engineered migrasomes was far more than that of the small extracellular vesicles, and there was no need for ultra-centrifugation, density gradient ultra-centrifugation or the like, such that the production speed was greatly increased. When cultured with equivalent cells, the yield of the engineered migrasomes was about 35 times that of the small extracellular vesicles/exosomes (FIG. 27E).

Figure 27F:
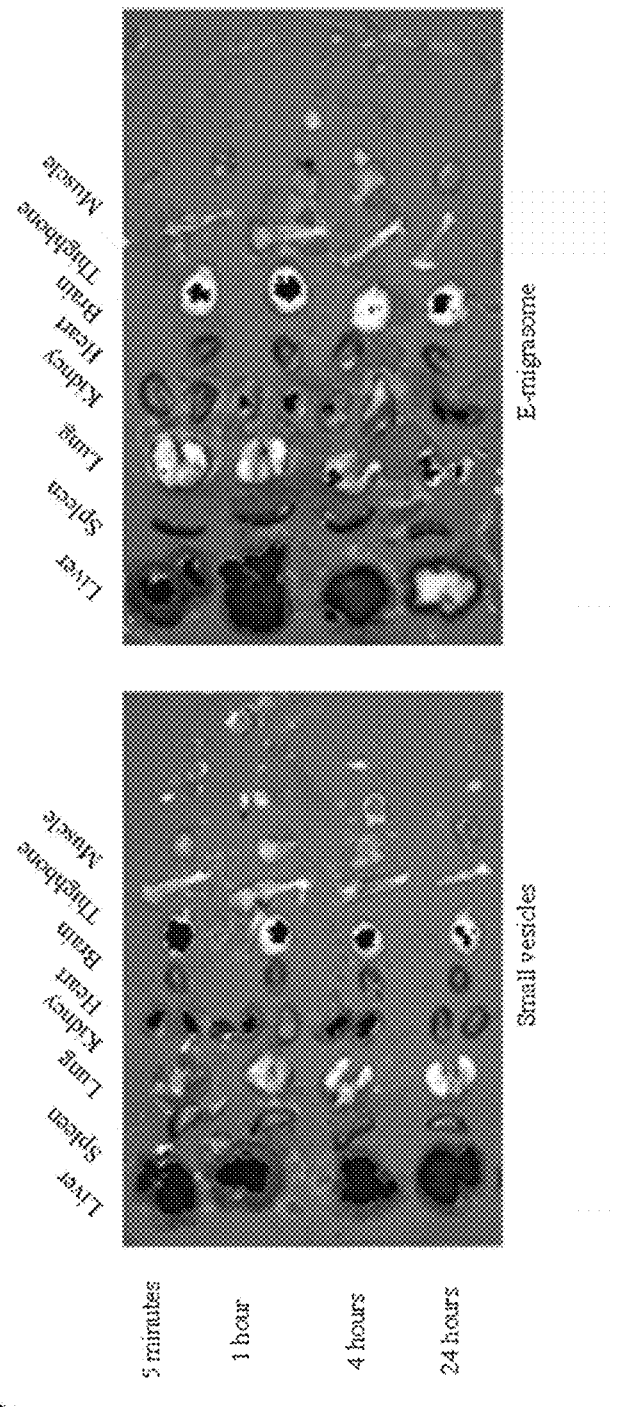

At the same time, 5 min after tail vein injection in C57BL/6 mice with the small extracellular vesicles and the engineered migrasomes with equal amount of dyes, the accumulation of the engineered migrasomes and the small extracellular vesicles in various organs was similar. With the increase of time, 4 hours and 24 hours after injection, the accumulation of the engineered migrasomes in the liver, spleen and lungs increased significantly as compared with the small extracellular vesicles, which also indicated the difference between the two in metabolism and tissue accumulation in vivo, and with an equal amount of dye, the delivery efficiency of the engineered migrasomes was better (FIG. 27F).

Mass spectrometry was carried out on the small extracellular vesicles/exosomes and engineered migrasomes from the same cell line, and PCA analysis showed that three engineered migrasome samples were highly similar, but were significantly different from three small extracellular vesicles/exosomes (FIG. 28A). The signaling pathway analysis heatmap (FIG. 28B) and the 10 most enriched proteins (FIG. 28C) showed significant differences between the small extracellular vesicles/exosomes and the engineered migrasomes.

The foregoing detailed description is provided by way of explanation and exemplification, and is not intended to limit the scope of the appended claims. Various changes of the embodiments listed in the present application until now would be obvious to those of ordinary skills in the art, and should be kept within the scope of the appended claims and equivalents thereof.

The invention claimed is:

1. A method for preparing an engineered migrasome, comprising treating a cell with (a) hypotonic treatment and inducing a cytomembrane to move relative to a surface adhered thereto.

2. The method according to claim 1, further comprising isolating said migrasome produced by said cell.

3. The method according to claim 1, wherein said hypotonic treatment comprises placing said cell in a hypotonic buffer solution.

4. The method according to claim 3, wherein the osmolality of said hypotonic buffer solution is less than about 305 mOsmol/L.

5. The method according to claim 1, wherein said hypotonic treatment comprises placing said cell in a buffer solution and reducing an osmolality of said buffer solution to turn said buffer solution into said hypotonic buffer solution.

6. The method according to claim 1, wherein said migrasome has one or more of the following characteristics:

(a) having a size of about 50 nm to about 8000 nm;
(b) generating from a retraction fiber of said cell;
(c) the density of sodium/potassium ATPase and/or a functional fragment thereof, an integrin and/or a functional fragment thereof, a tetraspanin protein, a functional variant thereof and/or a functional fragment thereof, cholesterol, and/or a membrane microdomain being relatively higher on said migrasome than on the cytomembrane producing said migrasome; and
(d) being different from the naturally occurring migrasome produced by a corresponding cell in terms of structure and biochemical composition.

7. The method according to claim 1, wherein said cell comprises a cultured cell line, a primary cell, a tumor cell, a leukocyte, a stem cell, a fat cell, and/or a fibroblast.

8. The method according to claim 7, wherein said primary cell comprises a liver cell, a spleen cell, a kidney cell, a tissue macrophage, a cerebral glial cell, an osteoclast, a bone marrow cell, a leukocyte, a fibroblast, and/or a fat cell.

9. The method according to claim 7, wherein said tumor cell comprises a tumor cell line, a primary or limited-passaged tumor cell derived from a patient, a tumor stromal cell, and/or a tumor organoid.

10. The method according to claim 1, further comprising characterizing said migrasome produced by said cell, said characterizing comprises one or more of the followings:
    (a) identifying the size of said migrasome as 50-8000 nm in diameter;
    (b) assessing whether said migrasome is stable under room temperature;
    (c) assessing whether the stability of said migrasome depends on cholesterol; and
    (d) assessing whether said migrasome is permeable.

11. The method according to claim 1, further comprising one or more of the following:
    (a) disrupting the cytoskeleton of the cell;
    (b) suppressing a cell volume-regulatory function of said cell;
    (c) detaching said cell from a surface adhered thereto;
    (d) increasing a number and/or function of a tetraspanin protein, a functional fragment thereof and/or a functional variant thereof in said cell; and
    (e) reducing the size of said migrasome.

12. The method according to claim 11, wherein disrupting the cytoskeleton of said cell comprises bringing said cell into contact with a cytoskeleton-disrupting reagent.

13. The method according to claim 12, wherein said cytoskeleton-disrupting reagent comprises a microfilament and/or microtubule depolymerizing agent.

14. The method according to claim 11, wherein suppressing the cell volume-regulatory function of said cell comprises:
    (a) decreasing the number and/or function of a volume-regulatory protein in said cell; and/or
    (b) placing said cell in a buffer solution that can inhibit the volume regulatory ability of the said cell.

15. The method according to claim 14, wherein said volume-regulatory protein comprises a volume-regulatory ion channel and/or a transporter.

16. The method according to claim 14, wherein said buffer solution comprises solution with replaced cation, and/or solution with reduced salt concentration, wherein the solution with reduced salt concentration is relative to isotonic solution.

17. The method according to claim 16, wherein said buffer solution with replaced cation comprising buffer solution wherein potassium ions, cesium ions, or choline ions replace sodium ions, wherein said buffer solution comprises DPBS buffer.

18. The method according to claim 11, comprising allowing said cell to overexpress said tetraspanin protein, functional fragments thereof and/or functional variants thereof.

19. The method according to claim 11, wherein said size reduction methods of said migrasome comprise passing said migrasome through a filter or an extruder, wherein said filter or extruder has a pore size of about 30 nm to about 10000 nm.

* * * * *